US012590880B2

(12) United States Patent
Cairns et al.

(10) Patent No.: US 12,590,880 B2
(45) Date of Patent: Mar. 31, 2026

(54) FLARE (FLOW CYTOMETRY ATTENUATED REPORTER EXPRESSION) TECHNOLOGY FOR RAPID BULK SORTING

(71) Applicant: Genzyme Corporation, Cambridge, MA (US)

(72) Inventors: Victor R. Cairns, Cambridge, MA (US); Jose Ignacio Sancho Chavida, Cambridge, MA (US); Christine DeMaria, Cambridge, MA (US)

(73) Assignee: Genzyme Corporation, Cambridge, MA (US)

( * ) Notice: Subject to any disclaimer, the term of this patent is extended or adjusted under 35 U.S.C. 154(b) by 27 days.

(21) Appl. No.: 18/181,803

(22) Filed: Mar. 10, 2023

(65) Prior Publication Data

US 2023/0304913 A1      Sep. 28, 2023

Related U.S. Application Data

(62) Division of application No. 15/288,036, filed on Oct. 7, 2016, now Pat. No. 11,635,363.

(60) Provisional application No. 62/239,515, filed on Oct. 9, 2015.

(51) Int. Cl.
| | |
|---|---|
| *G01N 15/14* | (2024.01) |
| *C07K 16/00* | (2006.01) |
| *C12N 15/10* | (2006.01) |
| *C12N 15/85* | (2006.01) |
| *G01N 15/149* | (2024.01) |
| *G01N 33/50* | (2006.01) |

(52) U.S. Cl.
CPC ............. *G01N 15/14* (2013.01); *C07K 16/00* (2013.01); *C12N 15/1086* (2013.01); *C12N 15/85* (2013.01); *G01N 33/5044* (2013.01); *C07K 2317/10* (2013.01); *C12N 2510/02* (2013.01); *G01N 15/149* (2024.01); *G01N 2333/70592* (2013.01)

(58) Field of Classification Search
None
See application file for complete search history.

(56) References Cited

U.S. PATENT DOCUMENTS

| | | | |
|---|---|---|---|
| 4,812,405 A | 3/1989 | Lair et al. |
| 4,818,700 A | 4/1989 | Cregg et al. |
| 4,929,555 A | 5/1990 | Cregg et al. |
| 4,937,190 A | 6/1990 | Palmenberg et al. |
| 5,429,746 A | 7/1995 | Shadle et al. |
| 5,648,267 A | 7/1997 | Reff |
| 5,736,383 A | 4/1998 | Raymond |
| 5,888,768 A | 3/1999 | Raymond |
| 5,955,349 A | 9/1999 | Raymond |
| 6,258,559 B1 | 7/2001 | Zamost |
| 6,653,132 B1 | 11/2003 | Keshet et al. |
| 6,833,254 B2 | 12/2004 | Dasgupta et al. |
| 7,344,886 B2 | 3/2008 | Enenkel et al. |
| 7,759,119 B2 | 7/2010 | Allbritton et al. |
| 7,776,584 B2 | 8/2010 | Richmond et al. |
| 8,034,612 B2 | 10/2011 | Richmond et al. |
| 8,034,625 B2 | 10/2011 | Richmond et al. |
| 8,293,520 B2 | 10/2012 | Richmond et al. |
| 8,293,525 B2 | 10/2012 | Richmond et al. |
| 8,293,526 B2 | 10/2012 | Richmond et al. |
| 8,293,527 B2 | 10/2012 | Richmond et al. |
| 10,317,329 B2 | 6/2019 | Cairns et al. |
| 11,635,363 B2 | 4/2023 | Cairns et al. |
| 11,685,943 B2 | 6/2023 | Cairns et al. |
| 2003/0022196 A1 | 1/2003 | Lorens et al. |
| 2004/0006216 A1 | 1/2004 | Waldmann |
| 2004/0082034 A1 | 4/2004 | Lee et al. |
| 2004/0148647 A1 | 7/2004 | Enenkel et al. |
| 2004/0180378 A1 | 9/2004 | Tozer et al. |
| 2005/0005310 A1 | 1/2005 | Chisolm et al. |
| 2005/0014150 A1 | 1/2005 | Atabekov et al. |
| 2005/0059004 A1 | 3/2005 | Atabekov et al. |
| 2005/0106580 A1 | 5/2005 | Enenkel et al. |
| 2005/0250107 A1 | 11/2005 | Di Colandrea et al. |
| 2006/0141577 A1 | 6/2006 | Otte et al. |
| 2006/0172382 A1 | 8/2006 | Otte et al. |
| 2006/0188964 A1 | 8/2006 | Mancia et al. |

(Continued)

FOREIGN PATENT DOCUMENTS

| | | |
|---|---|---|
| AR | 062916 A1 | 12/2008 |
| CN | 108368504 A | 8/2018 |

(Continued)

OTHER PUBLICATIONS

Okumura, Takeshi, et al. "Efficient enrichment of high-producing recombinant Chinese hamster ovary cells for monoclonal antibody by flow cytometry." Journal of bioscience and bioengineering 120.3 (2015): 340-346. (Year: 2015).*

Mancia, Filippo, et al. "Optimization of protein production in mammalian cells with a coexpressed fluorescent marker." Structure 12.8 (2004): 1355-1360. (Year: 2004).*

Yim, Sung Sun, et al. "Rapid isolation of antibody from a synthetic human antibody library by repeated fluorescence-activated cell sorting (FACS)." PLoS one 9.10 (2014): e108225. (Year: 2014).*

Vitelli, Michael, et al. "Applications of flow cytometry sorting in the pharmaceutical industry: A review." Biotechnology Progress 37.4 (2021): e3146. (Year: 2021).*

(Continued)

*Primary Examiner* — Robert J Yamasaki

(74) *Attorney, Agent, or Firm* — Lathrop GPM LLP; James H. Velema, Esq.

(57)      ABSTRACT

Provided herein are methods and compositions for batch production of producer cells using fluorescence activated cell sorting (FACS). In some aspects, the disclosure provides a drug-selection-free method for batch production of producer cells using FACS. Such batch production methods and compositions can be further utilized to generate clonal populations of producer cells, e.g., for large-scale manufacturing of a polypeptide of interest.

23 Claims, 29 Drawing Sheets

Specification includes a Sequence Listing.

(56)                References Cited

U.S. PATENT DOCUMENTS

2007/0037254 A1    2/2007  Chisolm et al.
2007/0238122 A1   10/2007  Allbritton et al.
2008/0248468 A1   10/2008  Kubbies et al.
2009/0239235 A1    9/2009  Demaria et al.
2010/0159030 A1    6/2010  Kavallaris et al.
2013/0090259 A1    4/2013  Kotsopoulou et al.
2013/0259923 A1   10/2013  Bancel et al.
2014/0073007 A1    3/2014  Schuler et al.
2016/0177318 A1    6/2016  Assaraf et al.
2017/0121734 A1    5/2017  Cairns et al.
2017/0227441 A1    8/2017  Cairns et al.
2018/0119192 A1    5/2018  Cairns et al.
2020/0018682 A1    1/2020  Cairns et al.
2020/0299743 A1    9/2020  Cairns et al.
2024/0026410 A1    1/2024  Cairns et al.

FOREIGN PATENT DOCUMENTS

EP           1749538  A1     2/2007
EP           2064337  A2     6/2009
EP           3359665  A2     8/2018
EP           3359666  A1     8/2018
EP           3523440  A1     8/2019
WO    WO 1991/001374 A1     2/1991
WO    WO 1994/026087 A2    11/1994
WO    WO 1995/027071 A2    10/1995
WO    WO 2001/004306 A1     1/2001
WO    WO 2001/057212 A1     8/2001
WO    WO 2003/099996 A2    12/2003
WO    WO 2004/009823 A1     1/2004
WO    WO 2004/060910 A2     7/2004
WO    WO 2005/000888 A2     1/2005
WO    WO 2005/094886 A1    10/2005
WO    WO 2008/036255 A2     3/2008
WO    WO 2012/001073 A2     1/2012
WO    WO 2014/141037 A1     9/2014
WO    WO 2017/062722 A2     4/2017
WO    WO 2017/062724 A1     4/2017

OTHER PUBLICATIONS

Bailey et al. (2002) "High-Throughput Clonal Selectio of Recombinant CHO Cells Using a Dominant Selectable and Amplifiable Metallothionein-GFP Fusion Protein," Biotech. Bioeng. 80(6):670-676.
Barka et al. (2004) "Production of Cell Lines Secreting TAT Fusion Proteins," J. Histochem. and Cytochem., 52(4):469-477.
Barnes et al. (2003) "Stability of Protein Production from Recombinant Mammalian Cells," Biotech. Bioeng. 81(6):631-639.
Bohm et al. (2004) "Screening for Improved Cell Performance: Selection of Subelones with Altered Production Kinetics or Improved Stability by Cell Sorting," Biotechnol. Bioeng. 88(6):699-706.
Borth et al. (2000) "Efficient Selection of High-Producing Subelones During Gene Amplification of Recombinant Chinese Hamster Ovary Cells by Flow Cytometry and Cell Sorting," Biotechnol. Bioeng. 71(4):266-273.
Brezinsky et al. (2003) "A Simple Method for Enriching Populations of Transfected CHO Cells for Cells of Higher Specific Productivity," J. Immunol. Methods 277:141-155.
Browne et al. (2007) "Selection methods for high-producing mammalian cell lines," Trends in Biotechnology. 25(9):425-432.
Cairns et al. (2011) "Utilization of non-AUG initiation codons in a flow cytometric method for efficient selection of recombinant cell lines," Biotechnol. Bioeng. 108(11):2611-2622.
Carroll et al. (1993) "Translation of equine infectious anemia virus bicistronic tat-rev mRNA requires leaky ribosome scanning of the tat CTG initiation codon," J. Virol. 67(3):1433-1440.
Carroll et al. (2004) "The Selection of High-Producing Cell Lines Using Flow Cytometry and Cell Sorting", Expi. Opin. Biol. Ther. 4(11):1821-1829.
Chen et al. (2004) "Highly Efficient Selection of the Stable Clones Expressing Antibody-IL-2 Fusion Protein by a Dicistronic Expression Vector Containing a Mutant Neo Gene," J. Immunol. Methods. 295:49-56.

Chilov et al. (2004) "Toward construction of a self-sustained clock-like expression system based on the mammalian circadian clock," Biotechnology and Bioengineering. 87(2):234-242.
Choe et al. (2005) "A Dual-Fluorescence Reporter System for High-Throughput Clone Characterization and Selection by Cell Sorting," Nucleic Acids Res. 33(5):1-7.
Clontech Laboratories, Inc. (Sep. 1, 2005) "pIRES Vector Information," Protocol No. PT3266-5. Version No. PR59976.
Condon et al. (2003) "Development of A Chinese Hamster Ovary Cell Line for Recombinant Adenovirus-Mediated Gene Expression," Biotechnol. Prog. 19(1):137-143.
Davies et al. (1992) "The Sequence Context of the Initiation Codon in the Encephalomyocarditis Virus Leader Modulates Efficiency of Internal Translation Initiation," J. Virology 66(4):1924-1932.
DeMaria (2012) "Selection of High Expressing Mammalian Cells by Surface Display of Reporters," Ch. 3 In; Methods in Molecular Biology. 801:27-39.
DeMaria et al. (2007) "Accelerated Clone Selection for Recombinant CHO Cells Using a FACS-Based High-Throughput Screen," Biotechnology Progress. 23(2):465-472.
Domagala, et al., "CD52 Antigen—A Review", Medical Science Monitor, 2001, 7(2):325-331.
Dorn et al. (1990) "Equine infectious anemia virus tat: insights into the structure, function, and evolution of lentivirus trans-activator proteins," Journal of Virology. 64(4):1616-1624.
Drapeau et al. (1994) "Extracellular insulin degrading activity creates instability in a CHO-based batch-refeed continuous process," Cytotechnology. 15:103-109.
Edwards et al. (2004) "Flow Cytometry For High-Throughput, I ligh Content Screening", Curr. Opin. Chem. Biol. 8:392-398.
Examination Report corresponding to European Patent Application No. 07838397.3, dated Jul. 22, 2009.
Examination Report corresponding to European Patent Application No. 07838397.3, dated Jul. 7, 2011.
Fan, "Plasmid 101-Multicistronic Vectors", AddGene, Webpage, Sep. 9, 2014.
Fletcher et al. (1992) "New monoclonal antibodies in CD59: use for the analysis of peripheral blood cells from paroxysmal nocturnal haemoglobinuria (PNH) patients and for the quantitation of CD59 on normal and decay accelerating factor (DAF)-deficient erythrocytes," Immunology. 75:507-512.
Fux et al. (2004) "New-generation multicistronic expression platform: pTrident vectors containing size-optimized Ires elements enable homing endonuclease-based cistron swapping into lentiviral expression vectors," Biotechnology and Bioengineering. 86(2):174-187.
Gaines et al. (1999) "pIRES-CD4t, a Dicistronic Expression Vector for MACS- or FACS-Based Selection of Transfected Cells," BioTechniques. 26(4):683-688.
Genbank Database [Online] (Jan. 30, 2011) "Homo sapiens CD4 molecule, transcript variant 1, mRNA," Accession No. NM_000616. Accessible on the Internet at URL: http://www.ncbi.nlm.nih.gov/nuccore/NM_000616.4. [Last Accessed Feb. 9, 2011).
Gupta et al. (1988) "ACG, the initiator codon for a Sendai virus protein," Journal of Biological Chemistry. 263 (18):8553-8556.
Gurtu et al. (1996) "IRES Bicistronic Expression Vectors for Efficient Creation of Stable Mammalian Cell Lines," Biochem. Biophys. Res. Comm. 229(1):295-298.
Helman et al. (Jun. 13, 2016) "Novel membrane-bound reporter molecule for sorting high producer cells by flow cytometry," Cytometry: Part A. 85(2):162-168.
Hwang et al. (1998) "Involvement of the 5' proximal coding sequences of hepatitis C virus with internal initiation of viral translation," Biochemical and Biophysical Research Communications. 252(2):455-460.
International Preliminary Report on Patentability corresponding to International Patent Application No. PCT/US2007/020180, issued Mar. 24, 2009.
International Search Report with Written Opinion corresponding to International Patent Application No. PCT/US2007/020180, mailed May 29, 2008.

(56) References Cited

OTHER PUBLICATIONS

International Search Report with Written Opinion corresponding to International Patent Application No. PCT/US2016/055915, mailed Apr. 6, 2017.

International Search Report with Written Opinion corresponding to International Patent Application No. PCT/US2016/055918, mailed Jan. 26, 2017.

International Search Report with Written Opinion corresponding to International Patent Application No. PCT/US2017/055583, mailed Dec. 15, 2017.

Jang et al. (1989) "Initiation of Protein Synthesis by Internal Entry of Ribosomes into the 5' Nontranslated Region of Encephalomyocarditis Virus RNA In Vivo," J. Virol. 63(4):1651-1660.

Jang et al. (1998) "A Segment of the 5' Nontranslated Region of Encephalomyocarditis Virus RNA Directs Internal Entry of Ribosomes During In Vitro Translation," J. Virol. 62(8):2636-2643.

Jiang et al. (2006) "Regulation of Recombinant Monoclonal Antibody Production in Chinese Hamster Ovary Cells: A Comparative Study of Gene Copy Number, mRNA Level, and Protein Expression," Biotechnol. Prog. 22:313-318.

Kaufman et al. (1990) "Selection and Coamplification of Heterologous Genes in Mammalian Cells", Methods in Enzymology, 185: 537-566.

Keen et al. (1995) "Development of a serum-free culture medium for the large scale production of recombinant protein from a Chinese hamster ovary cell line," Cytotechnology. 17:153-163.

Kim et al. (1998) "Characterization of Chimeric Antibody Producing CHO Cells in The Course 0 Dihydrofolate Reductase-Mediated Gene Amplification and Their Stability in The Absence 0 Selective Pressure," Biotechnol. Bioeng. 58(1):73-84.

Kim et al. (1998) "Clonal Variability Within Dihydrofolate Reductase-Mediated Gene Amplified Chinese Hamster Ovary Cells: Stability in the Absence of Selective Pressure," Biotech. Bioeng. 60(6):679-688.

Kito et al. (2002) "Construction of Engineered CHO Strains for High-Level Production 0 Recombinant Proteins," Appl. Microbial. Biotechnol. 60:442-448.

Klucher et al. (1997) "A Novel Method to Isolate Cells with Conditional Gene Expression Using Fluorescence Activated Cell Sorting (FACS)," Nucleic Acids Res. 25(23):4858-4860.

Knapp et al. (2003) "Detection of 13-Lactamase Reporter Gene Expression by Flow Cytometry," Cytometry. 51A:68-78.

Koller et al. (2001) "A High-Throughput Alphavirus-Based Expression Cloning System for Mammalian Cells," Nat. Biotechnol. 19:851-855.

Kotarsky et al. (2001) "A Chimeric Reporter Gene Allowing for Clone Selection and High-Throughput Screening of Reporter Cell Lines Expressing G-Protein-Coupled Receptors," Anal. Biochern. 288:209-215.

Kozak (1989) "Context effects and inefficient initiation at non-AUG codons in eucaryotic cell-free translation systems," Mol. Cell. Biol. 9(11):5073-5080.

Kozak (1990) "Downstream secondary structure facilitates recognition of initiator codons by eukaryotic ribosomes," Proc. Natl. Acad. Sci. USA. 87:8301-8305.

Kozak (1991) "An analysis of vertebrate mRNA sequences: intimations of translational control," The Journal of Cell Biology. 115(4):887-903.

Liu et al. (2000) "Generation of Mammalian Cells Stably Expressing Multiple Genes at Predetermined Levels," Analytical Biochemistry. 280:20-28.

Medin et al. (1996) "A Bicistronic Therapeutic Retroviral Vector Enables Sorting of Transduced CD34+ Cells and Corrects the Enzyme Deficiency in Cells from Gaucher Patients," Blood. 87:1754-1762.

Mehdi et al. (1990) "Initiation of Translation at CUG, GUG, and ACG Codones in Mammalian Cells," Gene. 91:173-178.

Meng et al. (2000) "Green Fluorescent Protein as a Second Selectable Marker for Selection of High Producing Clones from Transfected CHO Cells," Gene. 242:201-207.

Mizuguchi et al. (2000) "IRES-Dependent Second Gene Expression is Significantly Lower Thank Cap-Dependent First Gene Expression in a Bicistronic Vector," Mol. Ther. 1(4):376-382.

Mizushima et al. (1990) "pEF-BOS, a powerful mammalian expression vector," Nucleic Acids Research. 18(17):5322.

Mortensen et al. (2009) "Selection of Transfected Mammalian Cells," Ch. 9. Unit 9.5 In; Curr. Protoc. Mol. Biol. pp. 9.5.1-9.5.13.

Moser et al. (2000) "An Update of pTrident Multicistronic Expression Vectors: pTridents Containing Novel Streptogramin-Responsive Promoters," Biotechnol. Prog. 16:724-735.

Mosser et al. (1997) "Use of a Dicistronic Expression Cassette Encoding the Green Fluorescent Protein for the Screening and Selection of Cells Expressing Inducible Gene Products," BioTechniques. 22:150-161.

Pelletier et al. (1988) "Internal Initiation of Translation of Eukaryotic mRNA Directed by a Sequence Derived from Poliovirus RNA," Nature. 334:320-325.

Pestova (1998) "A Prokaryotic-like Mode of Cytoplasmic Eukaryotic Ribosome Binding to the Initiation Codon During Internal Translation Initation of Hepatitis C and Classical Swine Fever Virus? RNAs," Genes and Development. 12:67-83.

Pu et al. (1998) "Rapid Establishment of High-Producing Cell Lines Using Discistronic Vectors With Glutamine Synthetase as The Selection Marker," Mol. Biotechnol. 10:17-25.

Rakestraw et al. (2006) "A Flow Cytometric Assay for Screening Improved Heterologous Protein Secretion in Yeast," Biotech. Prog. 22(4):1200-1208.

Ramesh et al. (1996) "High-Titer Bicistronic Retroviral Vectors Employing Foot-and-Mouth Disease Virus Internal Ribosomes Entry Site," Nucleic Acids Research. 24(14):2697-2700.

Rees et al. (1996) "Bicistronic Vector for the Creation of Stable Mammalian Cell Lines that Predisposes all Antibiotic-Resistant Cells to Express Recombinant Protein," Biotechniques. 20:102-110.

Sato et al. (Dec. 5, 2014) "A combination of targeted toxin technology and the piggyBac-mediated gene transfer system enables efficient isolation of stable transfectants in nonhuman mammalian cells," Biotechnol. J. 10(1):143-153.

Sato et al. (Mar. 2013) "Targeted Toxin-Based Selectable Drug-Free Enrichment of Mammalian Cells with High Transgene Expression," Biology. 2(1):341-355.

Sautter et al. (2005) "Selection of High-Producing CHO Cells Using NPT Selection marker with Reduced Enzyme Activity," Biotech. Bioeng. 89(5):530-538.

Scharfenberg et al. (1995) "A Reliable Strategy for The Achievement of Cell Lines Growing in Protein-Free Medium," In; Animal Cell Technology: Developments Towards the 21st Century. Eds.: Beuvery et al. pp. 619-623.

Schlatter et al. (2001) "Novel surface tagging technology for selection of complex proliferation-controlled mammalian cell phenotypes," Biotechnology and Bioengineering. 75(5):597-606.

Schlatter et al. (2005) "On the Optimal Ratio of Heavy to Light Chain Genes for Efficient Recombinant Antibody Production by CHO Cells," Biotech Prog. 21:122-133.

Schubert et al. (1999) "Regulation of Virus Release by the Macrophage-Tropic Human Immunodeficiency Virus Type 1 AD8 Isolate is Redundant and can be Controlled by either Vpu or Env," Journal of Virology. 73(2):887-896.

Sen et al. (1990) "Flow Cytometric Study of Hybridoma Cell Culture: Correlation Between Cell Surface Fluorescence and IgG Production Rate," Enzyme Microb. Technol. 12:571-576.

Soriano et al. (2002) "Optimization of Recombinant Protein Expression Level in Eseherichia coli by Flow Cytometry and Cell Sorting," Biotechnol. Bioeng. 80(1):93-99.

Tsai et al. (2002) "Evidence for translational regulation of the imprinted Snurf-Snrpn locus in mice," Human Molecular Genetics. 11(14):1659-1668.

Urlaub et al. (1980) "Isolation of Chinese Hamster Cell Mutants Deficient in Dihydrofolate Reductase Activity," Proc. Natl. Acad. Sci. USA. 77(7):4216-4220.

Yoshikawa et al. (2001) "Flow Cytometry: An Improved Method for the Selection of Highly Productive Gene-Amplified CHO Cells Using Flow Cytometry," Biotechnol. Bioeng. 74(5):435-442.

(56)          References Cited

OTHER PUBLICATIONS

Yuk et al. (2002) "A GFP-Based Screen for Growth-Arrested, Recombinant Protein-Producing Cells," Biotechnol. Bioeng. 79(1):74-82.

Zeyda et al. (1999) "Optimization of Sorting Conditions for the Selection of Stable, High-Producing Mammalian Cell Lines," Biotechnol. Prog. 15:953-957.

Zlokarnik et al. (1998) "Quantitation of Transcription and Clonal Selection of Single Living Cells With 13-Lactamase as Reporter," Science. 279:84-88.

U.S. Appl. No. 12/441,806 2009/0239235, filed Mar. 18, 2009 Sep. 24, 2009, Christine DeMaria, Facs- and Reporter Protein-Based System for High Throughput Development of Therapeutic Proteins.

U.S. Appl. No. 15/288,036 2017/0227441 U.S. Pat. No. 11,635,363, filed Oct. 7, 2016 Aug. 10, 2017 Apr. 25, 2023, Victor R. Cairns, Flare (Flow Cytometry Attenuated Reporter Expression) Technology for Rapid Bulk Sorting.

2023/0304913, Mar. 10, 2023 Sep. 28, 2023, Victor R. Cairns, Flare (Flow Cytometry Attenuated Reporter Expression) Technology for Rapid Bulk Sorting.

U.S. Appl. No. 15/288,050 2017/0121734 U.S. Pat. No. 10,317,329, filed Oct. 7, 2016 May 4, 2017 Jun. 11, 2019, Victor R. Cairns, Flare (Flow Cytometry Attenuted Reporter Expression) Technology for Rapid Bulk Sorting.

U.S. Appl. No. 16/392,174 2020/0018682, filed Apr. 23, 2019 Jan. 16, 2020, Victor R. Cairns, Early Post-Transfection Isolation of Cells (Epic) for Biologics Production.

U.S. Appl. No. 15/727,272 2018/0119192, filed Oct. 6, 2017 May 3, 2018, Victor R. Cairns, Early-Post Transfection Isolation of Cells (Epic) for Biologics Production.

U.S. Appl. No. 16/683,837 2020/0299743 U.S. Pat. No. 11,685,943, filed Nov. 14, 2019 Sep. 24, 2020 Jun. 27, 2023, Victor R. Cairns, Early Port-Transfection Isolation of Cells (Epic) for Biologics Production.

U.S. Appl. No. 18/315,332 2024/0026410, filed May 10, 2023 Jan. 25, 2024, Victor R. Cairns, Early Post-Transfection Isolation of Cells (Epic) for Biologics Production.

* cited by examiner

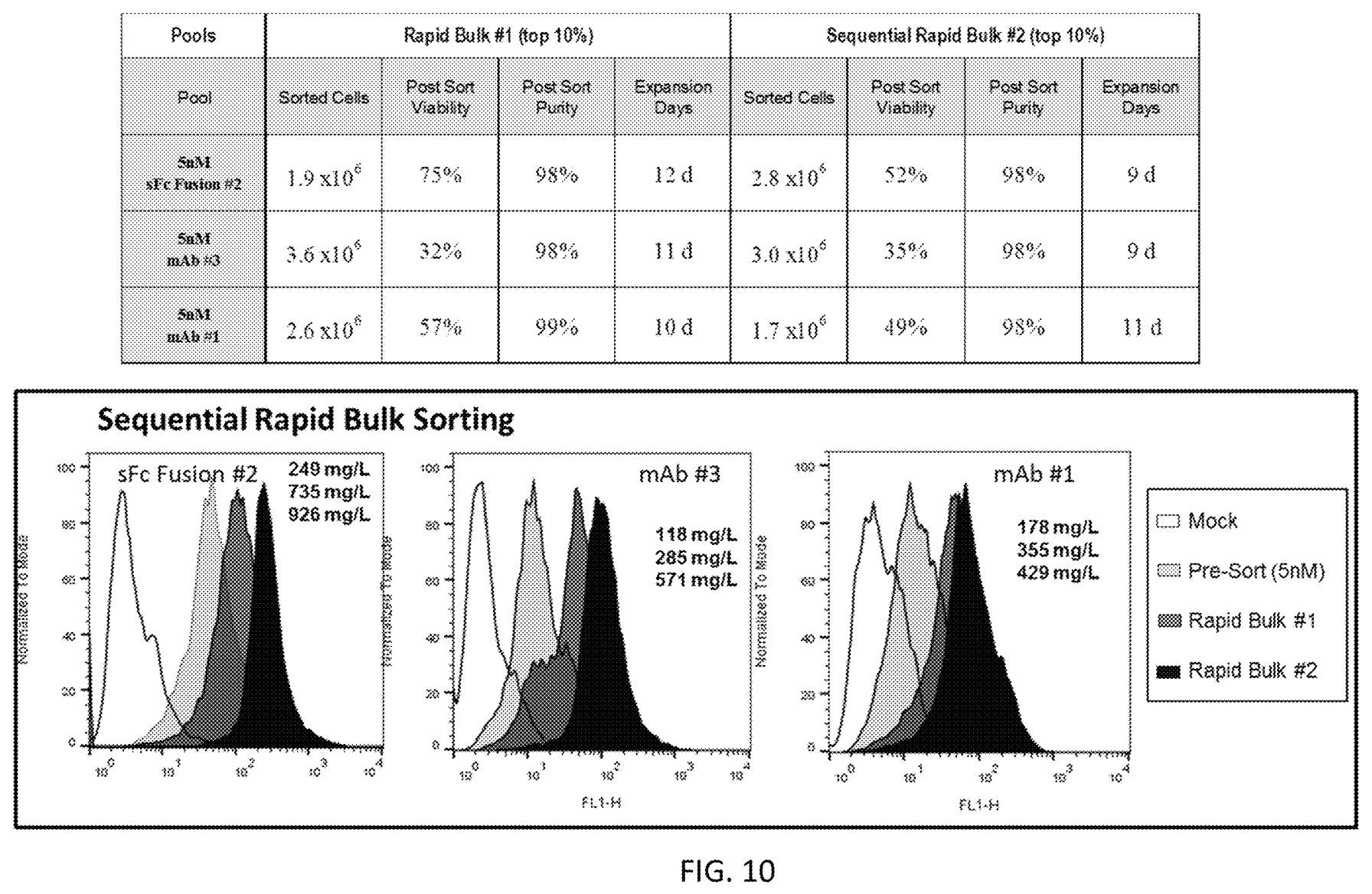

| Pools | Rapid Bulk #1 (top 10%) | | | | Sequential Rapid Bulk #2 (top 10%) | | | |
|---|---|---|---|---|---|---|---|---|
| Pool | Sorted Cells | Post Sort Viability | Post Sort Purity | Expansion Days | Sorted Cells | Post Sort Viability | Post Sort Purity | Expansion Days |
| 5aM sFc-Fusion #2 | 1.9 x10⁶ | 75% | 98% | 12 d | 2.8 x10⁶ | 52% | 98% | 9 d |
| 5aM mAb-3 | 3.6 x10⁶ | 32% | 98% | 11 d | 3.0 x10⁶ | 35% | 98% | 9 d |
| 5aM mAb #1 | 2.6 x10⁶ | 57% | 99% | 10 d | 1.7 x10⁶ | 49% | 98% | 11 d |

FIG. 10

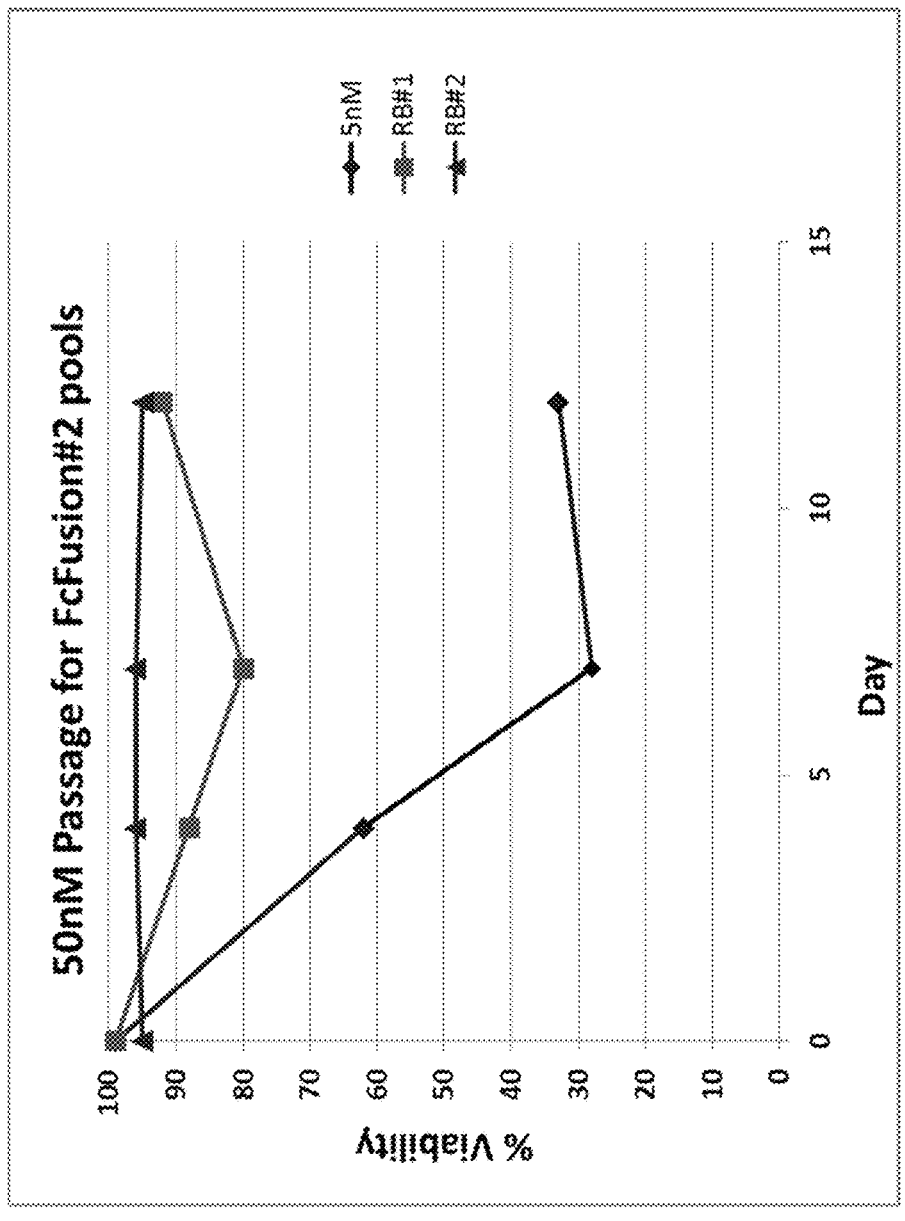
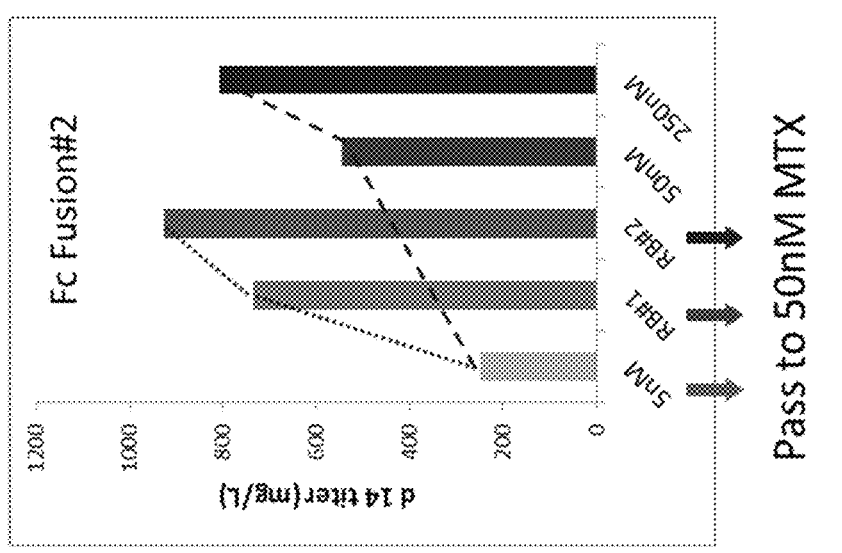
FIG. 12

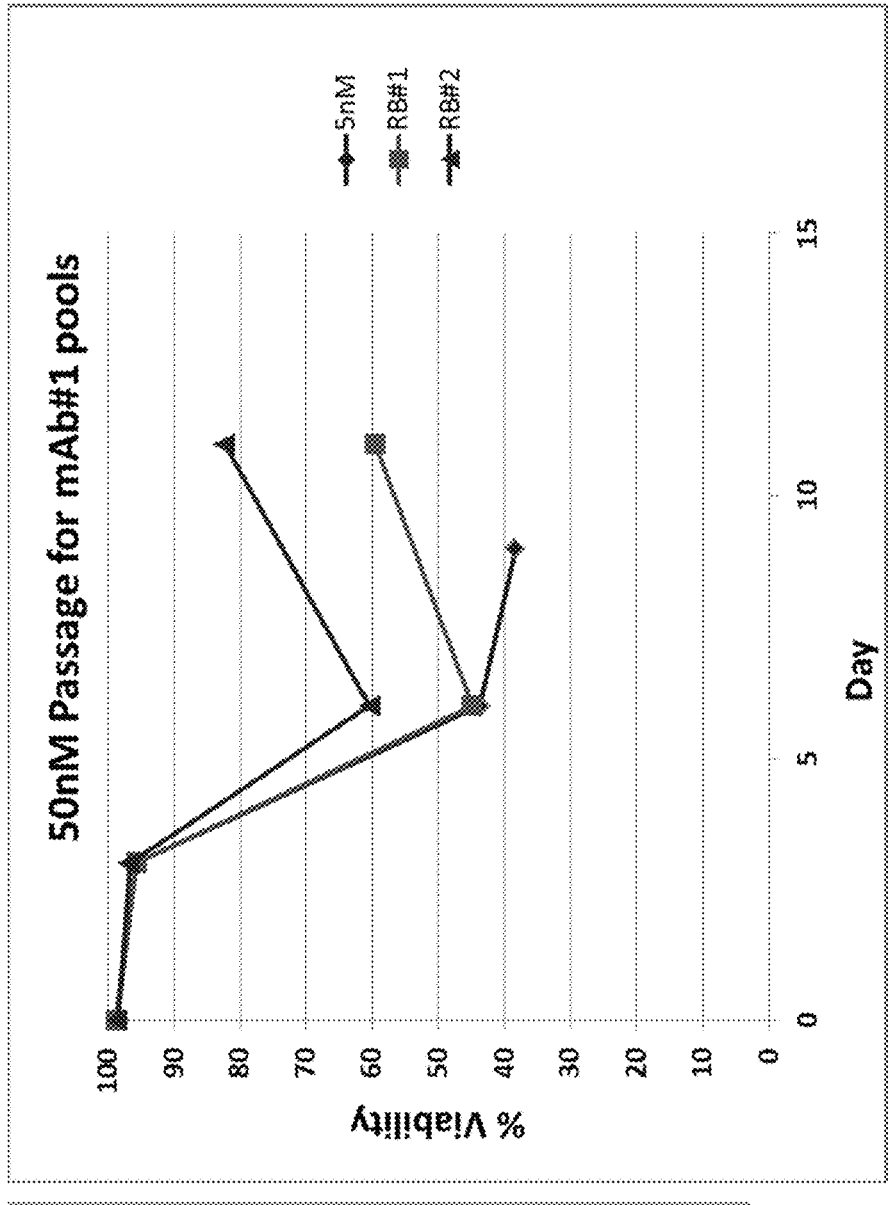
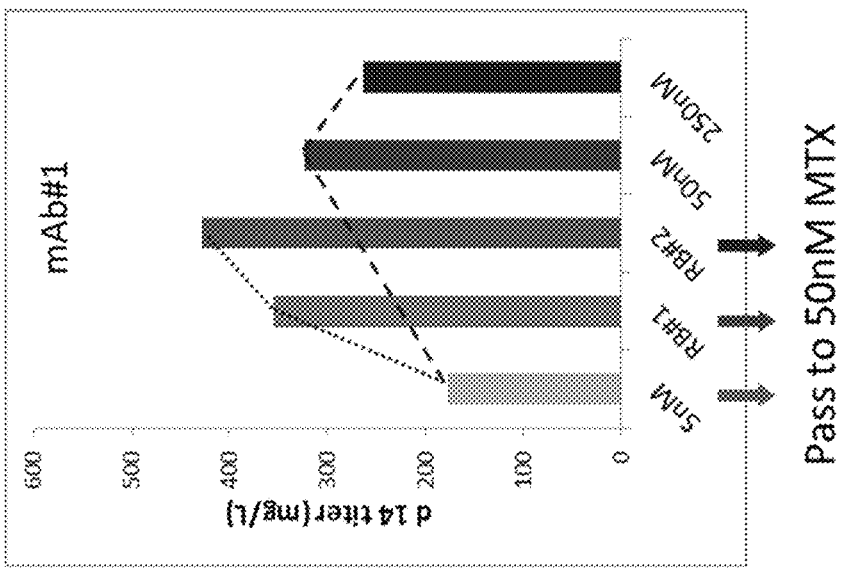
FIG. 14

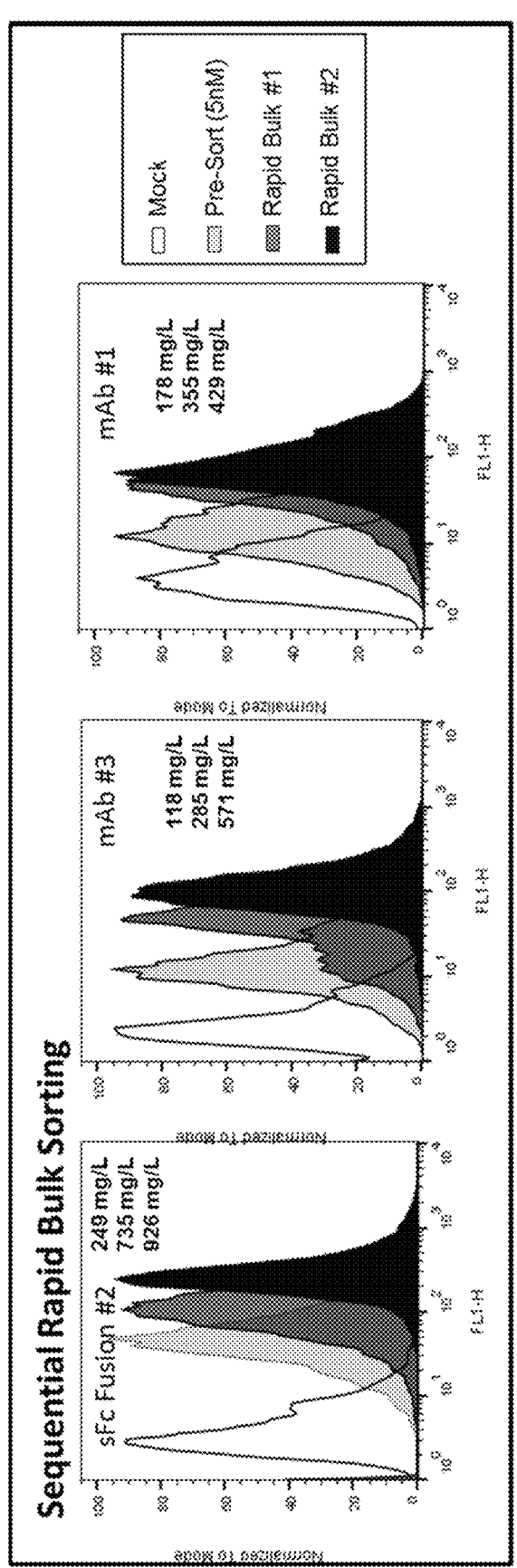
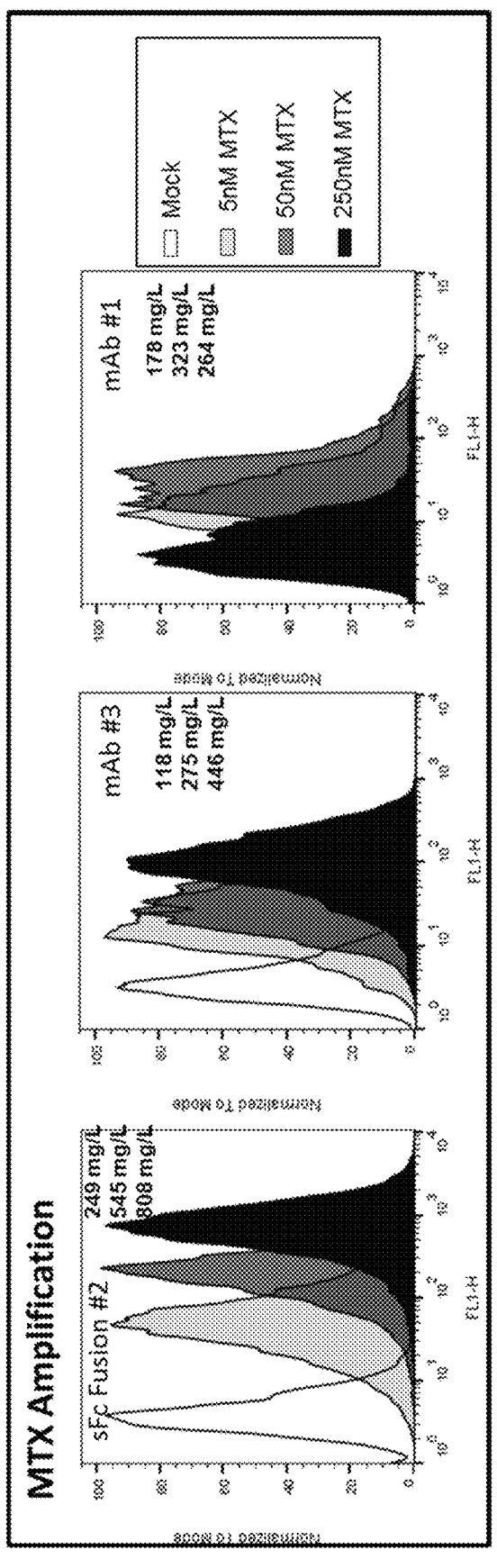
FIG. 15 sFcR #2 (pools #1 & #2)

| | Pools | | Clones | | | | | | |
|---|---|---|---|---|---|---|---|---|---|
| SortID | Pre-sort titer (batch in 30%EF-B)* | | group ID | # FACS screened | Cloning Efficiency | # selected for expansion | # terminal batch setup (to-date) | clone survivability | Top titer (batch in 30%EF-B)* |
| Sort 1 (20nM pool 4) (6) 96 well plates | 0.20 g/L | | A | 56 | 9.8% | 26 | 15 | 58% | 1.8 g/L |
| Sort 2 (100nM pool 2) (6) 96 well plates | 0.30 g/L | | B | 67 | 11.8% | 33 | 0 | 0% | NA |
| Sort 3 (RB#2 pool 4) (6) 96 well plates | 0.64 g/L | | C | 98 | 17.2% | 48 | 41 | 85% | 2.3 g/L |
| Sequential Sort 10% bulk → 10% ACDU plated = 1692 | | | | 221 | 13.1% | 107 | 56 | 52.3% | |

* d14 titers from unfed batch with CDCHO w 30%EF-B

FIG. 18

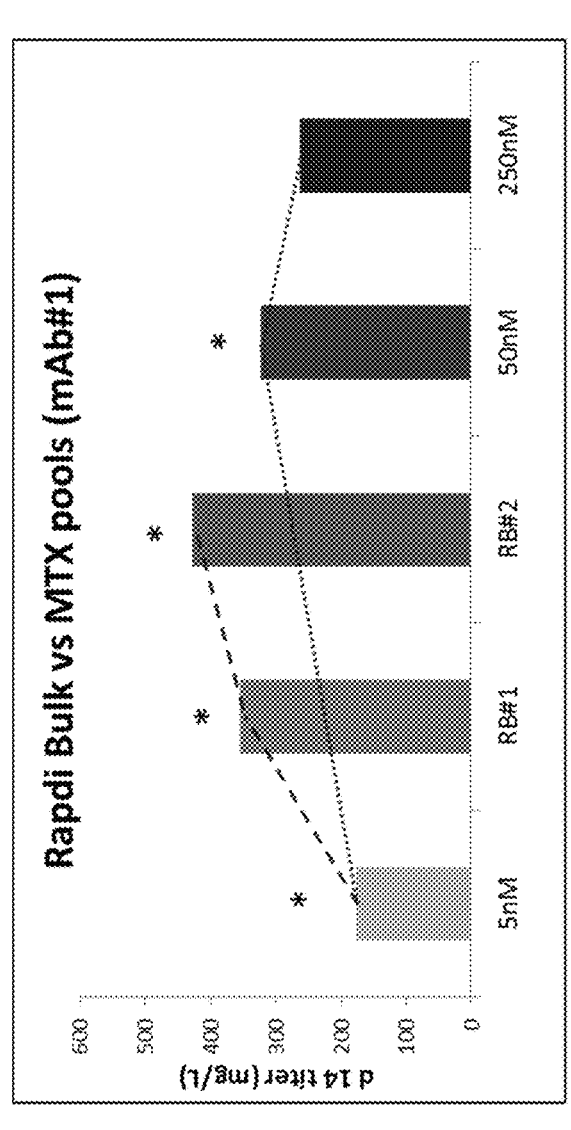
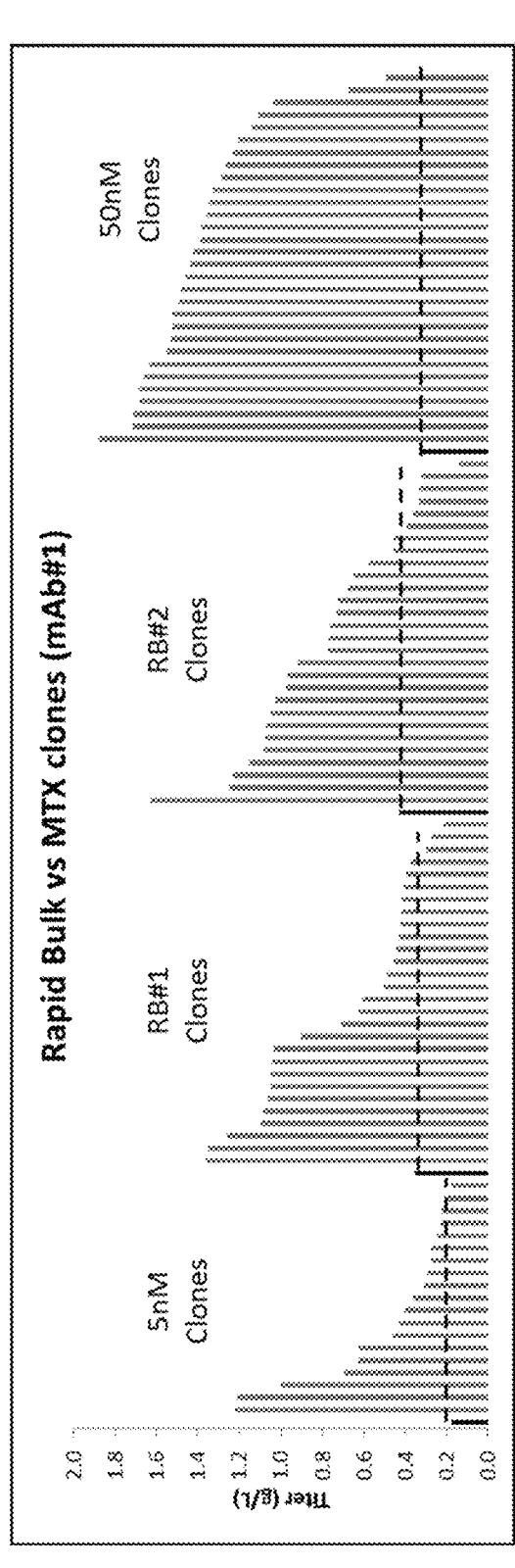
FIG. 22

FLARE (FLOW CYTOMETRY ATTENUATED REPORTER EXPRESSION) TECHNOLOGY FOR RAPID BULK SORTING

RELATED APPLICATIONS

This application is a division of U.S. patent application Ser. No. 15/288,036, filed Oct. 7, 2016, now U.S. Pat. No. 11,635,363, which claims the benefit to U.S. Provisional Patent Application Ser. No. 62/239,515, filed Oct. 9, 2015. The contents of the aforementioned applications are hereby incorporated herein by reference in their entirety.

SEQUENCE LISTING

The instant application contains a Sequence Listing which has been submitted electronically in XML format and is hereby incorporated by reference in its entirety. Said XML file, created on Mar. 10, 2023, is named 740608 SA9-179CON_ST26.xml, and is 20,483 bytes in size.

BACKGROUND

Methods for selection of producer cell populations and cell clones are imperative for the manufacturing of biologics, such as antibodies and fusion proteins. Such methods generally rely on use of a selection agent, such as methotrexate (MTX) or methionine sulphoximine (MSX), to bias and amplify the production of biologics. Selection agent-based methods may affect the viability or growth rate of selected populations or may have a negative impact on clonal stability. Such drug based selections can also be time consuming, often requiring multiple rounds of selection to obtain populations which contain clones that are suitable for biologic manufacturing. There remains a need for rapid and reliable methods of generating both large cell populations and clones that produce high titers of biologics with less negative impact to the host cell.

SUMMARY OF THE INVENTION

In some aspects, the disclosure provides methods of batch selection and clonal selection of producer cells. As described herein, methods for batch selection were developed that relied upon rapid bulk sorting of heterogeneous populations of producer cells using fluorescence activated cell sorting (FACS) without the use of MTX as an amplification agent. The methods described herein were surprisingly found to be both faster and more productive than traditional MTX amplification. The methods described herein are useful, e.g., for the generation of productive pools of producer cells for screening of polypeptides of interest (such as in early clinical development) and for the generation of high titer clones, which can be utilized to produce a polypeptide of interest both for small and large scale manufacturing.

Accordingly, in some aspects, the disclosure provides a method of fluorescence activated cell sorting (FACS) to batch select producer cells expressing a target polypeptide, the method comprising (a) providing a heterogeneous population of producer cells, wherein the producer cells in the population express varying levels of a FACS selectable polypeptide and a target polypeptide that are encoded by the same multicistronic mRNA, (b) selecting from the heterogeneous population of producer cells a first heterogeneous sub-population of producer cells using FACS, wherein the producer cells in the first heterogeneous sub-population express the FACS selectable polypeptide at a level that is higher than the level of at least 80% of the producer cells in the heterogeneous population in (a), and (c) expanding the first heterogeneous sub-population of producer cells in drug-selection-free medium, thereby producing an expanded first heterogeneous sub-population of producer cells.

In some embodiments, the method further comprises (d) selecting from the expanded first heterogeneous sub-population of producer cells in (c) a second heterogeneous sub-population of producer cells using FACS, wherein the producer cells in the second sub-population express the FACS selectable polypeptide at a level that is higher than the level of at least 80% of the producer cells in the expanded first heterogeneous sub-population of producer cells in (c), and (e) expanding the second heterogeneous sub-population of producer cells in a drug-selection-free medium, thereby producing an expanded second heterogeneous sub-population of producer cells.

In some embodiments of any one of the methods provided, the method further comprises isolating the target polypeptide from the expanded first or second heterogeneous sub-population. In some embodiments of any one of the methods provided, the method further comprises isolating one or more single producer cells from the expanded first or second heterogeneous sub-population and individually culturing the one or more single producer cells to produce clonal populations of the one or more single producer cells. In some embodiments of any one of the methods provided, the expanded first heterogeneous sub-population of producer cells yields a 1.2- to 5-fold improvement in production of the target polypeptide compared to that of the heterogeneous population of producer cells in (a). In some embodiments of any one of the methods provided, the expanded second heterogeneous sub-population of producer cells yields a 1.2- to 2.5-fold improvement in production of the target polypeptide compared to that of the expanded first heterogeneous sub-population of producer cells in (c). In some embodiments of any one of the methods provided, at least one of the clonal populations of the one or more single cells yields a 5- to 30-fold improvement in production of the target polypeptide compared to that of the heterogeneous population of producer cells in (a).

In some embodiments of any one of the methods provided, the heterogeneous population of producer cells subject to FACS in (b) contains $80\text{-}120 \times 10^6$ cells. In some embodiments of any one of the methods provided, the first and/or second heterogeneous sub-population of producer cells contains $0.5\text{-}6.0 \times 10^6$ cells prior to expansion in step (c) or (e).

In some embodiments of any one of the methods provided, the expanding in step c) is for between 7-14 days. In some embodiments of any one of the methods provided, the expanding in step e) is for between 7-14 days.

In some embodiments of any one of the methods provided, the drug-selection-free medium is methotrexate-free medium or methionine sulphoximine-free medium.

In some embodiments of any one of the methods provided, the heterogeneous population of producer cells in (a) is produced by transfecting cells with a vector that encodes the multicistronic mRNA and subjecting the transfected cells to one round of medium-based selection to select cells expressing varying levels of the multicistronic mRNA. In some embodiments of any one of the methods provided, the vector further contains a dihydrofolate reductase (DHFR) gene. In some embodiments of any one of the methods provided, the medium-based selection is methotrexate-containing medium or nucleotide-deficient medium.

In some embodiments of any one of the methods provided, the heterogeneous population of producer cells in (a) is produced by transfecting cells with a vector that encodes the multicistronic mRNA and subjecting the transfected cells to FACS to select cells expressing varying levels of the multicistronic mRNA. In some embodiments of any one of the methods provided, the multicistronic mRNA comprises a first open reading frame (ORF) that encodes the FACS selectable polypeptide and a second ORF that encodes the target polypeptide, wherein the first ORF is 5' to the second ORF.

In some embodiments of any one of the methods provided, the first ORF has a non-AUG start codon. In some embodiments of any one of the methods provided, the second ORF has an AUG start codon. In some embodiments of any one of the methods provided, the non-AUG start codon is a UUG, GUG or CUG in a Kozak consensus sequence. In some embodiments of any one of the methods provided, the ORF that encodes the FACS selectable polypeptide is devoid of any AUG sequences.

In some embodiments of any one of the methods provided, the FACS selectable polypeptide is CD52 or CD59. In some embodiments of any one of the methods provided, the target polypeptide is a therapeutic agent. In some embodiments of any one of the methods provided, the target polypeptide is a secreted protein. In some embodiments of any one of the methods provided, the target polypeptide is an antibody or an Fc fusion protein.

In some embodiments of any one of the methods provided, the producer cells are CHO cells, HEK293 cells, or HeLa cells.

Other aspects of the disclosure relate to a clonal population of producer cells that express a FACS selectable polypeptide and a target polypeptide obtainable by any one of the methods described above or otherwise described herein. In some embodiments, the clonal population yields a 5- to 30-fold improvement in production of the target polypeptide compared to that of the heterogeneous population of producer cells in (a).

Yet other aspects of the disclosure relate to a method of increasing viability of cells after fluorescence activated cell sorting (FACS), the method comprising using a first round of FACS to select based on a viability marker a first sub-population of cells from a population of cells expressing a target polypeptide, and using a second round of FACS to select based on the viability marker a second sub-population of cells from the first sub-population of cells, wherein the first round and second round of FACS occur within 8 hours of each other. In some embodiments, the viability marker is a forward scatter/side scatter population differentiation and/ or a propidium iodide stain. In some embodiments, the second sub-population has a post sort viability improvement of 1.2- to 4-fold compared to the initial sub-population post sort viability. In some embodiments, the method further comprises expanding the second sub-population. In some embodiments, the method further comprises individually culturing cells from the second sub-population in order to generate one or more clonal populations.

In certain embodiments, the selection in step (b) is performed between 2 to about 15 days after transfection of the heterogeneous population of producer cells with a vector encoding the multicistronic mRNA. In certain exemplary embodiments, the selection in step (b) is performed between about 2 and about 10 days, about 2 and about 6 days, about 2 and about 4 days after transfection. In one exemplary embodiment, the selection in step (b) is performed two days after transfection. In another exemplary embodiment, the selection in step (b) is performed three days after transfection.

In an exemplary aspect, the disclosure provides a method of fluorescence activated cell sorting (FACS) to batch select producer cells expressing a sFc fusion polypeptide, the method comprising (a) providing a heterogeneous population of producer cells, wherein the producer cells in the population express varying levels of a FACS selectable CD52 polypeptide and the sFc fusion polypeptide which are encoded by the same multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), and (c) expanding 1.3 million cells of the first heterogeneous sub-population of producer cells in drug-selection-free medium for seven days, thereby producing an expanded first heterogeneous sub-population of producer cells, wherein the heterogeneous population of producer cells in (a) is produced by transfecting cells with a vector that encodes the multicistronic mRNA and subjecting the transfected cells to one round of medium-based selection to select cells expressing varying levels of the multicistronic mRNA, wherein the medium-based selection is 50 nM methotrexate-containing medium, wherein the multicistronic mRNA comprises a first open reading frame (ORF) that encodes the CD52 polypeptide and a second ORF that encodes the sFc fusion polypeptide, wherein the first ORF is 5' to the second ORF, wherein the first ORF has a UUG start codon, wherein the second ORF has an AUG start codon, wherein the first ORF is devoid of any AUG sequences, and wherein the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing an IgG heavy chain polypeptide and an IgG light chain polypeptide, the method comprising (a) providing a heterogeneous population of producer cells, wherein the producer cells in the population express varying levels of a FACS selectable CD52 polypeptide and the IgG heavy chain polypeptide which are encoded by a same first multicistronic mRNA, and wherein the producer cells in the population express varying levels of a FACS selectable CD52 polypeptide and the IgG light chain polypeptide, which are encoded by a same second multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), and (c) expanding 1.3 million cells of the first heterogeneous sub-population of producer cells in drug-selection-free medium for seven days, thereby producing an expanded first heterogeneous sub-population of producer cells, wherein the heterogeneous population of producer cells in (a) is produced by transfecting cells with a first vector that encodes the first multicistronic mRNA encoding the IgG heavy chain polypeptide and a second vector that encodes the second multicistronic mRNA encoding the IgG light chain polypeptide and subjecting the transfected cells to one round of medium-based selection to select cells expressing varying levels of the multicistronic mRNAs, wherein the medium-based selection is 5 nM methotrexate-containing medium, wherein the first multicistronic mRNA comprises a first open reading frame (ORF) that encodes the CD52 polypeptide and a second ORF that encodes the IgG heavy chain polypeptide, wherein the second multicistronic mRNA comprises a first open reading frame (ORF) that encodes the CD52 polypeptide and a second ORF that encodes the IgG light chain polypeptide, wherein in each of the first and second multicistronic mRNAs: (i) the first ORF is 5' to the second ORF, (ii) the first ORF has a UUG start codon, (iii) the second ORF has an AUG start codon, (iv) the first ORF is devoid of any AUG sequences, and (v) the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing a sFc fusion polypeptide, the method comprising (a) providing a heterogeneous population of producer cells, wherein the producer cells in the population express varying levels of a FACS selectable CD52 polypeptide and the sFc fusion polypeptide which are encoded by the same multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), (c) expanding the first heterogeneous sub-population of producer cells in drug-selection-free medium for twelve days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express a CD52 polypeptide at a level that is higher than the level of at least 90% of the producer cells in the expanded first heterogeneous sub-population of producer cells in (c), and (e) expanding the second heterogeneous sub-population of producer cells in a drug-selection-free medium for nine days, thereby producing an expanded second heterogeneous sub-population of producer cells, wherein the heterogeneous population of producer cells in (a) is produced by transfecting cells with a vector that encodes the multicistronic mRNA and subjecting the transfected cells to one round of medium-based selection to select cells expressing varying levels of the multicistronic mRNA, wherein the medium-based selection is 5 nM methotrexate-containing medium, wherein the multicistronic mRNA comprises a first open reading frame (ORF) that encodes the CD52 polypeptide and a second ORF that encodes the sFc fusion polypeptide, wherein the first ORF is 5' to the second ORF, wherein the first ORF has a UUG start codon, wherein the second ORF has an AUG start codon, wherein the first ORF is devoid of any AUG sequences, and wherein the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing an IgG heavy chain polypeptide and an IgG light chain polypeptide, the method comprising (a) providing a heterogeneous population of producer cells, wherein the producer cells in the population express varying levels of a FACS selectable CD52 polypeptide and the IgG heavy chain polypeptide which are encoded by a same first multicistronic mRNA, and wherein the producer cells in the population express varying levels of a FACS selectable CD52 polypeptide and the IgG light chain polypeptide, which are encoded by a same second multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), (c) expanding the first heterogeneous sub-population of producer cells in drug-selection-free medium for eleven days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express the CD52 polypeptide at a level that is higher than the level of at least 90% of the producer cells in the expanded first heterogeneous sub-population of producer cells in (c), and (e) expanding the second heterogeneous sub-population of producer cells in a drug-selection-free medium for nine days, thereby producing an expanded second heterogeneous sub-population of producer cells, wherein the heterogeneous population of producer cells in (a) is produced by transfecting cells with a first vector that encodes the first multicistronic mRNA encoding the IgG heavy chain polypeptide and a second vector that encodes the second multicistronic mRNA encoding the IgG light chain polypeptide and subjecting the transfected cells to one round of medium-based selection to select cells expressing varying levels of the multicistronic mRNAs, wherein the medium-based selection is 5 nM methotrexate-containing medium, wherein the first multicistronic mRNA comprises a first open reading frame (ORF) that encodes the CD52 polypeptide and a second ORF that encodes the IgG heavy chain polypeptide, wherein the second multicistronic mRNA comprises a first open reading frame (ORF) that encodes the CD52 polypeptide and a second ORF that encodes the IgG light chain polypeptide, wherein in each of the first and second multicistronic mRNAs (i) the first ORF is 5' to the second ORF, (ii) the first ORF has a UUG start codon, (iii) the second ORF has an AUG start codon, (iv) the first ORF is devoid of any AUG sequences, and (v) the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing an IgG heavy chain polypeptide and an IgG light chain polypeptide, the method comprising (a) providing a heterogeneous population of producer cells, wherein the producer cells in the population express varying levels of a FACS selectable CD52 polypeptide and the IgG heavy chain polypeptide which are encoded by a same first multicistronic mRNA, and wherein the producer cells in the population express varying levels of a FACS selectable CD52 polypeptide and the IgG light chain polypeptide, which are encoded by a same second multicistronic mRNA,(b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), (c) expanding the first heterogeneous sub-population of producer cells in drug-selection-free medium for ten days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express the CD52 polypeptide at a level that is higher than the level of at least 90% of the producer cells in the expanded first heterogeneous sub-population of producer cells in (c), and (e) expanding the second heterogeneous sub-population of producer cells in a drug-selection-free medium for eleven days, thereby producing an expanded second heterogeneous sub-population of producer cells, wherein the heterogeneous population of producer cells in (a) is produced by transfecting cells with a first vector that encodes the first multicistronic mRNA encoding the IgG heavy chain polypeptide and a second vector that encodes the second multicistronic mRNA encoding the IgG light chain polypeptide and subjecting the transfected cells to one round of medium-based selection to select cells expressing varying levels of the multicistronic mRNAs, wherein the medium-based selection is 5 nM methotrexate-containing medium, wherein the first multicistronic mRNA comprises a first open reading frame (ORF) that encodes the CD52 polypeptide and a second ORF that encodes the IgG heavy chain polypeptide, wherein the second multicistronic mRNA comprises a first open reading frame (ORF) that encodes the CD52 polypeptide and a second ORF that encodes the IgG light chain polypeptide, wherein in each of the first and second multicistronic mRNAs (i) the first ORF is 5' to the second ORF, (ii) the first ORF has a UUG start codon, (iii) the second ORF has an AUG start codon, (iv) the first ORF is devoid of any AUG sequences, and (v) the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing an IgG heavy chain polypeptide and an IgG light chain polypeptide, the method comprising (a) providing a heterogeneous population of producer cells, wherein the producer cells in the population express varying levels of a FACS selectable CD52 polypeptide and the IgG heavy chain polypeptide which are encoded by a same first multicistronic mRNA, and wherein the producer cells in the population express varying levels of a FACS selectable CD52 polypeptide and the IgG light chain polypeptide, which are encoded by a same second multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), and
(c) expanding the first heterogeneous sub-population of producer cells in drug-selection-free medium for ten days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express the CD52 polypeptide at a level that is higher than the level of at least 90% of the producer cells in the expanded first heterogeneous sub-population of producer cells in (c), (e) expanding the second heterogeneous sub-population of producer cells in a drug-selection-free medium for eleven days, thereby producing an expanded second heterogeneous sub-population of producer cells, and (f) isolating single producer cells from the expanded first or second heterogeneous sub-population and individually culturing the single producer cells to produce clonal populations of the single producer cells, wherein the isolated single producer cells express the CD52 polypeptide at a level that is higher than the level of 97-99% of single producer cells, wherein the heterogeneous population of producer cells in (a) is produced by transfecting cells with a first vector that encodes the first multicistronic mRNA encoding the IgG heavy chain polypeptide and a second vector that encodes the second multicistronic mRNA encoding the IgG light chain polypeptide and subjecting the transfected cells to one round of medium-based selection to select cells expressing varying levels of the multicistronic mRNAs, wherein the medium-based selection is 5 nM methotrexate-containing medium, wherein the first multicistronic mRNA comprises a first open reading frame (ORF) that encodes the CD52 polypeptide and a second ORF that encodes the IgG heavy chain polypeptide, wherein the second multicistronic mRNA comprises a first open reading frame (ORF) that encodes the CD52 polypeptide and a second ORF that encodes the IgG light chain polypeptide, wherein in each of the first and second multicistronic mRNAs (i) the first ORF is 5' to the second ORF, (ii) the first ORF has a UUG start codon, (iii) the second ORF has an AUG start codon, (iv) the first ORF is devoid of any AUG sequences, and (v) the multicistronic mRNA is in an expression vector which further comprises a dihydrofolate reductase (DHFR) cassette.

In another exemplary aspect the disclosure provides a method of fluorescence activated cell sorting (FACS) to batch select producer cells expressing a sFc fusion polypeptide, the method comprising (a) providing a heterogeneous population of producer cells, wherein the producer cells in the population express varying levels of a FACS selectable CD52 polypeptide and the sFc fusion polypeptide which are encoded by the same multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), (c) expanding the first heterogeneous sub-population of $3\text{-}4 \times 10^6$ producer cells in drug-selection-free medium for eight days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express the CD52 polypeptide at a level that is higher than the level of at least 90% of the producer cells in the expanded first heterogeneous sub-population of producer cells in (c), and (e) expanding the second heterogeneous sub-population of $3\text{-}4 \times 10^6$ producer cells in a drug-selection-free medium for eight days, thereby producing an expanded second heterogeneous sub-population of producer cells, wherein the heterogeneous population of producer cells in (a) is produced by transfecting cells with a vector that encodes the multicistronic mRNA and subjecting the transfected cells to one round of medium-based selection to select cells expressing varying levels of the multicistronic mRNA, wherein the medium-based selection is nucleotide deficient medium supplemented with glutamine and 5 nM methotrexate, wherein the multicistronic mRNA comprises a first open reading frame (ORF) that encodes the CD52 polypeptide and a second ORF that encodes the sFc fusion polypeptide, wherein the first ORF is 5' to the second ORF, wherein the first ORF has a UUG start codon, wherein the second ORF has an AUG start codon, wherein the first ORF is devoid of any AUG sequences, and wherein the multicistronic mRNA is in an expression vector which further comprises a dihydrofolate reductase (DHFR) cassette.

In another exemplary aspect, the disclosure provides a method of fluorescence activated cell sorting (FACS) to batch select producer cells expressing a sFc fusion polypeptide, the method comprising (a) providing a heterogeneous population of producer cells, wherein the producer cells in the population express varying levels of a FACS selectable CD52 polypeptide and the sFc fusion polypeptide which are encoded by the same multicistronic mRNA, (b) selecting from the heterogeneous population of producer cells a first heterogeneous sub-population of producer cells using FACS, wherein the producer cells in the first heterogeneous sub-population express the CD52 polypeptide at a level that is higher than the level of 90% of the producer cells in the heterogeneous population in (a), (c) expanding the first heterogeneous sub-population of 3-4×10^6 producer cells in drug-selection-free medium for eight days, thereby producing an expanded first heterogeneous sub-population of producer cells, (d) selecting from the expanded first heterogeneous sub-population of producer cells in (c) a second heterogeneous sub-population of producer cells using FACS, wherein the producer cells in the second sub-population express the CD52 polypeptide at a level that is higher than the level of at least 90% of the producer cells in the expanded first heterogeneous sub-population of producer cells in (c), (e) expanding the second heterogeneous sub-population of 3-4×10^6 producer cells in a drug-selection-free medium for eight days, thereby producing an expanded second heterogeneous sub-population of producer cells, and (f) isolating single producer cells from the expanded first or second heterogeneous sub-population and individually culturing the single producer cells to produce clonal populations of the single producer cells, wherein the isolated single producer cells express the CD52 polypeptide at a level that is higher than the level of 99% of single producer cells, wherein the heterogeneous population of producer cells in (a) is produced by transfecting cells with a vector that encodes the multicistronic mRNA and subjecting the transfected cells to one round of medium-based selection to select cells expressing varying levels of the multicistronic mRNA, wherein the medium-based selection is nucleotide deficient medium supplemented with glutamine and 5 nM methotrexate, wherein the multicistronic mRNA comprises a first open reading frame (ORF) that encodes the CD52 polypeptide and a second ORF that encodes the sFc fusion polypeptide, wherein the first ORF is 5' to the second ORF, wherein the first ORF has a UUG start codon, wherein the second ORF has an AUG start codon, wherein the first ORF is devoid of any AUG sequences, and wherein the multicistronic mRNA is in an expression vector which further comprises a dihydrofolate reductase (DHFR) cassette.

BRIEF DESCRIPTION OF THE DRAWINGS

FIG. 10 is a table and a series of diagrams of flow cytometry data showing sequential top 10% rapid bulk sorting of cells expressing Fc fusion protein (sFcFusion #2) or monoclonal antibodies (mAb #3 or mAb #1).
FIG. 12 is two graphs, the left graph showing the 14 day titer of an Fc Fusion protein and the right graph showing % viability of cells expressing the Fc Fusion protein, which had been generated by rapid bulk sorting or 5 nM MTX selection, after passage with 50 nM MTX.).
FIG. 14 is two graphs, the left graph showing the 14 day titer of a monoclonal antibody and the right graph showing % viability of cells expressing the monoclonal antibody, which had been generated by rapid bulk sorting or 5 nM MTX, after passage with 50 nM MTX.
FIG. 15 is a series of FACS histogram overlays showing flow cytometry data from cell pools produced by sequential rapid bulk sorting or MTX amplification and showing the respective day 14 titers of the protein of interest.
FIG. 18 is a table showing pre-sort (pools) and sorted (clones) titers of a Fc fusion protein from cell pools and clones produced by MTX independent rapid bulk sorting (MTX Indy 10-10 pool 1) or by MTX amplification (20 nM pool 1 or 100 nM pool 2). Cloning efficiency and clone expansion survivability is also shown.

FIG. 22 is two graphs showing first the 14 day unfed batch titers of both rapid bulk pools and MTX amplified pools (with asterisked pools indicate which pools were targeted for sorting to generate clones), the second graph showing the resulting 14 day unfed batch titers for both rapid bulk sorted clones and MTX generated clones.

DETAILED DESCRIPTION

Figure 1:
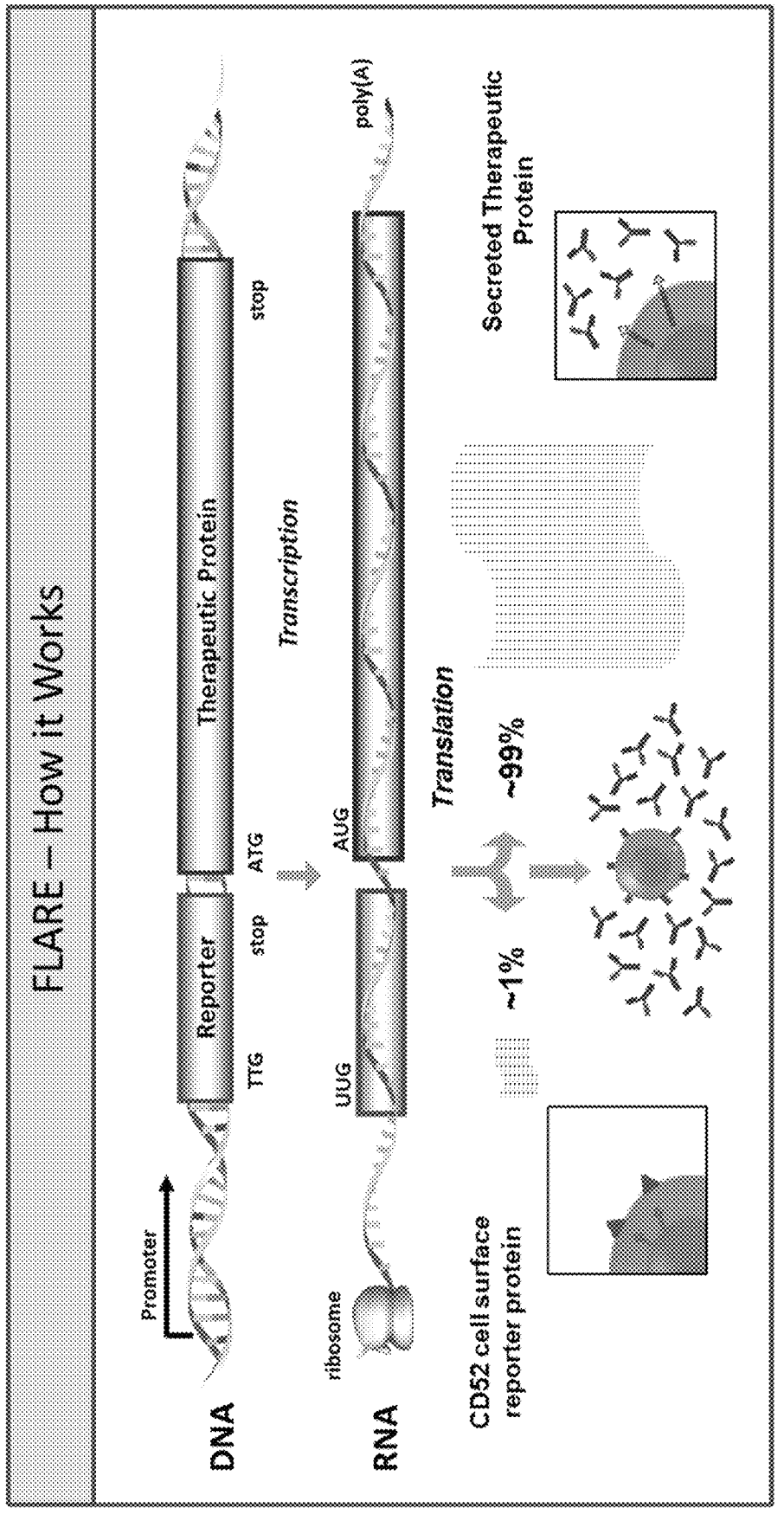
FIG. 1 is a diagram showing an example of how FLARE (Flow Cytometry Attenuated Reporter Expression) works.

Before the present invention is described, it is to be understood that this invention is not limited to particular methods and experimental conditions disclosed herein; as such methods and conditions may vary. It is also to be understood that the terminology used herein is for the purpose of describing particular embodiments only, and is not intended to be limiting, since the scope of the present invention will be limited only by the appended claims.

Furthermore, the practice of the invention employs, unless otherwise indicated, conventional molecular and cellular biological and immunological techniques within the skill of the art. Such techniques are well known to the skilled worker, and are explained fully in the literature. See, e.g., Ausubel, et al., ed., Current Protocols in Molecular Biology, John Wiley & Sons, Inc., NY, N.Y. (1987-2008), including all supplements, Molecular Cloning: A Laboratory Manual (Fourth Edition) by MR Green and J. Sambrook and Harlow et al., Antibodies: A Laboratory Manual, Chapter 14, Cold Spring Harbor Laboratory, Cold Spring Harbor (2013, 2$^{nd}$ edition).

I. Definitions

Unless otherwise defined herein, scientific and technical terms used herein have the meanings that are commonly understood by those of ordinary skill in the art. In the event of any latent ambiguity, definitions provided herein take precedent over any dictionary or extrinsic definition. Unless otherwise required by context, singular terms shall include pluralities and plural terms shall include the singular. The use of "or" means "and/or" unless stated otherwise. The use of the term "including", as well as other forms, such as "includes" and "included", is not limiting.

Generally, nomenclatures used in connection with cell and tissue culture, molecular biology, immunology, microbiology, genetics and protein and nucleic acid chemistry and hybridization described herein are those well-known and commonly used in the art. The methods and techniques provided herein are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

That the disclosure may be more readily understood, select terms are defined below.

As used herein, the term "polynucleotide" intends a polymeric form of nucleotides of any length, examples of which include, but are not limited to, a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs.

As used herein the term "polypeptide" intends a polymeric form of amino acids of any length, examples of which include, but are not limited to, a protein, a protein fragment, a multimeric protein, a fusion protein, an antibody (including fragments thereof) or a peptide.

As used herein, "fluorescence activated cell sorting" or "FACS" refers to a method of separating a population of cells into one or more sub-populations based on the presence, absence, or level of one or more FACS selectable polypeptides expressed by the cells. FACS relies on optical properties, including fluorescence, of individual cells in order to sort the cells into sub-populations.

As used herein, a "FACS selectable polypeptide" is a polypeptide that can be detected, directly or indirectly, by flow cytometry. Examples of FACS selectable polypeptides include polypeptides that include an extracellular domain (e.g., CD52 or CD59) that are capable of being bound to a detectable binding partner (e.g., a fluorescently-labeled antibody) for indirect detection of the polypeptide by flow cytometry. Other examples of FACS selectable polypeptides include fluorescent proteins such as green fluorescent protein (GFP), red fluorescent protein (RFP), yellow fluorescent protein (YFP), blue fluorescent protein (BFP), and variants thereof including eGFP, Venus, mCherry, mTomato, and the like, which may be detected directly by flow cytometry.

As used herein, "target polypeptide" refers to a protein, a protein fragment, a multimeric protein, a fusion protein, an antibody (including fragments thereof), or a peptide that can be produced in host cells and in the aspects exemplified herein, the target polypeptide is selected because of its potential as a therapeutic agent, e.g., an antibody (including a fragment thereof), a Fc fusion protein, a hormone or an enzyme. In some embodiments, the target polypeptide is a secreted protein. However, the methods described herein are not limited for the selection and scale-up of therapeutic polypeptides. For example, diagnostic polypeptides or polypeptides for use in the environment are also contemplated for use as a target polypeptide in a method disclosed herein.

As used herein, the term "antibody" refers to such assemblies (e.g., intact antibody molecules, antibody fragments, or variants thereof) which have significant known specific immunoreactive activity to an antigen of interest. Antibodies and immunoglobulins comprise light and heavy chains, with or without an interchain covalent linkage between them. Basic immunoglobulin structures in vertebrate systems are relatively well understood.

The term "antibody" includes entire antibodies as well as antigen-binding fragments and variants of such antibodies. Antibodies may be of any class, such as IgG, IgA or IgM; and of any subclass, such as IgG1 or IgG4. The antibody can be a polyclonal or a monoclonal antibody, or it can be fragments of the polyclonal or monoclonal antibody. The antibody can be chimeric, humanized, bi-specific, bi-functional or totally human. Any antigen-binding fragment or variant of an antibody is also contemplated, such as Fab, Fab', Fab'2, single chain variable regions and variations of the same.

A "Fc fusion protein" refers to a protein comprising an immunoglobulin Fc domain that is linked, directly or indirectly, to a polypeptide, such as a protein or peptide. The linked polypeptide can be any proteinaceous molecule of interest, such as a ligand, a receptor, or an antigenic peptide.

As used herein, "producer cells" refer to cells that are suitable for production of proteins, e.g., in a small- or large-scale manufacturing method for producing biologics. In some embodiments, producer cells are mammalian or insect cells. Producer cells are further discussed herein.

As used herein, a "heterogeneous population of producer cells" is a population of cells that expresses varying levels of one or more polypeptides, e.g., a FACS selectable polypeptide and a target polypeptide that are encoded by the same multicistronic mRNA. In some embodiments, the varying levels include a variation (e.g., a range) of at least 10-fold, at least 100-fold, at least 1,000-fold, or at least 10,000-fold of the one or more polypeptides in the population. In some embodiments, the varying levels include a variation (e.g., a range of relative fluorescence) of at least 10-fold, at least 100-fold, at least 1,000-fold, or at least 10,000-fold of the FACS selectable polypeptide in the population as detected by flow cytometry (e.g., on a BD Influx™ cell sorter). Methods for generating heterogeneous populations of producer cells are described herein.

As used herein, a "multicistronic mRNA" is an mRNA that contains at least two open reading frames (ORFs) that are capable of encoding two or more polypeptides.

As used herein, a "drug-selection-free medium" is a culture medium that is devoid of a drug (e.g., methotrexate (MTX)) that is used to select sub-populations of cells that express a protein that confers drug-resistance to the sub-population.

As used herein, "medium-based selection" is a selection process by which the culture medium is altered to include a selection agent (e.g., MTX) or to exclude a component of medium, which results in selection of a sub-population that is resistant to the selection agent or can survive in the absence of the medium component.

As used herein, "nucleotide-deficient medium" is culture medium that is devoid of or contains low levels (e.g., less than 10 micrograms/mL) of one or more of adenine (A), cytosine (C), guanine (G), thymine (T), hypoxanthine, or thymidine. In some embodiments, nucleotide-deficient medium is medium that is devoid of hypoxanthine and thymidine. Exemplary nucleotide-deficient medium includes CD CHO Medium (Gibco, Life Technologies, Catalogue numbers 10743 (liquid) and 12490 (granulated)).

As used herein, a "viability marker" is a cell characteristic that is indicative of cell viability and is detectable by FACS. Exemplary viability markers include forward scatter, side scatter, propidium iodide stain, or combinations thereof.

As used herein, the term "non-AUG start codon" is intended to include any non-AUG polynucleotide (typically a triplet) that functions as a start site for translation initiation with reduced efficiency relative to that of an AUG start codon. Naturally occurring alternate start codon usage is known in the art and described for example in Kozak (1991) J. Cell Biol. 115(4): 887-903; Mehdi et al. (1990) Gene 91:173-178; Kozak (1989) Mol. Cell. Biol. 9(11): 5073-5080. In general, non-AUG start codons have decreased translation efficiencies compared to that of an AUG; for example, the alternate start codon GUG may have 3-5% translation efficiency compared to that of an AUG (100%). The translation efficiency of a non-AUG start codon can also be affected by its sequence context; for example, an optimal Kozak consensus sequence is reported to have a positive effect on translation initiation at non-AUG start codons (Mehdi et al. (1990) Gene 91:173-178; Kozak (1989) Mol. Cell. Biol. 9(11): 5073-5080). The complete Kozak DNA consensus sequence is GCCRCCATGG (SEQ ID NO: 7), where the start codon ATG (AUG in RNA) is underlined, the A of the ATG start codon is designated as the +1 position, and "R" at position −3 is a purine (A or G). The two most highly conserved positions are a purine, preferably an A, at −3 and a G at +4 (Kozak (1991) J Cell Biol 115(4): 887-903). Alternate start codon usage is described for attenuated expression of a selectable marker in U.S. Patent Publication 2006/0172382 and U.S. Patent Publication 2006/0141577. One of skill in the art will recognize that the sequences described herein as DNA will have correlative sequences as RNA molecules e.g., DNA sequence ATG, for example, would correspond to RNA sequence AUG, and vice versa.

As used herein, the term "pre-sort" when used in connection with a population of cells refers to a population of cells that has not yet undergone the FACS selection as described herein, e.g. using FLARE, and optionally has been subjected to initial selection with MTX (e.g., 5 nM MTX) or MTX-free medium (e.g. 0 nM MTX) prior to undergoing the FACS selection.

As used herein, the term "FLARE" refers to "Flow Cytometry Attenuated Reporter Expression." FLARE is an expression system utilizing a multicistronic mRNA that contains at least two open reading frames (ORFs), one upstream ORF containing a non-AUG start codon and encoding a FACS selectable polypeptide and a second downstream ORF containing an AUG start codon and encoding a target polypeptide.

As used herein, the term "about" shall refer to a range of tolerance of 10% around a stated value. Therefore, when the term "about" is used to modify a stated value, the range indicated will encompass any number within ±0.01%, 0.02%, 0.05%, 0.1%, 0.2%, 0.5%, 1%, 2%, 3%, 4%, 5%, 6%, 7%, 8%, 9%, or 10% of the stated value.

II. Methods of FACS for Batch Selection of Producer Cells

In some aspects, the disclosure relates to a method of fluorescence activated cell sorting (FACS) to batch select producer cells expressing a target polypeptide. In some embodiments, the method comprises:

(a) providing a heterogeneous population of producer cells, wherein the producer cells in the population express varying levels of a FACS selectable polypeptide and a target polypeptide that are encoded by the same multicistronic mRNA, (b) selecting from the heterogeneous population of producer cells a first heterogeneous sub-population of producer cells using FACS, wherein the producer cells in the first heterogeneous sub-population express the FACS selectable polypeptide at a level that is higher than the level of at least 80% (e.g., at least 80%, at least 85%, at least 90%, at least 91%, at least 92%, at least 93%, at least 94%, at least 95%, at least 96%, at least 97%, at least 98%, or at least 99%) of the producer cells in the heterogeneous population in (a), and (c) expanding the first heterogeneous sub-population of producer cells in drug-selection-free medium, thereby producing an expanded first heterogeneous sub-population of producer cells.

In some embodiments, the method further comprises:

(d) selecting from the expanded first heterogeneous sub-population of producer cells in (c) a second heterogeneous sub-population of producer cells using FACS, wherein the producer cells in the second sub-population express the FACS selectable polypeptide at a level that is higher than the level of at least 80% (e.g., at least 80%, at least 85%, at least 90%, at least 91%, at least 92%, at least 93%, at least 94%, at least 95%, at least 96%, at least 97%, at least 98%, or at least 99%) of the producer cells in the expanded first heterogeneous sub-population of producer cells in (c), and (e) expanding the second heterogeneous sub-population of producer cells in a drug-selection-free medium, thereby producing an expanded second heterogeneous sub-population of producer cells. In some embodiments, steps (d) and (e) are repeated at least twice (e.g., twice, three times, four times, five times, or more) to produce an expanded third, fourth, fifth, sixth, etc. heterogeneous sub-population of producer cells.

FACS cell sorters suitable for carrying out a method described herein are well-known in the art and commercially available. Exemplary FACS cell sorters include BD Influx™

(BD Biosciences) and other equivalent cell sorters produced by other commercial vendors such as Sony, Bio-Rad and Beckman Coulter.

In some embodiments, the producer cells are cultured under conditions that facilitate expression of the FACS selectable polypeptide in the cells. In some embodiments, the FACS selectable marker is a cell surface marker. Examples of cell surface marker polypeptides include, but are not limited to CD2, CD20, CD52 or CD59. Exemplary, non-limiting, amino acid sequences for CD52 and CD59 cell surface marker polypeptides are provided below.

```
Amino Acid Sequence for Exemplary Human CD52
polypeptide (splice acceptor mutant):
                              (SEQ ID NO: 1)
LERFLFLLLTISLLVLVQIQTGLSGQNDTSQTSSPSASSNISGGIFLFF

VANAIIHLFCFS*

Amino Acid Sequence for Exemplary Human CD59
polypeptide (splice acceptor mutant):
                              (SEQ ID NO: 2)
LGIQGGSVLFGLLLVLAVFCHSGHSLQCYNCPNPTADCKTAVNCSSDFD

ACLITKAGLQVYNNCWKFEHCNFNDVTTRLRENELTYYCCKKDLCNFNE

QLENGGTSLSEKTVLLLVTPFLAAAWSLHP*

Amino Acid Sequence for Exemplary Mouse CD52
polypeptide (splice acceptor mutant):
                              (SEQ ID NO: 6)
LKSFLLFLTIILLVVIQIQTGSLGQATTAASGTNKNSTSTKKTPLKSGA

SSIIDAGACSFLFFANTLICLFYLS*
```

Any method known in the art useful for detecting a cell surface marker may be used in connection with the methods of the disclosure. For example, an antibody or other cell surface marker-specific binding agent is contacted directly or indirectly with the producer cell under conditions that favor binding of antibody to the FACS selectable polypeptide and therefore the producer cell. The selection of the binding agent or antibody is determined by: 1) its ability to selectively bind the FACS selectable polypeptide that is expressed on the host cell; and 2) its ability to be labeled with a detectable label or bind to a detectable label, for example, for use in flow cytometry or FACS.

In an alternate embodiment, a first agent can be a protein or peptide that binds to the FACS selectable polypeptide which first agent also in turn binds to a second agent that is capable of being detectably labeled (e.g., incorporating a fluorescent, enzymatic, colormetric, or other detectable label). It is intended, although not always explicitly stated that "indirect" binding to the FACS selectable polypeptide includes the use of any number of intermediate partners.

In some embodiments, the agent or antibody binds directly to the cell surface marker and comprises a fluorescent label. Suitable fluorescent labels include, but are not limited to, fluorescein, rhodamine, tetramethylrhodamine, eosin, erythrosin, coumarin, methyl-coumarins, pyrene, Malacite green, stilbene, Lucifer Yellow, Cascade Blue, and Texas Red. Other suitable optical dyes are described in the Molecular Probes® Handbook, 11$^{th}$ Edition, 2010.

In some embodiments, the fluorescent label is functionalized to facilitate covalent attachment to the agent or agents. Suitable functional groups, include, but are not limited to, isothiocyanate groups, amino groups, haloacetyl groups, maleimides, succinimidyl esters, and sulfonyl halides, all of which may be used to attach the fluorescent label to a second molecule. The choice of the functional group of the fluorescent label will depend on the site of attachment to the linker, the agent, the FACS selectable polypeptide, or the second labeling agent.

Attachment of the fluorescent label may be either direct or via a linker to the antibody or agent. In one aspect, the linker is a relatively short coupling moiety that generally is used to attach molecules. In this embodiment, attachment of the first labeling moiety to the candidate agents will be done as is generally appreciated by those in the art, and may include techniques outlined above for the incorporation of fluorescent labels.

Materials and techniques for design and construction of labeled antibodies and other agents for use in cytometry are known in the art and described for example, in Bailey et al. (2002) Biotech. Bioeng. 80(6); 670-676; Carroll and Al-Rubeai (2004) Expt. Opin. Biol. Therapy 4:1821-1829; Yoshikawa et al. (2001) Biotechnol. Bioeng. 74:435-442; Meng et al. (2000) Gene 242:201-207; Borth et al. (2001) Biotechnol. Bioeng. 71 (4):266-273; Zeyda et al. (1999) Biotechnol. Prog. 15:953-957; Klucher et al. (1997) Nucleic Acids Res. 25(23):4853-4860; and Brezinsky et al. (2003) J. Imumunol. Methods 277:141-155.

Suitable binding pairs for use in indirectly linking the label to the agent (which in turn, binds the FACS selectable polypeptide) include, but are not limited to, antigens/antibodies, including digoxigenin/antibody, dinitrophenyl (DNP)/anti-DNP, dansyl-X/anti-dansyl, fluorescein/anti-fluorescein, lucifer yellow/anti-lucifer yellow, rhodamine/anti-rhodamine; and biotin/avidin (or biotin/streptavidin). The binding pairs should have high affinities for each other, sufficient to withstand the shear forces during FACS sorting or other detection system used in connection with the disclosure.

Thus, in some aspects, first labeling moieties (when second labeling moieties are used), include, but are not limited to, haptens such as biotin. Biotinylation of target molecules is well known, for example, a large number of biotinylation agents are known, including amine-reactive and thiol-reactive agents, for the biotinylation of proteins, nucleic acids, carbohydrates, carboxylic acids. Similarly, a large number of haptenylation reagents are also known.

The antibodies used in a method described herein can be produced in cell culture, in phage, or in various animals, including but not limited to cows, rabbits, goats, mice, rats, hamsters, guinea pigs, sheep, dogs, cats, monkeys, chimpanzees, apes, etc., so long as the antibodies retain specificity of binding for the FACS selectable polypeptide. Antibodies can be tested for specificity of binding by comparing binding to appropriate antigen to binding to irrelevant antigen or antigen mixture under a given set of conditions.

In embodiments in which the antibody or agent against the FACS selectable polypeptide is not directly labeled, the antibody or agent preferably also contains and retains the ability to bind a secondary agent which is detectable after binding to the cell via the FACS selectable polypeptide.

In some embodiments, when the FACS selectable polypeptide is CD59, the FACS selectable polypeptide may be detected using an anti-CD59 antibody. "Anti-CD59 antibody" refers to an antibody that specifically recognizes and binds CD59. Anti-CD59 antibodies can be generated by methods well known in the art. See for example, CURRENT PROTOCOLS IN MOLECULAR BIOLOGY (F. M. Ausubel, et al. eds., 1987 to present versions) and ANTI-BODIES A LABORATORY MANUAL, Second edition (Greenfield, ed. 2013). Additionally, several anti-CD59 antibodies are commercially available (e.g., antibodies conju-gated to a fluorescent label, such as those sold by the commercial vendors AbCam, SeroTec, and BioLegend).

In some embodiments, when the FACS selectable polypeptide is CD52, the FACS selectable polypeptide may be detected using an anti-CD52 antibody. "Anti-CD52 antibody" refers to an antibody that specifically recognizes and binds CD52. Anti-CD52 antibodies can be generated by methods well known in the art. Additionally, several anti-CD52 antibodies are commercially available (e.g., antibodies conjugated to a fluorescent label, such as those sold by the commercial vendors AbCam, SeroTec, and BioLegend).

In a particular embodiment, when the FACS selectable polypeptide is CD20, the FACS selectable polypeptide may be detected using an anti-CD20 antibody. "Anti-CD20 antibody" refers to an antibody that specifically recognizes and binds CD20 polypeptide or protein. Anti-CD20 antibodies can be generated by methods well known in the art. Additionally, several anti-CD20 antibodies are commercially available from vendors such as BD Pharmigen; Beckman Coulter, Inc. (Fullerton, Calif., numerous clones including Catalog No. 6604106 Clone H299 (B1); Isotype IgG2a and Catalog No. IM1565 Clone L26, Isotype IgG2a); Invitrogen (Carlsbad, Calif., Clone: BH-20, Isotype: IgG2a and Clone: B-H20, Isotype: IgG2a); BioLegend (San Diego, Calif, Catalog. No. 302301, Clone: 21-7, Isotype: IgG2b, e); EMD Biosciences, Inc., CALBIOCHEM® Brand (San Diego, Calif, Catalog No. 217670 Clone 2H7, Isotype: IgG2b); and Anaspec (San Jose, Calif., Catalog No. 29587).

In an exemplary, non-limiting method, a heterogeneous population of producer cells as described herein is contacted with an agent that recognizes and directly or indirectly binds the FACS selectable polypeptide, if present, on the surface of the cells. The contacting is performed under conditions that favor or are suitable for specific binding (directly or indirectly) of the agent or antibody with the FACS selectable polypeptide. The cells that are bound to the agent or antibody are then selected for using FACS (e.g., by gating for cells that express the FACS selectable polypeptide at a high level such as a level that is at least 80% of the level of the population) and used to create a heterogeneous sub-population of producer cells. The heterogeneous sub-population of producer cells are then grown under conditions that result in expansion of the population to produce enough cells to perform a second round of FACS, if desired, or to produce a batch population to produce the target polypeptide. After at least one round of FACS, the heterogeneous sub-population of producer cells can be further sorted to produce clonal populations. Preparation of a clonal population can be performed by any method known in the art. For example, in one embodiment, the selected cells may be plated into 96-well (or other size) plates at a density of one cell per well and permitted to grow for a period of time (e.g., typically 7-28 days) which permits the single cell to grow into a multi-cell colony of daughter cells (i.e., a clonal population). The method may next comprise analyzing one or more of the clonal populations by detecting the level of the FACS selectable polypeptide and/or target polypeptide expression on said clonal population and selecting one or more clonal populations with a high expression level of the FACS selectable polypeptide and/or target polypeptide, thereby selecting one or more clonal populations stably expressing the target polypeptide. In certain embodiments, the clonal population is cultured for 7-28 days after plating at a single cell density before the clonal populations are analyzed. The method may further include contacting the clonal population with a detectable agent that recognizes and directly or indirectly binds the FACS selectable polypeptide, if present, on the surface of the clonal cell under conditions that favor binding of the agent with the FACS selectable polypeptide; and selecting or detecting one or more cells that are directly or indirectly bound to the agent or antibody. These cells so selected also can be isolated and cultured. The method may further include analyzing target polypeptide expression of the one or more clones, e.g., using protein A screening (such as when the target polypeptide is an antibody or Fc-fusion), Western blot, SDS page with Coomassie Blue or silver stain, or an enzyme activity assay.

Accordingly, in some embodiments, a method provided herein may further comprise isolating one or more single producer cells from an expanded first or second (or third or fourth or fifth or sixth) heterogeneous sub-population and individually culturing the one or more single producer cells to produce clonal populations of the one or more single producer cells.

In some embodiments of any one of the methods provided, the expanded first heterogeneous sub-population of producer cells yields a 1.2- to 5-fold, 1.2- to 4-fold, 1.2- to 3-fold, 1.2- to 2.5-fold, 1.5- to 10-fold, 1.5- to 9-fold, 1.5- to 8-fold, 1.5- to 7-fold, 1.5- to 6-fold, 1.5- to 5-fold, 1.5- to 4-fold, 1.5- to 3-fold, or 1.5- to 2.5-fold, 2- to 10-fold, 2- to 9-fold, 2- to 8-fold, 2- to 7-fold, 2- to 6-fold, or 2- to 5-fold improvement in production of the target polypeptide compared to that of the heterogeneous population of producer cells.

In some embodiments of any one of the methods provided, the expanded second heterogeneous sub-population of producer cells yields a 1.2- to 5-fold, 1.2- to 4-fold, 1.2- to 3-fold, 1.2- to 2.5-fold, 1.5- to 5-fold, 1.5- to 4-fold, 1.5- to 3-fold, or 1.5- to 2.5-fold improvement in production of the target polypeptide compared to that of the expanded first heterogeneous sub-population of producer cells.

In some embodiments of any one of the methods provided, at least one of the clonal populations of the one or more single cells yields a 3- to 30-fold, 5- to 30-fold, 5- to 20-fold, 3-to 20-fold, 5- to 10-fold, 3- to 10-fold, or 3- to 5-fold improvement in production of the target polypeptide compared to that of the heterogeneous population of producer cells (e.g., compared to the average production of the target polypeptide in the heterogeneous population of producer cells).

In some embodiments of any one of the methods provided, the method further comprises isolating the target polypeptide from the expanded first or second (or third or fourth or fifth or sixth) heterogeneous sub-population or the clonal population. The target polypeptide can be isolated using any method known in the art and may be further purified, e.g., according to Current Good Manufacturing Practice (CGMP) for recombinant proteins and antibodies, to a purity level of at least 90%, at least 95%, at least 96%, at least 97%, at least 98%, at least 99%, at least 99.9%, or more.

In some embodiments of any one of the methods provided, the heterogeneous population of producer cells subject to FACS contains $1$-$500\times10^6$ cells, $1$-$400\times10^6$ cells, $1$-$300\times10^6$ cells, $1$-$200\times10^6$ cells, $1$-$150\times10^6$ cells, $10$-$500\times10^6$ cells, $10$-$400\times10^6$ cells, $10$-$300\times10^6$ cells, $10$-$200\times10^6$ cells, $10$-$150\times10^6$ cells, $50$-$500\times10^6$ cells, $50$-$400\times10^6$ cells, $50$-$300\times10^6$ cells, $50$-$200\times10^6$ cells, $50$-$150\times10^6$ cells, $80$-$500\times10^6$ cells, $80$-$400\times10^6$ cells, $80$-$300\times10^6$ cells, $80$-$200\times10^6$ cells, $80$-$150\times10^6$ cells, or $80$-$120\times10^6$ cells.

In some embodiments of any one of the methods provided, the first and/or second (and/or third and/or fourth and/or fifth and/or sixth) heterogeneous sub-population of producer cells contains $0.1$-$10.0\times10^6$ cells, $0.2$-$10.0\times10^6$ cells, $0.3$-$10.0\times10^6$ cells, $0.4$-$10.0\times10^6$ cells, $0.5$-$10.0\times10^6$ cells, $0.1$-$9.0\times10^6$ cells, $0.2$-$9.0\times10^6$ cells, $0.3$-$9.0\times10^6$ cells, $0.4$-$9.0\times10^6$ cells, $0.5$-$9.0\times10^6$ cells, $0.1$-$8.0\times10^6$ cells, $0.2$-$8.0\times10^6$ cells, $0.3$-$8.0\times10^6$ cells, $0.4$-$8.0\times10^6$ cells, $0.5$-$8.0\times10^6$ cells, $0.1$-$7.0\times10^6$ cells, $0.2$-$7.0\times10^6$ cells, $0.3$-$7.0\times10^6$ cells, $0.4$-$7.0\times10^6$ cells, $0.5$-$7.0\times10^6$ cells, $0.1$-$6.0\times10^6$ cells, $0.2$-$6.0\times10^6$ cells, $0.3$-$6.0\times10^6$ cells, $0.4$-$6.0\times10^6$ cells, or $0.5$-$6.0\times10^6$ cells prior to expansion.

In some embodiments of any one of the methods provided, an expansion step described herein (e.g., step c) or step e)) is performed for between 5-21 days, 5-14 days, 6-21 days, 6-14 days, 7-21 days, or 7-14 days.

In some embodiments of any one of the methods provided, the drug-selection-free medium is methotrexate-free medium or methionine sulphoximine-free medium.

III. Producer Cells and Methods of Production Thereof

Aspects of the disclosure relate to producer cells and populations of producer cells for use in a method described herein. A producer cell can be generated using any cell type suitable for production of a target polypeptide from a multicistronic mRNA. In some embodiments, the cell is a eukaryotic cell. Examples of suitable eukaryotic cells to produce a target polypeptide include, but are not limited to, a Chinese Hamster Ovary cell line, including those designated CHO-DBX11, CHO-DG44, CHO-S, CHO-K1, and the hamster cell line BHK-21; the murine cell lines designated NIH3T3, NSO, C127, the simian cell lines COS, Vero; and the human cell lines HeLa, HEK293 (also called 293), NIH-3T3, U-937 and Hep G2. Additional examples include yeast cells, insect cells (e.g., *Drosophila* Schnieder S2 cells, Sf9 insect cells, WO 94/126087, BTI-TN-5B1-4 (High Five™) insect cells (Invitrogen)), plant cells, avian cells, fungal cells and bovine cells. Examples of yeast useful for expression include, but are not limited to *Saccharomyces, Schizosaccharomyces, Hansenula, Candida, Torulopsis, Yarrowia*, or *Pichia*. See e.g., U.S. Pat. Nos. 4,812,405; 4,818,700; 4,929,555; 5,736,383; 5,955,349; 5,888,768 and 6,258,559. Other examples of producer cells can be prokaryotic, including bacterial cells such as *E. coli* (e.g., strain DH5aTM) (Invitrogen, Carlsbad, CA), PerC6 (Crucell, Leiden, NL), *B. subtilis* and/or other suitable bacteria. The cells can be purchased from a commercial vendor such as the American Type Culture Collection (ATCC, Rockville, Md. USA) or cultured from an isolate using methods known in the art.

In some embodiments a heterogeneous population of producer cells is provided. The heterogeneous population of producer cells can be produced using any method known in the art or described herein. In some embodiments of any one of the methods provided, the heterogeneous population of producer cells is produced by transfecting cells with a vector that encodes the multicistronic mRNA and subjecting the transfected cells to less than or equal to one round of medium-based selection to select cells expressing varying levels (e.g., a variation of at least 10-, 100-, 1,000-, or 10,000-fold) of the multicistronic mRNA. In some embodiments, the vector further contains a dihydrofolate reductase (DHFR) gene and the medium-based selection is methotrexate (MTX, e.g., 1 nM-100 nM MTX), nucleotide-deficient medium, or a combination thereof. In some embodiments, the vector further contains a glutamine synthetase (GS) gene and the medium-based selection is methionine sulphoximine (MSX, e.g., 25-100 μM MSX). In some embodiments, FACS is used to select cells expressing varying levels of the multicistronic mRNA, e.g., by using the FACS selectable polypeptide level to select the cells. In some embodiments, the vector lacks a drug-selectable marker, e.g., lacks a DHFR gene or GS gene.

The producer cells of the disclosure contain a recombinant polynucleotide (e.g., a recombinant cDNA) that encodes a multicistronic mRNA molecule from which the target and FACS selectable polypeptides are separately translated from different ORFs. In some embodiments, a first ORF is provided which encodes a FACS selectable polypeptide, such as CD59 or CD52. Exemplary, non-limiting first ORF sequences for CD52 and CD59 are provided below.

```
Exemplary CD52 Human ORF (splice acceptor mutant):
                                      (SEQ ID NO: 3)
ttggagcgcttcctcttcctcctactcaccatcagcctcctcgttttgg tacaaatacaaaccggactctccggacaaaacgacaccagccaaaccag cagcccctcagcatccagcaacataagcggaggcattttccttttcttc gtcgccaacgccataatccacctcttctgcttcagttga Exemplary CD59 Human ORF (splice acceptor mutant):
                                      (SEQ ID NO: 4)
ttgggaatccaaggagggtctgtcctgttcgggctgctgctcgtcctcg ctgtcttctgccattccggtcatagcctgcagtgctacaactgtcctaa cccaactgctgactgcaaaacagccgtcaattgttcatctgattttgac gcgtgtctcattaccaaagctgggttacaagtgtataacaactgttgga agtttgagcattgcaatttcaacgacgtcacaacccgcttgagggaaaa cgagctaacgtactactgctgcaagaaggacctgtgtaactttaacgaa cagcttgaaaacggagggacatccttatcagagaaaacagttcttctgc tggtgactccatttctggcagctgcttggagccttcatccctaa Exemplary CD52 Mouse ORF (splice acceptor mutant):
                                      (SEQ ID NO: 8)
ttgaagagcttcctcctcttcctcactatcattcttctcgtagtcattc agatacaaacaggatccttaggacaagccactacggccgcttcaggtac taacaaaaacagcacctccaccaaaaaaacccccttaaagagcggggcc tcatccatcatcgacgcgggcgcttgcagtttcctcttcttcgccaata cccttatttgcctcttctacctcagctaactgagtaa
```

In some embodiments, a second ORF is provided which encodes a target polypeptide, such as an antibody, enzyme or Fc fusion protein. In some embodiments, separate translation is accomplished by use of a non-AUG start codon for translation initiation of the FACS selectable polypeptide and the use of an AUG start codon for translation initiation of the target polypeptide. In this embodiment, generally the polynucleotide encoding the target polypeptide is located downstream from the polynucleotide encoding the FACS selectable polypeptide. Separate translation can also be achieved using an internal ribosome entry site (IRES). In some embodiments, the IRES element is located upstream from the polynucleotide encoding the target polypeptide and downstream from the polynucleotide encoding the FACS selectable polypeptide. In some embodiments, the IRES element is located upstream from the polynucleotide encoding the FACS selectable polypeptide and downstream from the polynucleotide encoding the target polypeptide.

In some embodiments, a non-AUG start codon is located within the DNA encoding the FACS selectable polypeptide in such a way that translation of the FACS selectable polypeptide is less efficient than translation of the target polypeptide. To achieve decreased translation efficiency, the AUG start codon of the FACS selectable polypeptide may be changed to an alternate non-AUG start codon, examples of which include but are not limited to: CUG, GUG, UUG, AUU, AUA, or ACG.

Thus, when using an alternate non-AUG start codon, expression of a FACS selectable polypeptide can be attenuated relative to that of a co-expressed target polypeptide. In addition to alteration of the start codon, the DNA encoding the FACS selectable polypeptide may be modified at all internal ATG triplets to prevent internal initiation of translation. In some embodiments, the FACS selectable polypeptide has a short amino acid sequence (<200 amino acids) with few (<10) ATG triplets.

Without wishing to be bound by theory, to initiate translation of the mRNA encoding both the FACS selectable polypeptide and the target polypeptide, ribosomes begin scanning at the 5' cap structure of the mRNA with the majority scanning past the alternate start codon (for example, UUG) and instead initiate translation at the downstream AUG start codon. However, translation initiation can occur at the alternate start codon with very low frequency so that a low level of the FACS selectable polypeptide is expressed.

To make a producer cell, the recombinant polynucleotide(s) can be inserted into the cell using any suitable transfer technique (e.g., by transformation, transfection, electroporation or transduction). In some embodiments, a vector for insertion of the polynucleotide(s) into the cell can be used. Vectors that may be used include plasmid, virus, phage, transposons, and minichromosomes of which plasmids are a typical embodiment. Generally such vectors further include a signal sequence, origin of replication, one or more marker genes, a promoter and transcription termination sequences operably linked to the gene encoding the multicistronic mRNA so as to facilitate expression. Examples of suitable DNA viral vectors include adenovirus (Ad) or adeno-associated virus (AAV). Adenovirus-based vectors for the delivery of polynucleotides are known in the art and may be obtained commercially or constructed by standard molecular biological methods. Adenoviruses (Ads) are a group of viruses, including over 50 serotypes. See, e.g., International PCT Application No. WO 95/27071. Other viral vectors for use in the present disclosure include vectors derived from vaccinia, herpesvirus (e.g., herpes simplex virus (HSV)), and retroviruses. Gene delivery vehicles also include several non-viral vectors, including DNA/liposome complexes, and targeted viral protein-DNA complexes.

Vectors that contain both a promoter and a cloning site into which a polynucleotide can be operatively linked are known in the art and available from commercial vendors. Such vectors are capable of transcribing RNA in vitro or in vivo, and are commercially available from sources such as Agilent Technologies and Promega Corporation. In order to optimize expression and/or in vitro transcription, it may be necessary to remove, add or alter 5' and/or 3' untranslated portions to eliminate extra, potentially inappropriate alternative translation initiation codons or other sequences that may interfere with or reduce expression, either at the level of transcription or translation. Alternatively, consensus ribosome binding sites can be inserted immediately 5' of the start codon to enhance expression.

Yet further disclosed are producer cells that contain a first recombinant polynucleotide encoding a multicistronic mRNA as described herein and further contain a second recombinant polynucleotide encoding a second target protein or polypeptide under the control of the first or a second promoter element.

A promoter can be provided for expression in the producer cell. Promoters can be constitutive or inducible. For example, a promoter can be operably linked to a nucleic acid encoding a multicistronic mRNA, such that it directs expression of the encoded polypeptides. A variety of suitable promoters for prokaryotic and eukaryotic hosts are available. Prokaryotic promoters include lac, tac, T3, T7 promoters for *E. coli;* 3-phosphoglycerate kinase or other glycolytic enzymes e.g., enolase, glyceralderhyde 3-phosphate dehydrogenase, hexokinase, pyruvate decarboxylase, phosphofructokinase, glucose 6 phosphate isomerase, 3-phosphoglycerate mutase and glucokinase. Eukaryotic promoters include inducible yeast promoters such as alcohol dehydrogenase 2, isocytochrome C, acid phosphatase, metallothionein and enzymes responsible for nitrogen metabolism or maltose/galactose utilization; RNA polymerase II promoters including viral promoters such as polyoma, fowlpox and adenoviruses (e.g., adenovirus 2), bovine papilloma virus, avian sarcoma virus, cytomegalovirus (in particular, the immediate early gene promoter), retrovirus, hepatitis B virus, actin, rous sarcoma virus (RSV) promoter and the early or late Simian virus 40 and non-viral promoters such as EF-1 alpha (Mizushima and Nagata (1990) Nucleic Acids Res. 18(17):5322). Those of skill in the art will be able to select the appropriate promoter for expressing a target polypeptide.

Where appropriate, e.g., for expression in cells of higher eukaryotes, additional enhancer elements can be included instead of or as well as those found located in the promoters described above. Suitable mammalian enhancer sequences include enhancer elements from globin, elastase, albumin, fetoprotein, metallothionine and insulin. Alternatively, one may use an enhancer element from a eukaryotic cell virus such as SV40 enhancer, cytomegalovirus early promoter enhancer, polyoma enhancer, baculoviral enhancer or murine IgG2a locus (see, WO 04/009823). Whilst such enhancers are often located on the vector at a site upstream to the promoter, they can also be located elsewhere e.g., within the untranslated region or downstream of the polyadenylation signal. The choice and positioning of enhancer may be based upon compatibility with the host cell used for expression.

In addition, the vectors (e.g., expression vectors) may comprise a selectable marker for selection of host cells carrying the vector, and, in the case of a replicable vector, an origin of replication. Genes encoding products which confer antibiotic or drug resistance are common selectable markers and may be used in prokaryotic (e.g., f3-lactamase gene (ampicillin resistance), tet gene (tetracycline resistance) and eukaryotic cells (e.g., neomycin (G418 or geneticin), gpt (mycophenolic acid), ampicillin, or hygromycin 5 resistance genes). The dihydrofolate reductase (DHFR) gene permits selection with methotrexate or nucleotide-deficient medium in a variety of hosts. Similarly, the glutamine synthetase (GS) gene permits selection with methionine sulphoximine. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

In eukaryotic systems, polyadenylation and termination signals may be operably linked to a polynucleotide encoding the multicistronic mRNA as described herein. Such signals are typically placed 3' of an open reading frame. In mammalian systems, non-limiting examples of polyadenylation/termination signals include those derived from growth hormones, elongation factor-1 alpha and viral (e.g., SV40) genes or retroviral long terminal repeats. In yeast systems, non-limiting examples of polydenylation/termination signals include those derived from the phosphoglycerate kinase (PGK) and the alcohol dehydrogenase 1 (ADH) genes. In prokaryotic systems polyadenylation signals are typically not required and it is instead usual to employ shorter and more defined terminator sequences. The choice of polyadenylation/termination sequences may be based upon compatibility with the host cell used for expression. In addition to the above, other features that can be employed to enhance yields include chromatin remodeling elements, introns and host cell specific codon modification.

Producer cells may be cultured in spinner flasks, shake flasks, roller bottles, wave reactors (e.g., System 1000 from wavebiotech.com) or hollow fiber systems, or for large scale production, stirred tank reactors or bag reactors (e.g., Wave Biotech, Somerset, New Jersey USA) are used particularly for suspension cultures. Stirred tank reactors can be adapted for aeration using e.g., spargers, baffles or low shear impellers. For bubble columns and airlift reactors, direct aeration with air or oxygen bubbles may be used. Where the host cells are cultured in a serum-free culture medium, the medium can be supplemented with a cell protective agent such as pluronic F-68 to help prevent cell damage as a result of the aeration process. Depending on the host cell characteristics, microcarriers may be used as growth substrates for anchorage dependent cell lines, or the cells may be adapted to suspension culture. The culturing of host cells, particularly vertebrate host cells, may utilize a variety of operational modes such as batch, fed-batch, repeated batch processing (see, Drapeau et al. (1994) Cytotechnology 15:103-109), extended batch process or perfusion culture. Although recombinantly transformed producer cells may be cultured in serum-containing media such media comprising fetal calf serum (FCS), in some embodiments, such host cells are cultured in serum-free media such as disclosed in Keen et al. (1995) Cytotechnology 17:153-163, or commercially available media such as ProCHO-CDM or UltraCHOTM (Cambrex NJ, USA), supplemented where necessary with an energy source such as glucose and synthetic growth factors such as recombinant insulin. The serum-free culturing of host cells may require that those cells are adapted to grow in serum-free conditions. One adaptation approach is to culture such host cells in serum containing media and repeatedly exchange 80% of the culture medium for the serum-free media so that the host cells learn to adapt in serum-free conditions (see, e.g., Scharfenberg, K. et al. (1995) Animal Cell Technology: Developments Towards the 21st Century (Beuvery, E. C. et al., eds), pp. 619-623, Kluwer Academic publishers).

A target polypeptide according to the described embodiments may be secreted into the medium and recovered and purified therefrom using a variety of techniques to provide a degree of purification suitable for the intended use. For example, the use of a target polypeptide (e.g., an antibody or Fc-fusion protein) for the treatment of human subjects typically mandates at least 95% purity as determined by reducing SDS-PAGE, more typically 98% or 99% purity, when compared to the culture media comprising the target polypeptide. In the first instance, cell debris from the culture media can be removed using centrifugation followed by a clarification step of the supernatant using e.g., microfiltration, ultrafiltration and/or depth filtration. Alternatively, a target polypeptide can be harvested by microfiltration, ultra-filtration or depth filtration without prior centrifugation. A variety of other techniques such as dialysis and gel electro-phoresis and chromatographic techniques such as hydroxy-apatite (HA), affinity chromatography (optionally involving an affinity tagging system such as polyhistidine) and/or hydrophobic interaction chromatography (HIC) (see, U.S. Pat. No. 5,429,746) are available. In one embodiment, a target polypeptide such as an antibody or Fc-fusion, follow-ing various clarification steps, is captured using Protein A or G affinity chromatography followed by further chromatog-raphy steps such as ion exchange and/or HA chromatogra-phy, anion or cation exchange, size exclusion chromatogra-phy and ammonium sulphate precipitation. Various virus removal steps may also be employed (e.g., nanofiltration using, e.g., a DV-20 filter). Following these various steps, a purified preparation comprising at least 10 mg/ml or greater, e.g., 100 mg/ml or greater of the target polypeptide described herein is provided.

Other aspects of the disclosure relate to a clonal popula-tion of producer cells that express a FACS selectable poly-peptide and a target polypeptide obtainable by a method as described herein. In some embodiments, the clonal popula-tion yields a 3- to 30-fold, 5- to 30-fold, 5- to 20-fold, 3- to 20-fold, 5- to 10-fold, 3- to 10-fold, or 3- to 5-fold improve-ment in production of the target polypeptide compared to that of the heterogeneous population of producer cells in (a) (e.g., a 3- to 30-fold, 5- to 30-fold, 5- to 20-fold, 3- to 20-fold, 5- to 10-fold, 3- to 10-fold, 3- to 5-fold, or 1.2- to 5-fold improvement compared to the average production of the target polypeptide in the heterogeneous population of producer cells).

IV. Methods of Increasing Viability of Cells after FACS

Other aspects of the disclosure relate to a method of increasing viability of cells after fluorescence activated cell sorting (FACS). In some embodiments, the method com-prises using a first round of FACS to select based on a viability marker a first sub-population of cells from a population of cells expressing a target polypeptide, and using a second round of FACS to select based on the viability marker a second sub-population of cells from the first sub-population of cells, wherein the first round and second round of FACS occur within 8 hours (e.g., within 8, within 7, within 6, within 5, within 4, within 3, within 2, or within 1 hour, or within 60 minutes or within 30 minutes) of each other.

In some embodiments, the viability marker is a forward scatter/side scatter population differentiation and/or a pro-pidium iodide stain.

In some embodiments, the second sub-population has a post sort viability improvement of 1.2- to 4-fold, 2- to 4-fold, or 3- to 4-fold compared to the initial sub-population post sort viability.

In some embodiments, the viability of the cells subjected to the method is greater than 75%, greater than 80%, greater than 85%, or greater than 90% viability (e.g., 90% of cells contain or display the viability marker after the performance of the method).

In some embodiments of any one of the methods, the method further comprises expanding the second sub-popu-lation. In some embodiments of any one of the methods, the method further comprises individually culturing cells from the second sub-population in order to generate one or more clonal populations. In some embodiments, the method of increasing viability of cells after fluorescence activated cell sorting (FACS) is performed after a batch selection method as described herein (see, e.g., Section II above). In some embodiments, the cells express a target polypeptide and a FACS selectable marker as described herein. In some embodiments, the method further comprises isolating the target polypeptide.

It will be readily apparent to those skilled in the art that other suitable modifications and adaptations of the methods described herein may be made using suitable equivalents without departing from the scope of the embodiments dis-closed herein. Having now described certain embodiments in detail, the same will be more clearly understood by reference to the following examples, which are included for purposes of illustration only and are not intended to be limiting.

EXAMPLES

The present invention is further illustrated by the follow-ing examples which should not be construed as further limiting.

Example 1: Introduction to Flare Technology

FLARE (FLow cytometry Attenuated Reporter Expres-sion) is a cell line generation process used previously for 1) cell sorting to isolate clones and 2) clone screening (see, e.g., Cairns, V. et al. (2011) Utilization of Non-AUG Initiation Codons in a Flow Cytometric Method for Efficient Selection of Recombinant Cell Lines. Biotechnol Bioeng 108(11): 2611-2622). In the FLARE system, a cell surface reporter open reading frame (ORF) utilizing a non-ATG initiation codon is located immediately upstream of a gene encoding a protein interest (e.g., an antibody or fusion protein of interest) ORF. The two ORFs are transcribed as a single mRNA but are translated independently (FIG. 1). Without wishing to be bound by any theory, scanning ribosomes recognize the non-AUG initiating codon at a very low frequency (UUG has approximately 1% the initiation capac-ity as compared to AUG) while the majority of ribosomes continue scanning to the primary AUG initiating codon of the protein of interest. This results in low level expression of the cell surface reporter and relatively high level expression of the protein of interest. The bi-cistronic mRNA containing 2 ORFs ensures that cell surface reporter expression is predictive of the protein of interest expression.

Cells expressing a protein of interest with the FLARE system are assessed by flow cytometry to determine levels of a cell surface reporter (CD52 in this example) which are predictive of protein of interest titers. Cells are stained with FITC anti-CD52 mAb and acquired on a flow cytometer. Protein of interest expressing cells will have a level of reporter expression that can be visualized in a histogram overlay and measured in relative fluorescence units (RFU, FIG. 2).

Figure 3:
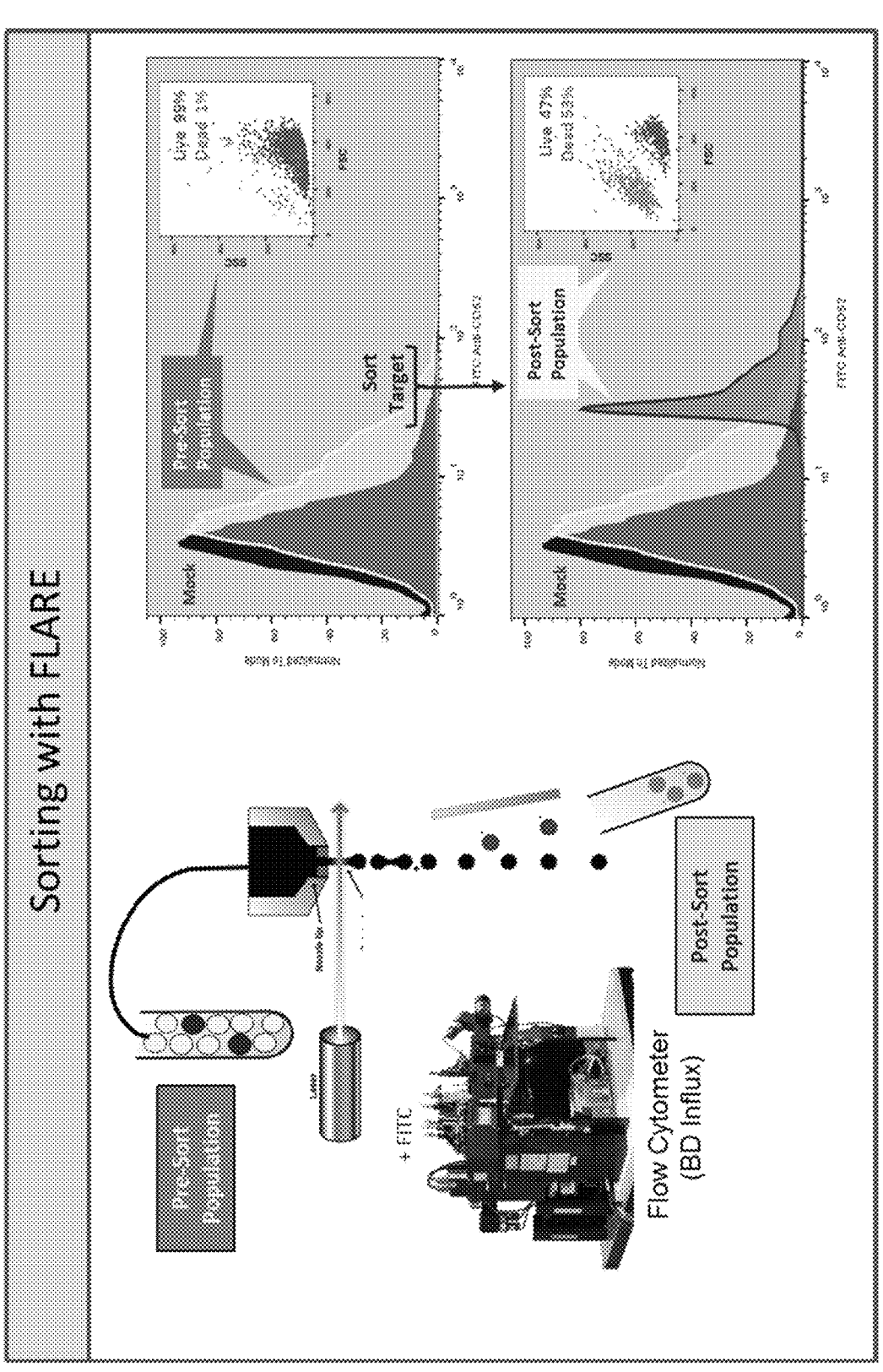
FIG. 3 is a diagram showing fluorescence activated cell sorting (FACS) with FLARE to enrich for cells expressing high levels of the reporter protein.
Figure 4:
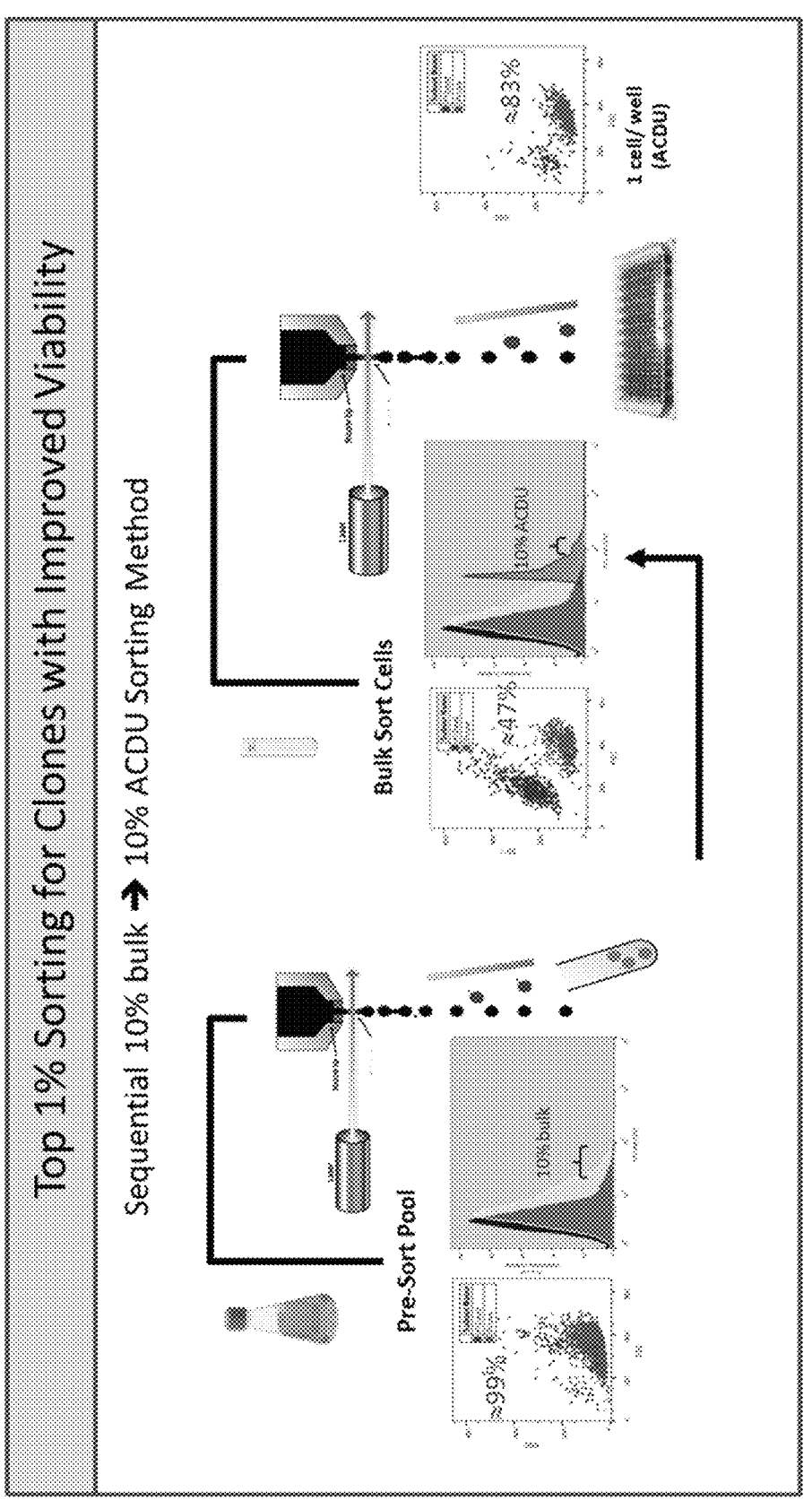
FIG. 4 is a diagram showing immediate repetitive sorting with FACS to improve viability of post sort populations and therefore improve cloning efficiencies.

The FLARE system can also be used with a cell sorter to identify and isolate individual high expressing cells from a diverse expression population to be collected as either a bulk enriched pool or plated as individual cells in a 96-well plate format (FIG. 3 and FIG. 4). Sorting can assess and collect millions of cells in a short time period making it an extremely high throughput method. Sort enriched cells can be collected as a post-sort population and assessed for enrichment and viability.

Figure 5:
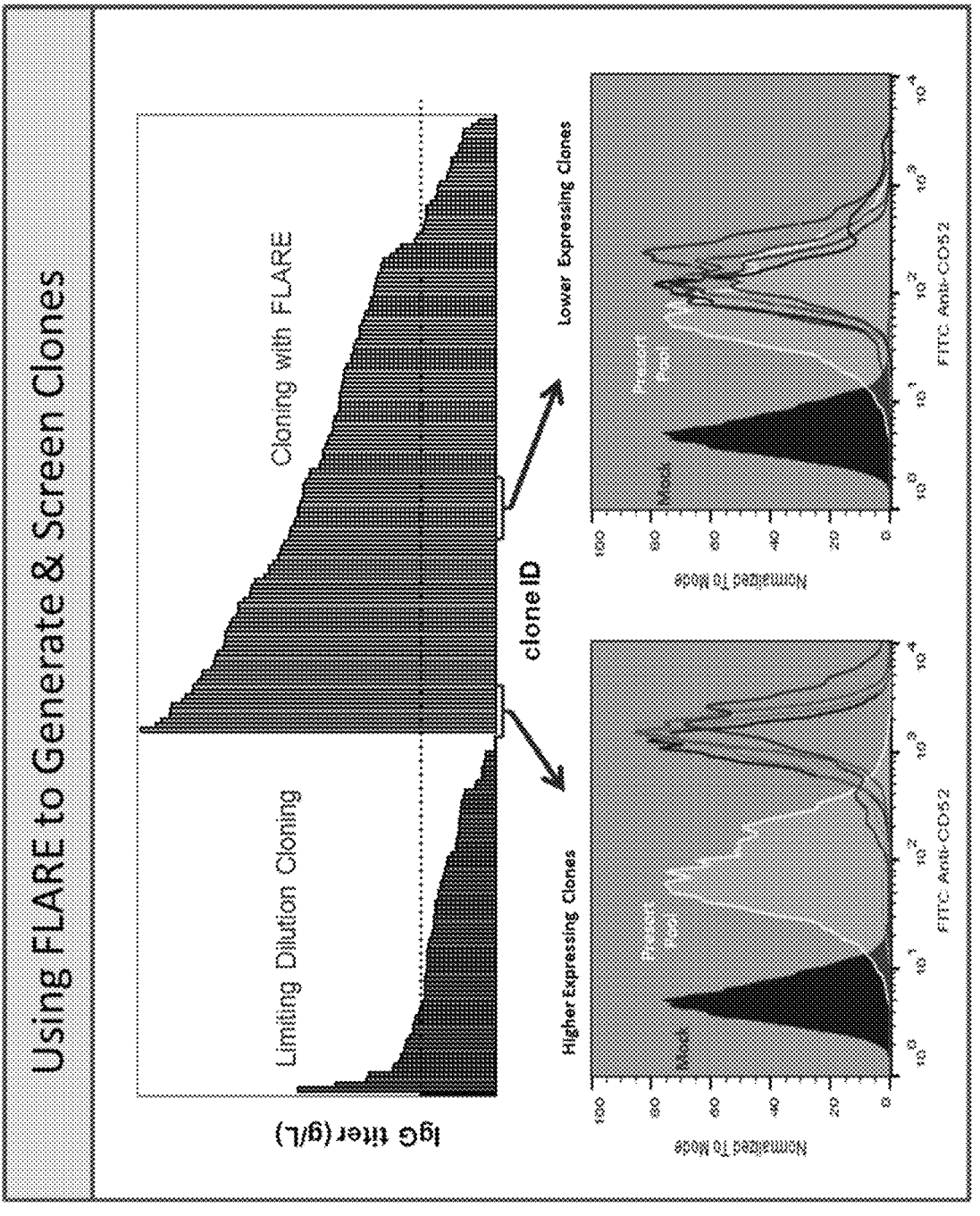
FIG. 5 is a diagram showing use of FLARE to generate and screen clones that express high levels of an IgG; which is superior to that of limited dilution cloning (LDC).

Clones generated by sorting with FLARE yield a group of clones with a greater frequency of high producers than Limiting Dilution Cloning methodologies. FLARE generated clones have a wide range of productivity with the highest expressing clones showing the most robust reporter expression (FIG. 5). Individual clones may therefore be assessed very early (in 96-well plate expansion stage) using the FLARE system to eliminate the less productive clones in a screening step based on reporter expression.

Example 2: Rapid Bulk Sorting Using Flare

Figure 6:
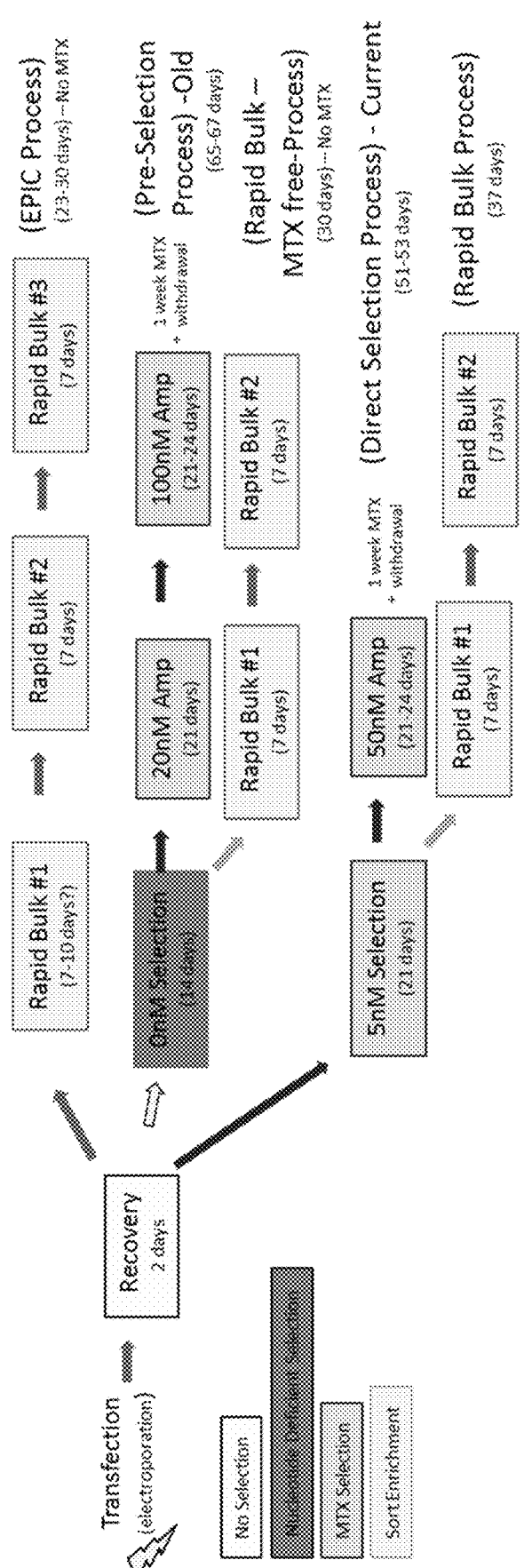
FIG. 6 is a diagram showing multiple alternative methods using rapid bulk sorting (versus standard MTX selection methods) to generate pools of producer cells that express high levels of a protein of interest. Cells are transfected by electroporation, allowed to recover for 2 days, and then are subjected to a selection strategy or sort methodology to generate the pools of producer cells.

Using the FLARE technology discussed in Example 1, several sorts of bulk-enriched cells were generated by targeting a large top percentage (top 5-20%) of transfected cells with a high collection quantity (500,000-3 million cells) for rapid expansion to a higher producing population (FIG. 6). These larger % sorts (e.g. 5%, 10%) allow for a larger number of enriched cells to be rapidly collected and expanded to healthy populations, which can in turn be used for production or to generate clones. Previously utilized methods to increase productivity of the target polypeptide relied on the use of serially increasing amounts of methotrexate (MTX) to select for cells that expressed high levels of DHFR (see Less Stringent Process or Direct Selection Process in FIG. 6). Selection of cells expressing high levels of DHFR increases the likelihood of the protein of interest also being expressed at a high level. MTX selection, unfortunately, is a rather slow process generally taking at least 50 days to generate pools that express the protein of interest at a high level (FIG. 6, Less Stringent Process or Direct Selection Process) suitable for use to generate clones. In contrast, by utilizing FACS sorting and the FLARE system either with minimal selection or no selection (see EPIC Process, MTX Independent (Indy) Rapid Bulk Process, or Rapid Bulk Process in FIG. 6), a faster and more productive method of generating cell populations that are enriched for higher expression of the protein of interest can be achieved. These enriched cell populations are useful for clone generation for large-scale manufacturing of biologics and also for early batch supply of biologics, e.g., to perform preliminary testing of potentially relevant clinical candidates.

For rapid bulk sorting, ADC-free CHO 8D6 DXB11 Parental Host cells were transfected by electroporation with a pGZ729 FLARE vector that either encoded an IgG heavy chain or a Fc-fusion protein as previously described (Cairns, V. et al. (2011) Utilization of Non-AUG Initiation Codons in a Flow Cytometric Method for Efficient Selection of Recombinant Cell Lines. Biotechnol Bioeng 108(11):2611-2622). Each FLARE vector contained two ORFs driven by a single beta-actin promoter upstream of the two ORFs and a single SV40 polyadenylation site downstream of the two ORFs. In each FLARE vector, the upstream ORF encoded a CD52 reporter gene with a UUG start codon. The CD52 reporter gene was further optimized by modifying all internal AUG start codons in any frame and all internal non-AUG start codons within a Kozak context in any frame within the CD52 ORF. The AUG start codon of CD52 was replaced with a single non-AUG start codon (UUG) within a Kozak consensus sequence. The downstream ORF encoded either an IgG heavy chain or a sFc-fusion protein with a AUG start codon. The FLARE vector encoding the IgG heavy chain was co-transfected in the CHO cells with a second vector encoding an IgG light chain in order to produce a monoclonal antibody (mAb). Each FLARE vector further contained an independent dihydrofolate reductase (DHFR) expression cassette. The cell populations were selected prior to the rapid bulk sort by treatment in 5 nM or 50 nM MTX, which eliminated cells that did not express or had low level expression of DHFR.

The pGZ729 FLARE vector backbone sequence is shown below, followed by annotations of the sequence.

```
Sequence of pGZ729 expression vector (SEQ ID NO: 5):
ggatccgctgtgtggaatgtgtgtcagttagggtgtggaaagtccccaggctccccagcaggcagaagtatgcaaagca tgcatctcaattagtcagcaaccaggtgtggaaagtccccaggctccccagcaggcagaagtatgcaaagcatgcat ctcaattagtcagcaaccatagtcccgcccctaactccgcccatcccgcccctaactccgcccagttccgcccattc tccgccccatggctgactaatttttttttatttatgcagaggccgaggccgcctcggcctctgagctattccagaagt agtgaggaggcttttttggaggcctaggcttttgcaaaaagcttgggggggggggacagctcagggctgcgatttcgc gccaaacttgacggcaatcctagcgtgaaggctggtaggattttatccccgctgccatcatggttcgaccattgaac tgcatcgtcgccgtgtcccaaaatatggggattggcaagaacggagacctaccctggcctccgctcaggaacgagtt caagtacttccaaagaatgaccacaacctcttcagtggaaggtaaacagaatctggtgattatgggtaggaaaacct ggttctccattcctgagaagaatcgacctttaaaggacagaattaatatagttctcagtagagaactcaaagaacca ccacgaggagctcattttcttgccaaaagtttggatgatgccttaagacttattgaacaaccggaattggcaagtaa agtagacatggtttggatagtcggaggcagttctgtttaccaggaagccatgaatcaaccaggccacctcagactct ttgtgacaaggatcatgcaggaatttgaaagtgacacgttttcccagaaattgatttggggaaatataaacttctc ccagaatacccaggcgtcctctctgaggtccaggaggaaaaaggcatcaagtataagtttgaagtctacgagaagaa agactaacaggaagatgctttcaagttctctgctcccctcctaaagctatgcattttataagaccatgggactttt gctggctttagatctttgtgaaggaaccttacttctgtggtgtgacataattggacaaactacctacagagatttaa agctctaaggtaaatataaaattttaagtgtataatgtgttaaactactgattctaattgtttgtgtattttagat tccaacctatggaactgatgaatgggagcagtggtggaatgcctttaatgaggaaaacctgtttgctcagaagaaa tgccatctagtgatgatgaggctactgctgactctcaacattctactcctccaaaaaagaagagaaaggtagaagac
```

```
cccaaggactttccttcagaattgctaagttttttgagtcatgctgtgtttagtaatagaactcttgcttgctttgc tatttacaccacaaaggaaaaagctgcactgctatacaagaaaattatggaaaaatattctgtaacctttataagta ggcataacagttataatcataacatactgttttttcttactccacacaggcatagagtgtctgctattaataactat gctcaaaaattgtgtacctttagctttttaatttgtaaaggggttaataaggaatatttgatgtatagtgccttgac tagagatcataatcagccataccacatttgtagaggttttacttgctttaaaaaacctcccacacctcccctgaac ctgaaacataaaatgaatgcaattgttgttgttaacttgtttattgcagcttataatggttacaaataaagcaatag catcacaaatttcacaaataaagcattttttttcactgcattctagttgtggtttgtccaaactcatcaatgtatctt atcatgtctggatcctctacgccggacgcatcgtggccggcatcaccggcgccacaggtgcggttgctggcgcctat atcgccgacatcaccgatggggaagatcgggctcgccacttcgggctcatgagcgcttgtttcggcgtgggtatggt ggcaggccgtggccgggggactgttgggcgccatctccttgcatgcaccattccttgcggcggcggtgctcaacggc ctcaacctactactgggctgcttcctaatgcaggagtcgcataagggagagcgtcgaccgatgcccttgagagcctt caacccagtcagctccttccggtgggcgcggggcatgactatcgtcgccgcacttatgactgtcttctttatcatgc aactcgtaggacaggtgccggcagcgctctgggtcattttcggcgaggaccgctttcgctggagcgcgacgatgatc ggcctgtcgcttgcggtattcggaatcttgcacgccctcgctcaagccttcgtcactggtcccgccaccaaacgttt cggcgagaagcaggccattatcgccggcatggcggccgacgcgctgggctacgtcttgctggcgttcgcgacgcgag gctggatggccttccccattatgattcttctcgcttccggcggcatcgggatgcccgcgttgcaggccatgctgtcc aggcaggtagatgacgaccatcagggacagcttcaaggccagcaaaaggccaggaaccgtaaaaaggccgcgttgct ggcgtttttccataggctccgcccccctgacgagcatcacaaaaatcgacgctcaagtcagaggtggcgaaacccga caggactataaagataccaggcgtttccccctggaagctccctcgtgcgctctcctgttccgaccctgccgcttacc ggatacctgtccgcctttctcccttcgggaagcgtggcgctttctcatagctcacgctgtaggtatctcagttcggt gtaggtcgttcgctccaagctgggctgtgtgcacgaaccccccgttcagcccgaccgctgcgccttatccggtaact atcgtcttgagtccaacccggtaagacacgacttatcgccactggcagcagccactggtaacaggattagcagagcg aggtatgtaggcggtgctacagagttcttgaagtggtggcctaactacggctacactagaaggacagtatttggtat ctgcgctctgctgaagccagttaccttcggaaaaagagttggtagctcttgatccggcaaacaaaccaccgctggta gcggtggtttttttgtttgcaagcagcagattacgcgcagaaaaaaaggatctcaagaagatcctttgatcttttct acggggtctgacgctcagtggaacgaaaactcacgttaagggattttggtcatgagattatcaaaaaggatcttcac ctagatccttttaaattaaaaatgaagttttaaatcaatctaaagtatatatgagtaaacttggtctgacagttacc aatgcttaatcagtgaggcacctatctcagcgatctgtctatttcgttcatccatagttgcctgactccccgtcgtg tagataactacgatacgggagggcttaccatctggccccagtgctgcaatgataccgcgagacccacgctcaccggc tccagatttatcagcaataaaccagccagccggaagggccgagcgcagaagtggtcctgcaactttatccgcctcca tccagtctattaattgttgccgggaagctagagtaagtagttcgccagttaatagtttgcgcaacgttgttgccatt gctgcaggcatcgtggtgtcacgctcgtcgtttggtatggcttcattcagctccggttcccaacgatcaaggcgagt tacatgatcccccatgttgtgcaaaaaagcggttagctccttcggtcctccgatcgttgtcagaagtaagttggccg cagtgttatcactcatggttatggcagcactgcataattctcttactgtcatgccatccgtaagatgcttttctgtg actggtgagtactcaaccaagtcattctgagaatagtgtatgcggcgaccgagttgctcttgcccggcgtcaacacg ggataataccgcgccacatagcagaactttaaaagtgctcatcattggaaaacgttcttcggggcgaaaactctcaa ggatcttaccgctgttgagatccagttcgatgtaacccactcgtgcacccaactgatcttcagcatcttttactttc accagcgtttctgggtgagcaaaaacaggaaggcaaaatgccgcaaaaaagggaataagggcgacacggaaatgttg aatactcatactcttcctttttcaatattattgaagcatttatcagggttattgtctcatgagcggatacatatttg aatgtatttagaaaaataaacaaataggggggttccgcgcacatttccccgaaaagtgccacctgacgtctaagaaacc
```

-continued

```
attattatcatgacattaacctataaaaataggcgtatcacgaggcccttttcgtcttcaagaattggggaccaagac agaaccataagccagtgggatagatcagaaatgttccagaggtgggatggggccagagtgcctgcccccttgaaccgt cccagggaccagaggtgacaaagtggcaacacaggtcctgcctgggaatctggtctgctcctacttagtaaagctgc ctggtgtcacacaagaggcccccacttattcctgcacccctggtggtaggtggcgtcttctcccctgcagccaccag gctcccctgagaacactgccggcagtcctcattgacaggcagtattcgctctgccccacccccacctgtgaattgca gggctggcaggtcctcaggcagctggcaaaccgcctgaacaactgagagatacagggccagggccagggcagtcccg tcccccggaggcagggaggggacgtgctgggaaagttctctctctcaggcccaggttggtgactgcagaaggcttct gtcaaatctcttttgtgggaaccacagagtagccctgaacgtgggggtgtgcttccagtatactctggggtcaccct ttccatactggaggcctctgcaacttcaaaatgctctgctaccaacctagcacaaggaagttggtccagcctcccca cgcagggccactgctgcagtccatatatggactaagccttccttggtttcaacacctacactcactgagcccctact atgtgtatgcagagccgagacaggccctgagcatctcatctgaagcacccttcttgcctaaattcagttttctgtca ctttctcccaggaggtgtgtgtccctctaagctaagccaggggtccctcacccctgccccactcccatccctagtgt aggtatcagctgaagagcttcctgagcagaacactcttgggtgctgacattttgataaataggcccatgtttaggag agcaggggtccggggcgggagatcttctctggtggattgagggctccaagaactactctttgagcacgctgcccct cccagagtccccacagcctccagatggactagaacacagttcggctgtggctgcacataactaacagaggatagatg gtgggtcccagcccaacagtgcctggcaatcacccagagccaccagctaacggccttggcttagttttttgcctggg tgtgatcaggcagccctccaaaactgcccggactccatgacaagttttgcttgttctatagagcacagttcctttct aggtctggggcaagggacatcgggagacatcttcctgcaacagctccagtcactggaccaccaggctcgccctgtct ttggtgtgtggccctgagtctcctaagtggcccaaacctgtgaagacccctccaaccacagttttgcttctaaattg taccccaacacacctagcaaattgaaaccccaccagaagtcccccagatctggctttccggctattgctggcaaggg ggagtgactcccggcccattcaatccaggccccgcgtgttcctcaaacaagaagccacgtaaacataaaccgagcct ccatgctgacccttgcccatcgaggtactcaatgttcacgtgatatccacacccagagggtcctggggtgggtgcat gagccccagaatgcaggcttgataaccgagaccctgaatcgggcagtgtccacaagggcggaggccagtcatgcatg ttcgggcctatggggccagcacccaacgccaaaactctccatcctcttcctcaatctcgctttctctctctctctct tttttttttttattttttttttttgcaaaaggagggggagagggggtaaaaaaatgctgcactgtgcggctaggccg gtgagtgagcggcgcggagccaatcagcgctcgccgttccgaaagttgccttttatggctcgagtggccgctgtggc gtcctataaaacccggcggcgcaacgcgcagccactgtcgagtccgcgtccacccgcgagcacaggcctttcgcagc tctttcttcgccgctccacacccgccaccaggtaagcagggacaacaggcccagccggccacagccctcccgtgggc agtgaccgcgctgcagggtcgcggggggacactcggcgcggacaccggggaaggctggagggtggtgccgggccgcgg agcggacactttcagatccaactttcagtccagggtgtagaccctttacagccgcattgccacggtgtagacaccgg tggaccgctctggctcagagcacgcggcttgggggaacccattagggtcgcagtgtgggcgctatgagagccgatg cagctttcgggtgttgaaccgtatctgcccaccttggggggaggacacaaggtcgggagcccaaacgccacgatcatg ccttggtggcccatgggtctttgtctaaaccggtttgcccatttggcttgccgggcgggcgggcgcggcgggcccgg ctcggccgggtggggctgggttgccactgcgcttgcgcgctctatggctgggtattggggcgcgtgcacgctgggg agggagcccttcctcttccccctctcccaagttaaacttgcgcgtgcgtattgagacttggagcgcggccaccgggg ttgggcgagggcggggccgttgtccggaaggggcggggtcgcagcggcttcggggcgcctgctcgcgcttcctgctg ggtgtggtcgcctcccgcgcgcgcactagccgcccgccggcggggcgaaggcggggcttgcgcccgtttggggaggg ggcggaggcctggcttcctgccgtggggccgcctccggaccagcgtttgcctcttatggtaataacgcggccggcct gggcttcctttgtccctgagtttgggcgcgcgccccctggcggcccgaggccgcggcttgccggaagtgggcaggg cggcagcggctgcgcctagtggcccgctagtgaccgcgaccctctttgtgccctgatatagttcgccggatcctac cgcggtagcggccgcgccaccttggagcgcttcctcttcctcctactcaccatcagcctcctcgtttttggtacaaat
```

-continued

```
acaaaccggactctccggacaaaacgacaccagccaaaccagcagcccctcagcatccagcaacataagcggaggca ttttccttttcttcgtcgccaacgccataatccacctcttctgcttcagttgaaggccggccaatacgtaggcgcgc cattgagtgagtgatttggcgcgccaagatatcacacccgggattaattaaaggtacctacgcgtagaattccacgt agtggtttaaactctagatactcgagggatctggatcataatcagccataccacatttgtagaggttttacttgctt taaaaaacctcccacacctcccctgaacctgaaacataaaatgaatgcaattgttgttgttaacttgtttattgca gcttataatggttacaaataaagcaatagcatcacaaatttcacaaataaagcattttttcactgcattctagttg tggtttgtccaaactcatcaatgtatcttatcatgtct
```

Elements of pGZ729 Expression Vector (and Nucleotide Locations):

Nucleotides 1-325—SV40 early promoter (for DHFR transcription)

Nucleotides 347-1089—Dihydrofolate reductase (DHFR) open reading frame

Nucleotides 1090-1934—SV40 early intron and polyA

Nucleotides 2684-3366—*E. coli* ColE1 origin

Nucleotides 3464-4123—Ampicillin resistance gene

Nucleotides 4528-7539—Hamster β-actin promoter (for transcription of gene of interest)

Nucleotides 7568-7753—CD52 open reading frame (containing TTG start codon)

Nucleotides 7781-7791—Stop codons in each of 3 reading frames

Nucleotides 7813-7872—Multiple cloning site (for insertion of target polypeptide with ATG start codon)

Nucleotides 7882-8123—SV40 early polyA

Figure 7:
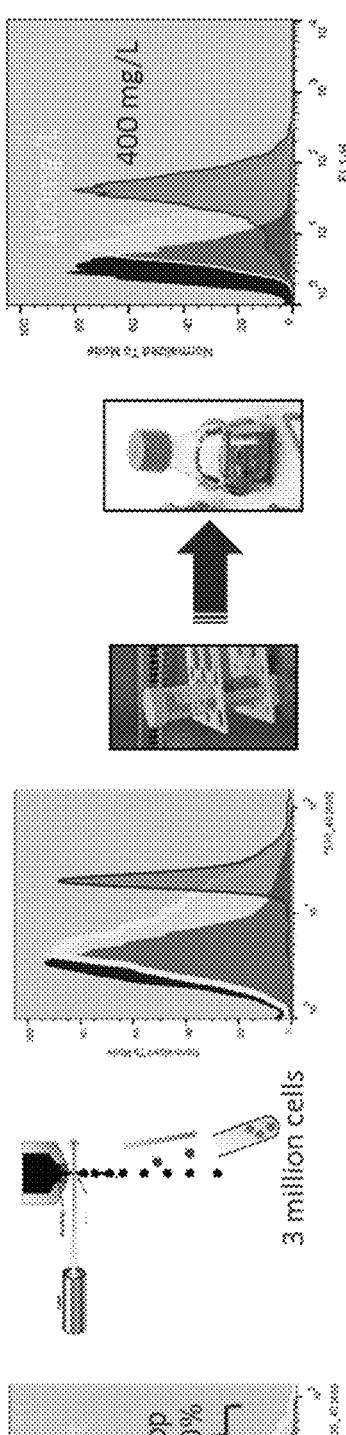
FIG. 7 shows rapid bulk sorting of the top 10% of reporter protein-expressing cells from a pre-sort cell population that had been generated with 5 nM MTX.

Rapid bulk sorting was carried out as follows and is exemplified in FIG. 7:

1. A candidate pool with suitable reporter expression profile (presort pool) was identified
2. The top % of reporter expressing cells in the presort pool were targeted for FACS collection (between 5-20%)
3. A large number of sorted cells was collected as a bulk enriched population (0.5-5.0×10⁶ cells)
4. The bulk sorted pool was quickly expanded to a healthy enriched population (in as little as 1 week)
5. The rapid bulk pool was evaluated for productivity (target polypeptide titer boost over pre-sort pool)

Figure 8:
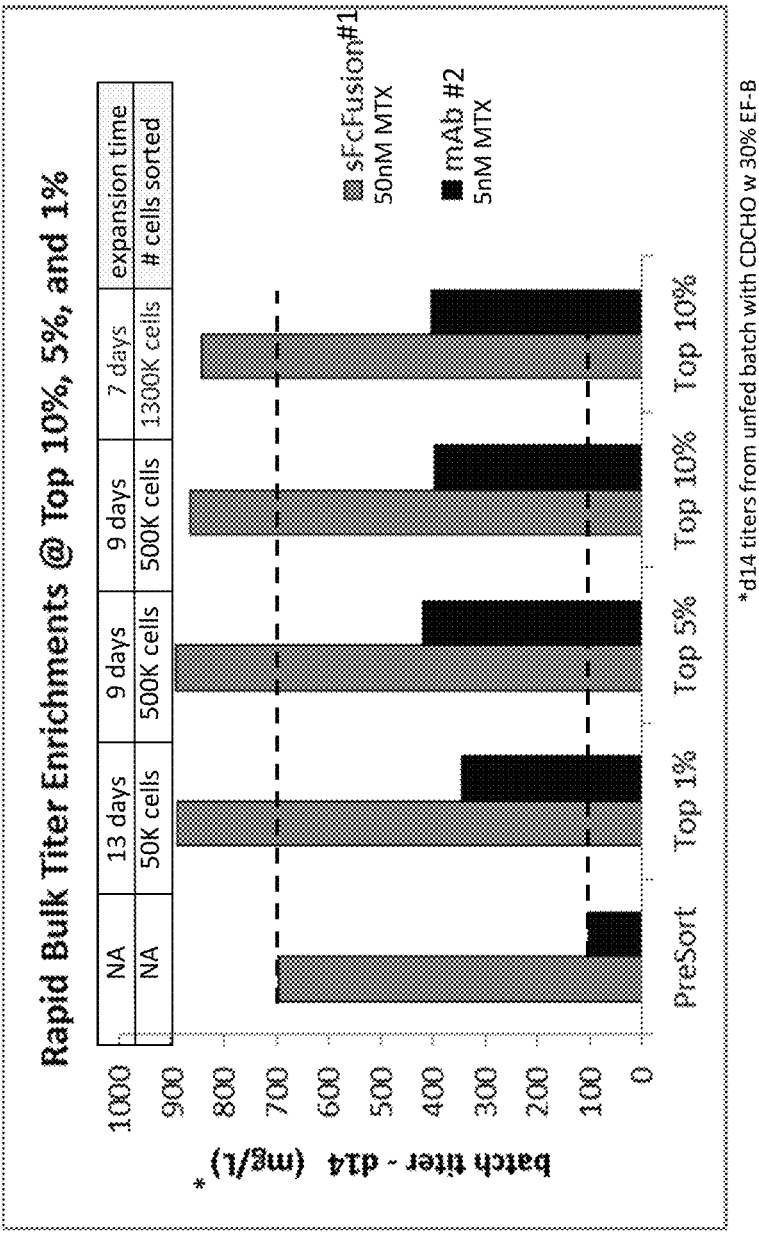
FIG. 8 is a graph showing day 14 batch titer enrichment of proteins of interest (monoclonal antibody, mAb #2, or Fc fusion protein, sFcFusion #1) after rapid bulk sorting which targeted the top 1, 5, or 10% of reporter protein-expressing cells from pre-sort cell populations. Also shown at the top of the graph is the # of cells targeted for sort collection and the time to expand each enriched post-sort population. The titers were from unfed batch cultures.

In one set of experiments, the relationship of different % reporter cut-off (detected by FACS) versus levels of target polypeptide titer enrichments was evaluated using a monoclonal antibody (mAb) protein of interest (a mAb target polypeptide) or a Fc-fusion protein of interest (a Fc-fusion target polypeptide). It was unclear if targeting a broader range of cells with lower reporter expression (e.g., top 5-20%) would also yield significant enrichments in the resulting population. It was possible that after sort enrichment the lower producing cells (which can have more rapid growth rates than higher producing cells) could overtake a population in a pool dynamic and therefore result in a pool with lower than desired productivity. It was theorized that a balance must be struck: target a large enough percentage to collect many cells quickly but not so large to capture lower producing cells which could detrimentally impact the degree of enrichment. Thus, the goal of these experiments was to understand the relationship between the levels of enrichments achievable for the different sort percentages which were being targeted. The results show that sorting for the top 10% and top 5% of reporter expressing cells resulted in a productivity enrichment similar to that of the highly stringent top 1% sort. It particular, it was shown that each of the top 10%, top 5% and top 1% of the presort pool was capable of producing a pool that had up to 4-fold greater target polypeptide titer than the presort pool initially selected with a low level of MTX (FIG. 8 and Table 1).

TABLE 1

Different % cut-off for sorting versus titer of a mAb target polypeptide

| SORT | # of Cells sorted | Expansion time* | Titer of mAb |
|---|---|---|---|
| PreSort | NA | NA | 104 mg/L |
| Top 10% | 500,000 cells | 9 days | 397 mg/L |
| Top 5% | 500,000 cells | 9 days | 415 mg/L |
| Top 1% | 50,000 cells | 16 days | 335 mg/L |

*time from the sort to produce a cell population that contains a number of cells suitable for freezing down, setting up a batch culture and/or resorting (60-80 × 10⁶ cells)

These data suggested that large top percentage targets can be successfully sorted to collect large quantities of cells within a single sort for quick expansion of the resulting pool, which maintained a very high level of enrichment. The speed of this methodology was further demonstrated by repeating the sorts that targeted the top 10% with an even larger number of cells (1.3 million) collected, from which a more productive pool was successfully expanded in only 7 days (FIG. 8).

A high level of enrichment was achieved from these rapid bulk sorts. Rapid bulk sorting a mAb-expressing pool producing only 100 mg/L demonstrated a 4-fold improvement in pool productivity in as little as 7 days (FIG. 8, second top 10% sort). Furthermore, an already very productive pool expressing a Fc-fusion protein at 700 mg/L was enriched by 20% within the same timeframe (FIG. 8). These results demonstrated that rapid bulk sorting with the FLARE system was 1) feasible, 2) fast (limited only by the number of cells one can sort and the recovery of the post-sort population), and 3) highly productive. This rapid bulk sorting was also shown to work with both a mAb and Fc fusion protein and was successful for both high and low productivity starter pools.

Figure 9:
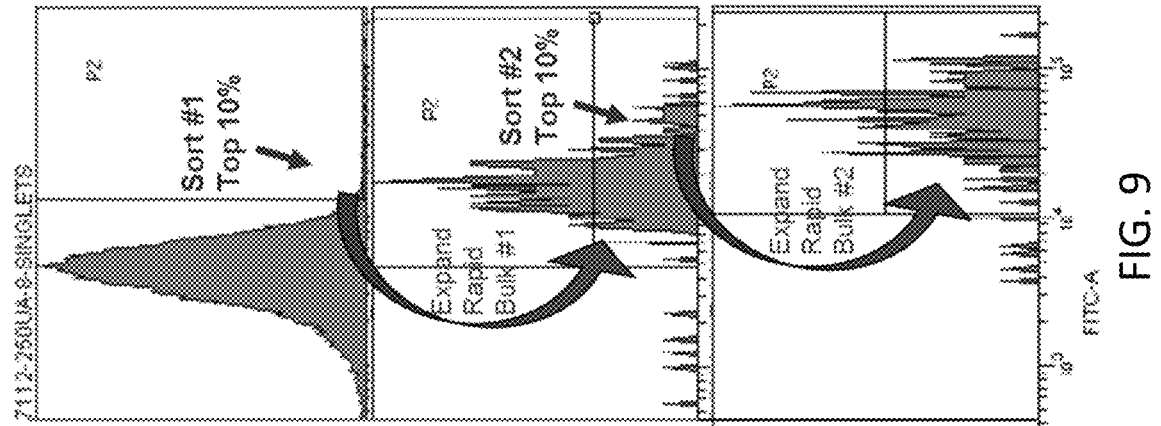
FIG. 9 is a series of diagrams showing methodology for sequential rapid bulk sorting.

Seeing such robust enrichment from a single round of bulk sorting led to the question as to whether MTX was needed at all and in particular if MTX was driving ("amplifying") expression in these cells or simply killing low producing cells. It was hypothesized that if MTX is primarily serving to kill the lower producing cells, then rapid bulk sort enrichments using FLARE could provide a more efficient (faster and at least as productive) and less intrusive methodology to increase productivity of cell populations. In other words, sequential sorts generating a series of rapid bulk pools may be a vehicle to drive expression in a pool independent of MTX. This sequential sort can use the following methodology, which is exemplified in FIG. 9:

1. Generate a pre-sort starter pool by transfection & selection with low level (5 nM) MTX (the selection could also be accomplished using nucleotide-deficient medium alone (0 nM MTX))
2. Rapid bulk sort (top 10%) to generate a stable pool with enhanced expression
3. Repeat (sequentially) rapid bulk sort (top 10%) to generate another stable pool with further enhanced expression This effectively creates a sequential sorting methodology which focuses on isolating the low frequency, high producing cells from a diverse population. This would essentially replace the role of MTX to eliminate low producing cells (by cell death) with cell sorting using the FLARE system to selectively ignore low producing cells and isolate only high producers for continued growth (i.e. enrichment of the cell population for high producers).

A Proof of Concept experiment was established to test this sequential rapid bulk sorting methodology using three 5 nM MTX pools, each expressing a different molecule (mAb #1, mAb #3, and sFc Fusion #2). Each pool was rapid bulk sorted, targeting the top 10%, and expanded in 9-12 days and then rapid bulk sorted again (sequential), targeting the top 10%, and quickly expanded. The resulting pools were set up in batch cultures to assess titer of the target polypeptide. FIG. 10 shows the reporter expression (flow cytometry histogram overlays) and target polypeptide titer for each sort enriched pool relative to the starting 5 nM pool. The data shows that it is possible to sequentially enrich expression through repetitive rapid bulk sorting.

Figure 11:
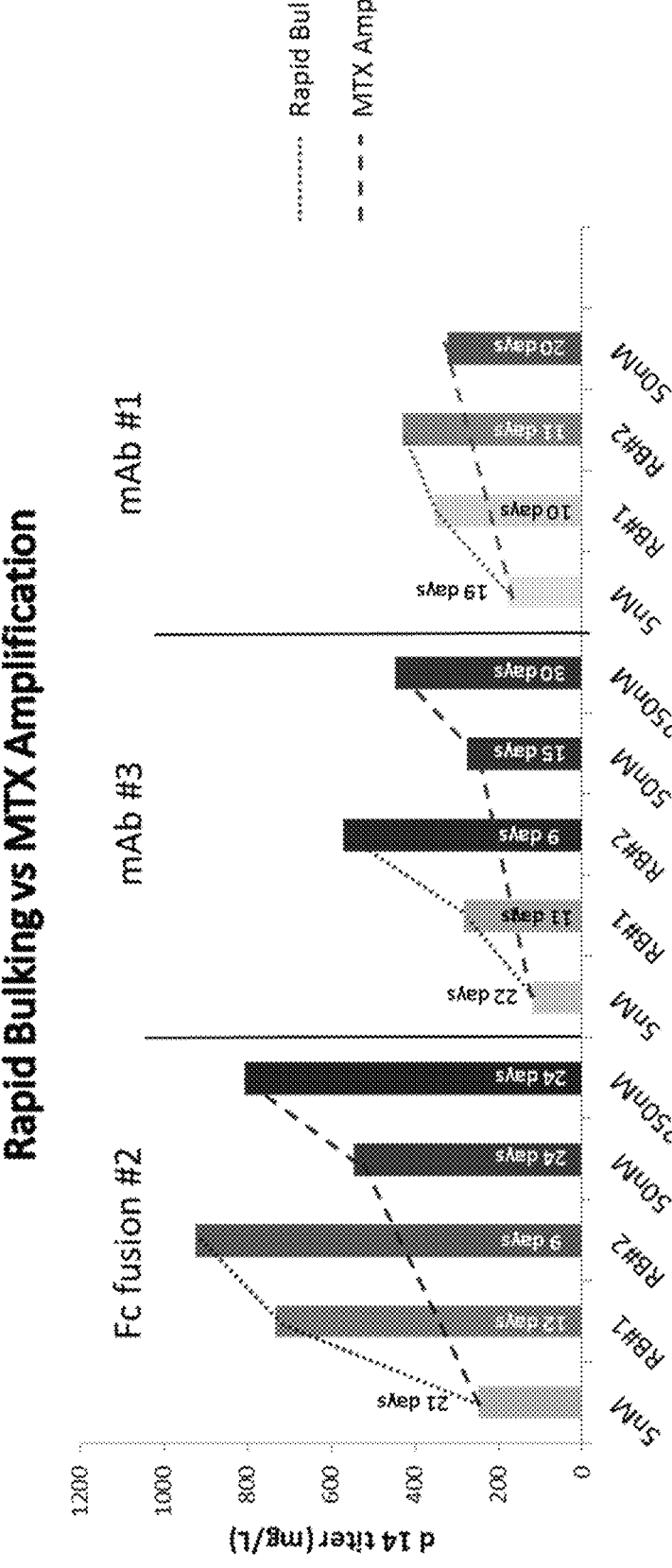
FIG. 11 is a graph of day 14 batch titer of Fc fusion protein or monoclonal antibodies in cell pools produced by sequential rapid bulk sorting or MTX amplification.

To enable a comparison to a "traditional" MTX selection procedure for generation of high producing pools, each starting 5 nM pool was also subjected to two additional rounds of MTX selection (50 nM and 250 nM; FIGS. 11 and 15). As shown in FIGS. 11 and 15, not only did the sequential rapid bulk sorts achieve significantly better titers of target polypeptides than both the 50 nM and 250 nM MTX selections but each rapid bulk sort (with the exception of mAb #3 RB #1) was generated 2-3 times faster than each corresponding round of MTX amplification.

Figure 13:
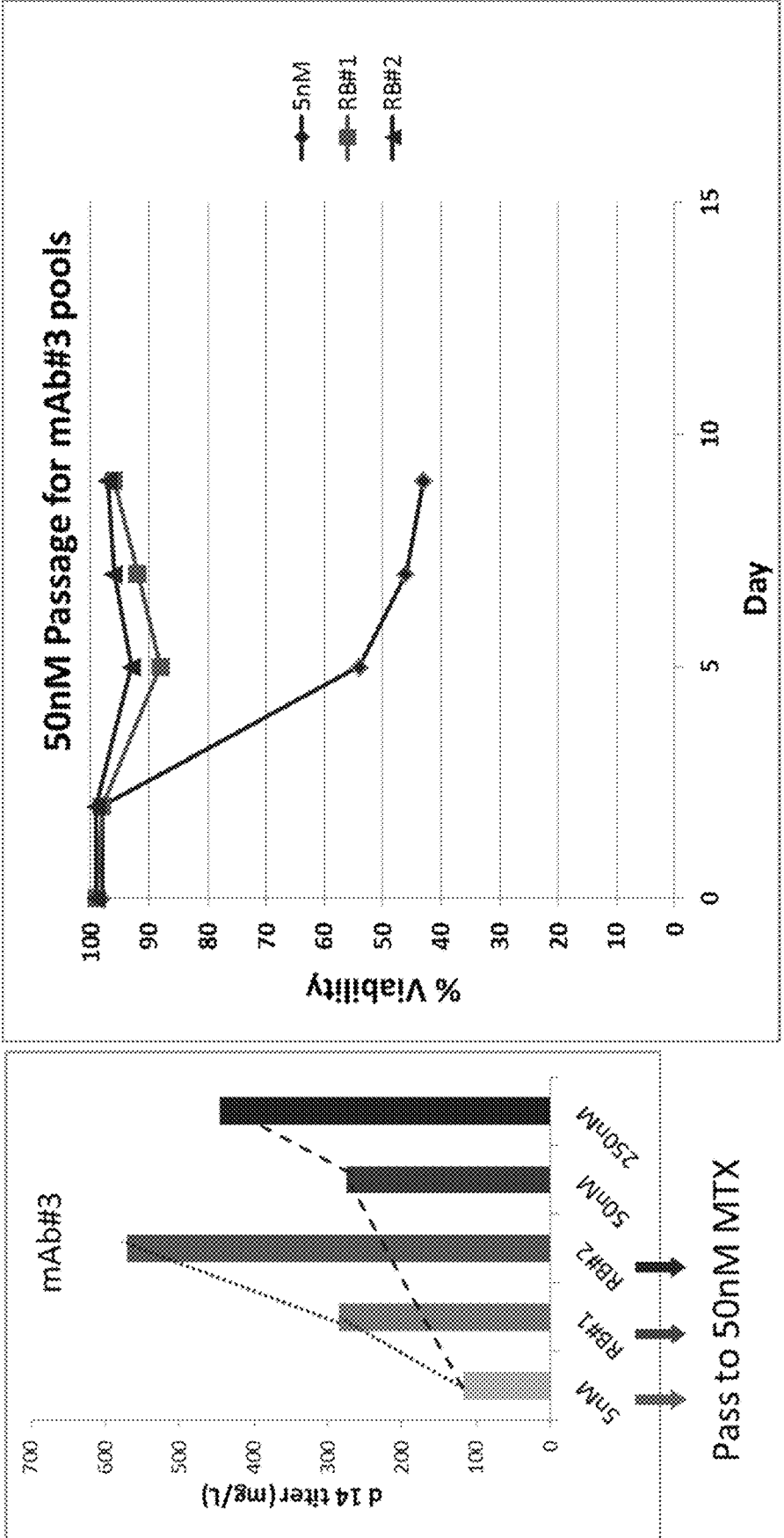
FIG. 13 is two graphs, the left graph showing the 14 day titer of a monoclonal antibody and the right graph showing % viability of cells expressing the monoclonal antibody, which had been generated by rapid bulk sorting or 5 nM MTX selection, after passage with 50 nM MTX.

The significant degree of improvement over MTX selection was unexpected and again suggested that MTX was not as critically important for amplifying expression as previously believed. It was hypothesized that the sequentially sorted rapid bulk enriched populations may be less affected by a higher MTX concentration due to their significant enrichments of gene expression. To test this each rapid bulk pool was seeded into growth media with 50 nM MTX and the culture viability was compared to that of the starting 5 nM MTX pool seeded into the same 50 nM MTX media. The results are shown in FIGS. 12-14.

Although it was hypothesized that there would be some resistance of the rapid bulk pools to 50 nM MTX, the rapid bulk pools for sFc Fusion #2 and mAb #3 showed little to no impact of 50 nM MTX whatsoever (FIGS. 12 and 14). For mAb #1, the first rapid bulk pool declined in viability similarly to the 5 nM MTX starting pool, but began recovering earlier than the 5 nM pool, and the second rapid bulk pool declined in viability but was significantly less affected by 50 nM MTX as compared to 5 nM MTX pool (FIG. 13). These results are strong evidence that MTX amplification is not required to amplify pool expression and that perhaps its role is simply that of killing lower producing cells.

Clones were generated from both MTX amplified pools (5 nM and 50 nM MTX) and from rapid bulked pools (RB #1 and RB #2) expressing mAb #1 to comparatively evaluate productivities. Clones were generated using FLARE as previously described (see, e.g., Cairns, V. et al. (2011) Utilization of Non-AUG Initiation Codons in a Flow Cytometric Method for Efficient Selection of Recombinant Cell Lines. Biotechnol Bioeng 108(11):2611-2622). Briefly, FLARE was used to isolate and single cell plate the top 1-3% of reporter-expressing cells from each pool using FACS. Expanded clones were then screened (taking top 25-30% positive expressers), again using FLARE, to identify only the top tier clones to expand for target polypeptide titer evaluation. As shown in FIG. 22, rapid bulk sorting generated clones from RB #1 and RB #2 pools expressing mAb #1 which were comparable to those generated from both 5 nM and 50 nM MTX amplified pools. Top rapid bulk clone titers where achieved at 1.4 g/L and 1.6 g/L for RB #1 and RB #2 respectively. Top MTX amplified clone titers where achieved at 1.2 g/L and 1.9 g/L for 5 nM and 50 nM respectively. While top clone performance and frequency of top producers was slightly greater in 50 nM MTX generated clones, it is believed the rapid bulk generated clones may demonstrate a more robust profile in stability studies as MTX concentrations used are 10 fold lower and removed during cloning process.

In conclusion, sequential rapid bulk sorting from 5 nM MTX pools were shown to be a viable alternative to a direct selection process using MTX. Sequential rapid bulk sorting was shown to be faster (timeline difference of up to 2-3 weeks), to use less MTX (potentially resulting in more robust and stable clones), to be more productive (significantly better pool titers of target polypeptides were achieved), and to work with 3 different target polypeptides (2 different mAbs and a Fc fusion protein).

Example 3: Fully MTX Independent Sequential Rapid Bulk Sorting

Next, a fully MTX-independent rapid bulk method was tested. The test starter pools expressed a Fc Fusion Protein (sFcF #2). Two starter pools were established by initial selection of transfected cells with nucleotide deficient media (CD CHO Medium, Gibco, Life Technologies, Catalogue number 10743) supplemented with glutamine (i.e. 0 nM MTX) for 21 days. In this process, stably transfected cells were placed into a nucleotide deficient media for lower stringency selection of the DHFR expression cassette. Nucleotide-deficient initial selection without MTX generally yields lower expressing pools in slightly shorter timeframes (generally this is not preferred in standard MTX expression platforms because it generates a larger percentage of lower expressing cells which eventually need to be killed in later rounds of MTX amplifications).

For the first sort, the 0 nM MTX pool was rapid bulk sorted (top 10%) and $3\text{-}4 \times 10^6$ cells were collected as Rapid Bulk #1. The cell population of Rapid Bulk #1 was allowed to expand for 8 days and was then re-sorted as described below and was set up as a batch culture for target polypeptide titer evaluation and for FACS analysis for reporter expression. For the second sort, the expanded Rapid Bulk #1 pool was rapid bulk sorted (top 10%) and $3\text{-}4 \times 10^6$ cells were collected as Rapid Bulk #2. The cell population of Rapid Bulk #2 was allowed to expand for 8 days and was then set up as a batch culture for target polypeptide titer evaluation and for FACS analysis for reporter expression. This process was performed for the second 0 nM MTX pool, resulting in two separate Rapid Bulk #1 and #2 populations.

Figure 2:
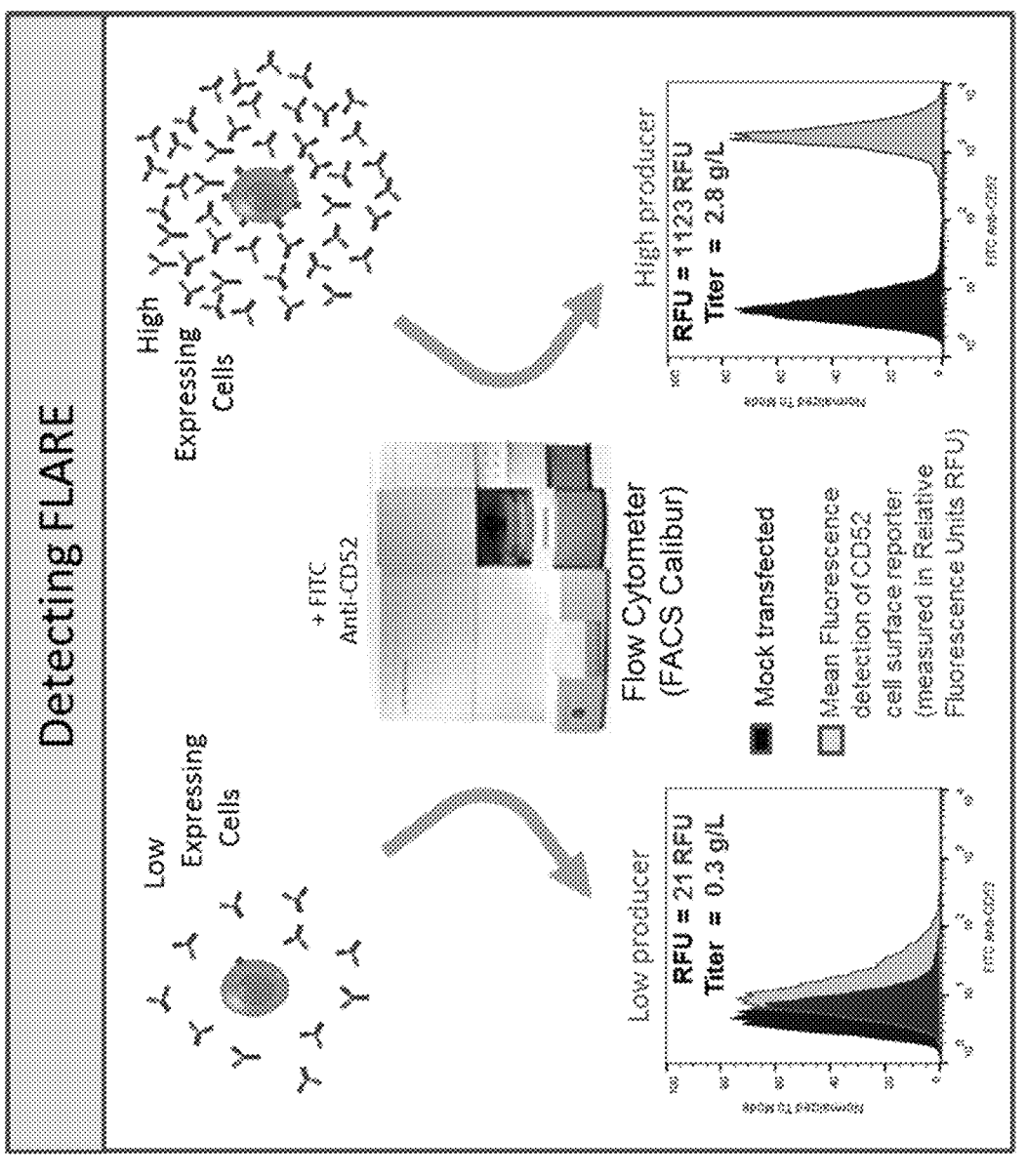
FIG. 2 is a diagram showing how FLARE can be used to identify low or high producer populations of cells.
Figure 16:
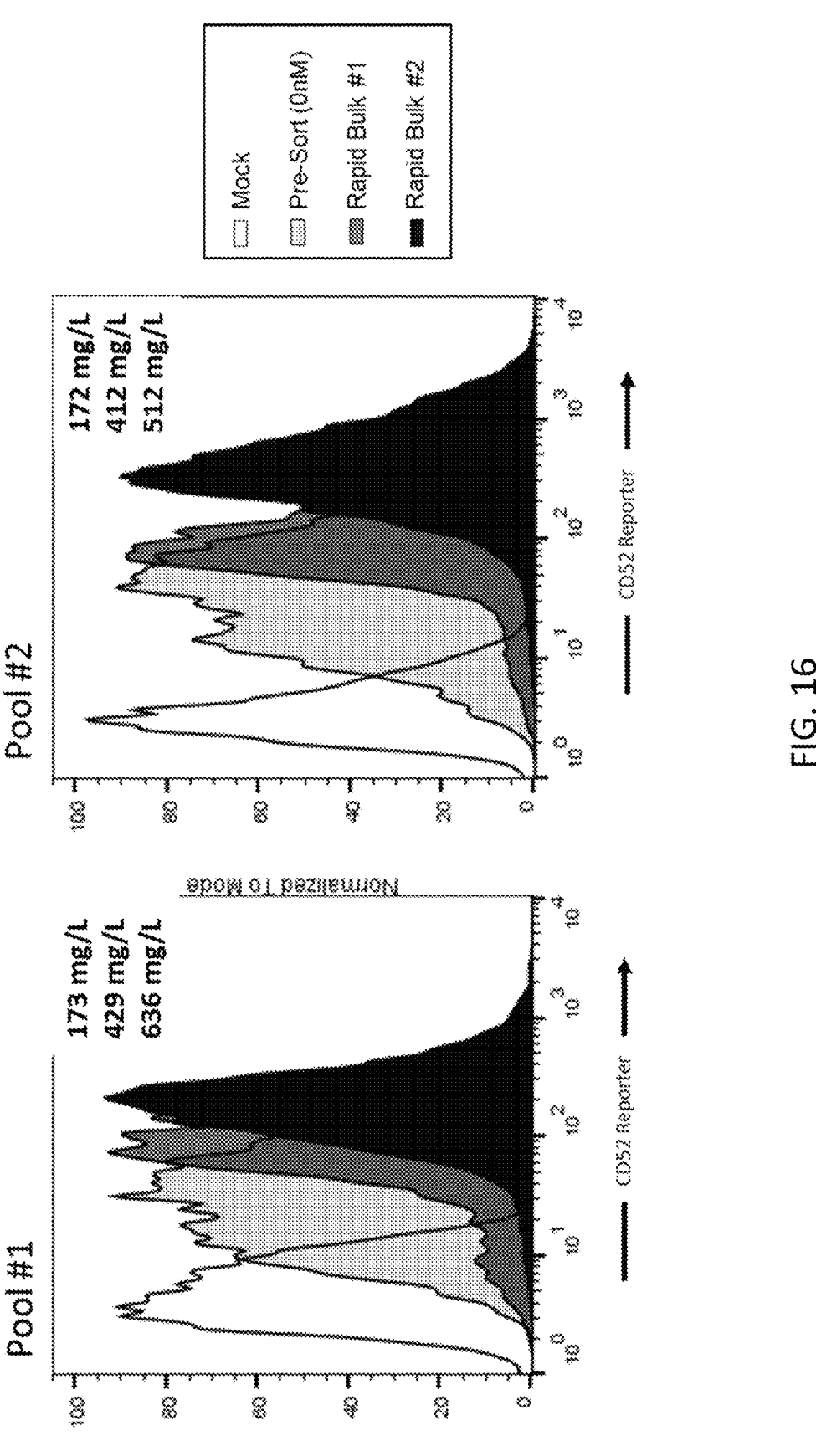
FIG. 16 is two FACS histogram overlays showing flow cytometry data from cells initially selected with nucleotide deficient medium (0 nM MTX) and subjected to two rounds of rapid bulk sorting and showing the respective day 14 titers of the protein of interest.
Figure 17:
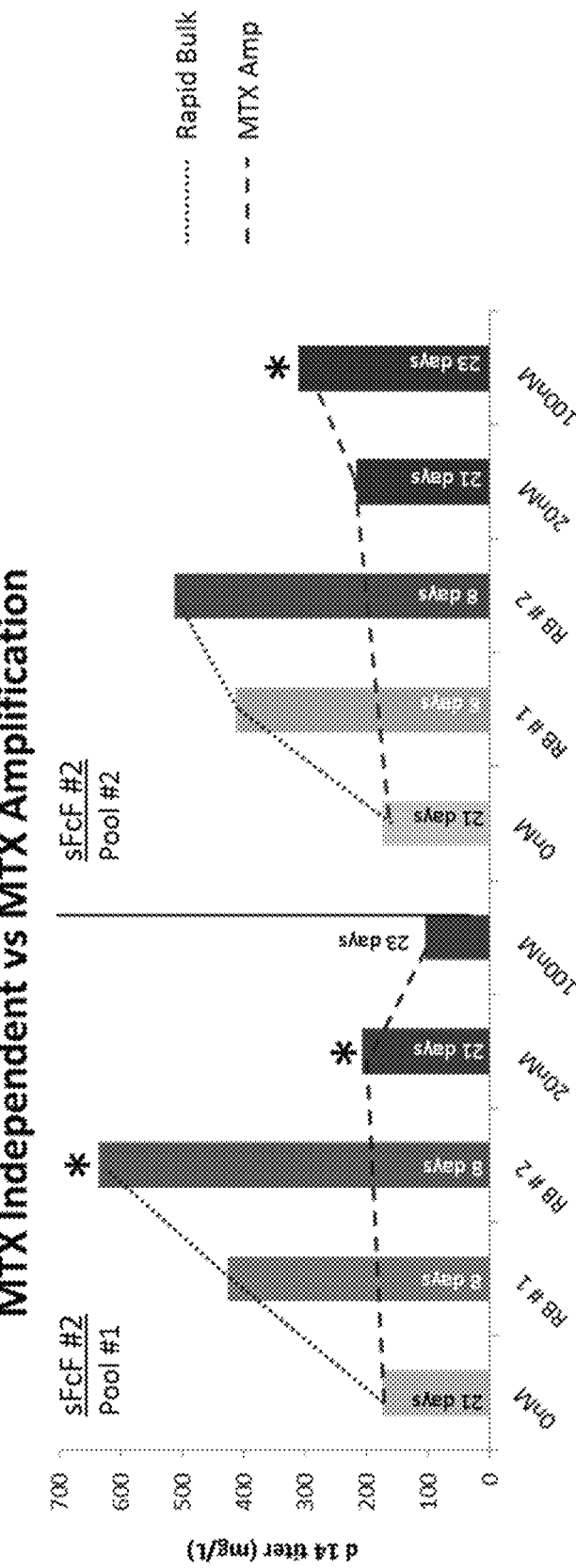
FIG. 17 is a graph comparing the 14 day titer of cell populations produced by MTX independent sorting or by MTX amplification.

As shown in FIGS. 16 and 17, 2 rounds of rapid bulk sorting after selection with a nucleotide deficient medium (0 nM MTX) generated pools producing 0.51 g/L and 0.64 g/L (in unfed batch culture) in only 16 days, compared to 0.17 g/L productivity of the pre-sort 0 nM MTX pool. To put these results into context with MTX selection, these same two 0 nM MTX pools were also separately MTX amplified using the standard amplification paradigm (0 nM MTX, followed by 20 nM MTX, then followed by 100 nM MTX). Both pools took 21 days to complete 20 nM MTX selection while only yielding modest gains in target polypeptide titer to just over 0.2 g/L (FIG. 17). When further amplified to 100 nM MTX, taking an additional 23 days for selection, one pool declined in expression and the other pool only increased in productivity to 0.31 g/L (FIG. 17). In other words, the productivity of the MTX selected pools did not even surpass that of the first rapid bulk pool generated from the respective starting pool.

Figure 19:
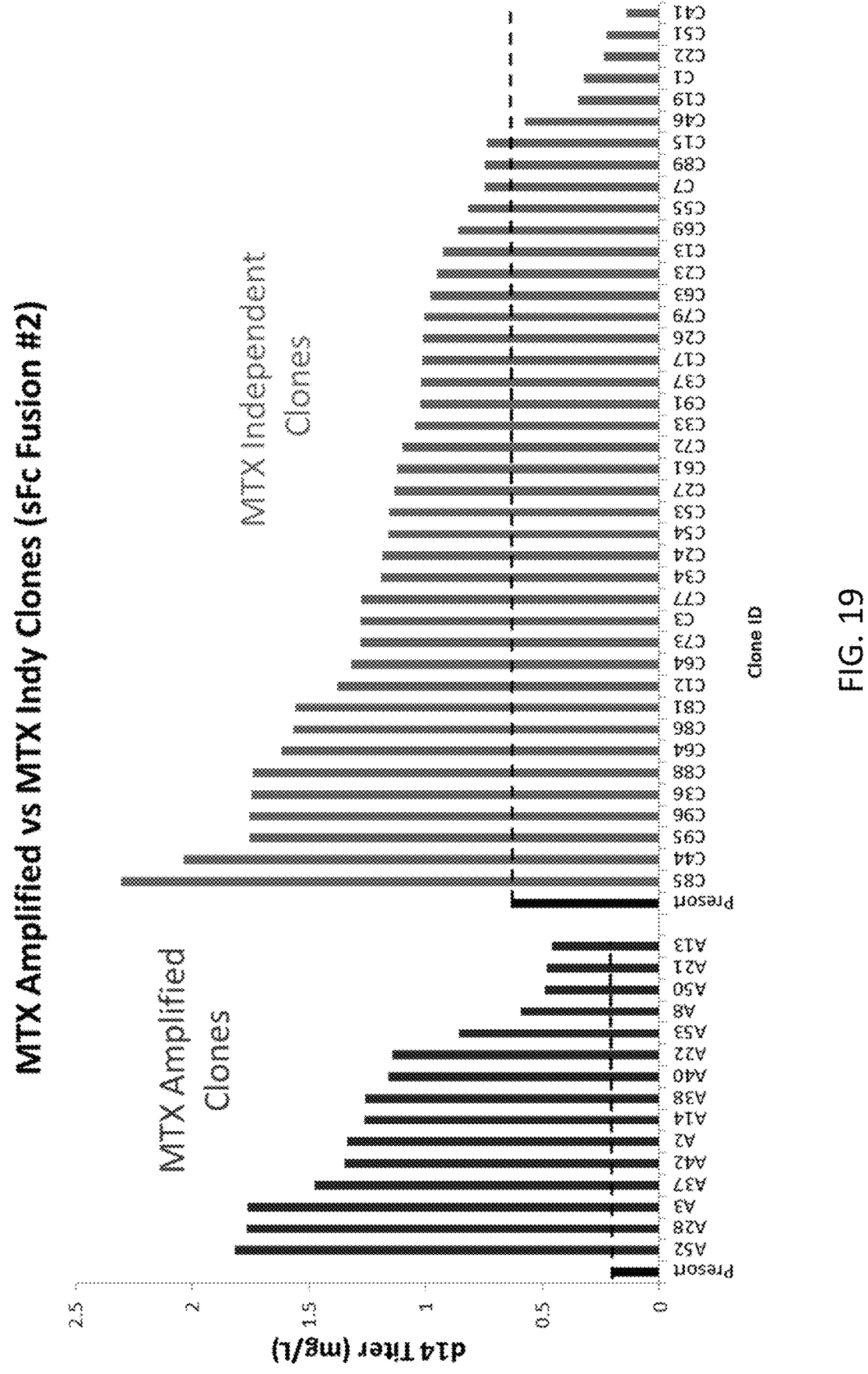
FIG. 19 is two graphs showing 14 day titer of a Fc fusion protein from clones produced by MTX amplification or MTX independent sorting.

At this point, the data showed that highly productive pools could be generated with this new methodology, which could also be used for material production early in development of a clinical protein biologic. The next question was whether the clones these pools could generate would outperform the MTX-generated clones. To test this, the best MTX independent pool and two of the best MTX selected pools were selected to generate clones (pools indicated by asterisks in FIG. 17). Clones were generated using FLARE as previously described (see, e.g., Cairns, V. et al. (2011) Utilization of Non-AUG Initiation Codons in a Flow Cytometric Method for Efficient Selection of Recombinant Cell Lines. Biotechnol Bioeng 108(11):2611-2622). Briefly, FLARE was used to isolate and single cell plate the top 1% of reporter-expressing cells from each pool using FACS. Expanded clones were then screened, again using FLARE, to identify only the top tier clones to expand for target polypeptide titer evaluation. As shown in FIGS. 18 and 19, MTX independent clones yielded as much as 2.3 g/L in unfed batch. FIG. 18 also shows that cloning efficiency and clone survivability was higher in the MTX independent sort.

In conclusion, these results show that the fully MTX independent rapid bulk method is a very attractive alternative to MTX direct selection. The fully MTX independent rapid bulk method was faster (with a timeline saving of up to 4 weeks and no need for MTX withdrawal prior to sorting), was performed without the use of MTX, and was more productive (higher pool titers compared to MTX pools, and high titer clones comparable to or slightly better than MTX selected clones).

There are many implications of a drug independent cell line generation system. Firstly, these results are surprising in view of the long-accepted dogma that MTX is required to drive DHFR expression in some CHO lines. Secondly, if batch sort enrichments using FLARE can pull out rare, low frequency, highly expressing cells while circumventing a drug selection system like MTX/DHFR, it is expected that this methodology will also work for other drug selectable systems like the MSX/GS system. Thirdly, it is hypothesized that removal of DHFR from the FLARE expression cassettes may allow for true independence from a selectable marker which is tied to cell survivability. Gaining this level of independence from drug selectable systems may also untether the expression system from CHO cells altogether and open up a much broader tool box of animal host cells.

Example 4: Early Post-Transfection Isolation of Cells (EPIC)

Next, the feasibility of a method of sorting was explored which aims to target an unselected transfected early-expressing population for enrichment prior to selection. This method of sorting is called "short sorting" or EPIC (Early Post-transfection Isolation of Cells) and is designed to sort-isolate, or bulk enrich early reporter expression shortly after transfection. EPIC may significantly reduce selection timelines and/or improve productivity of the resulting heterogeneous population.

Figure 20:
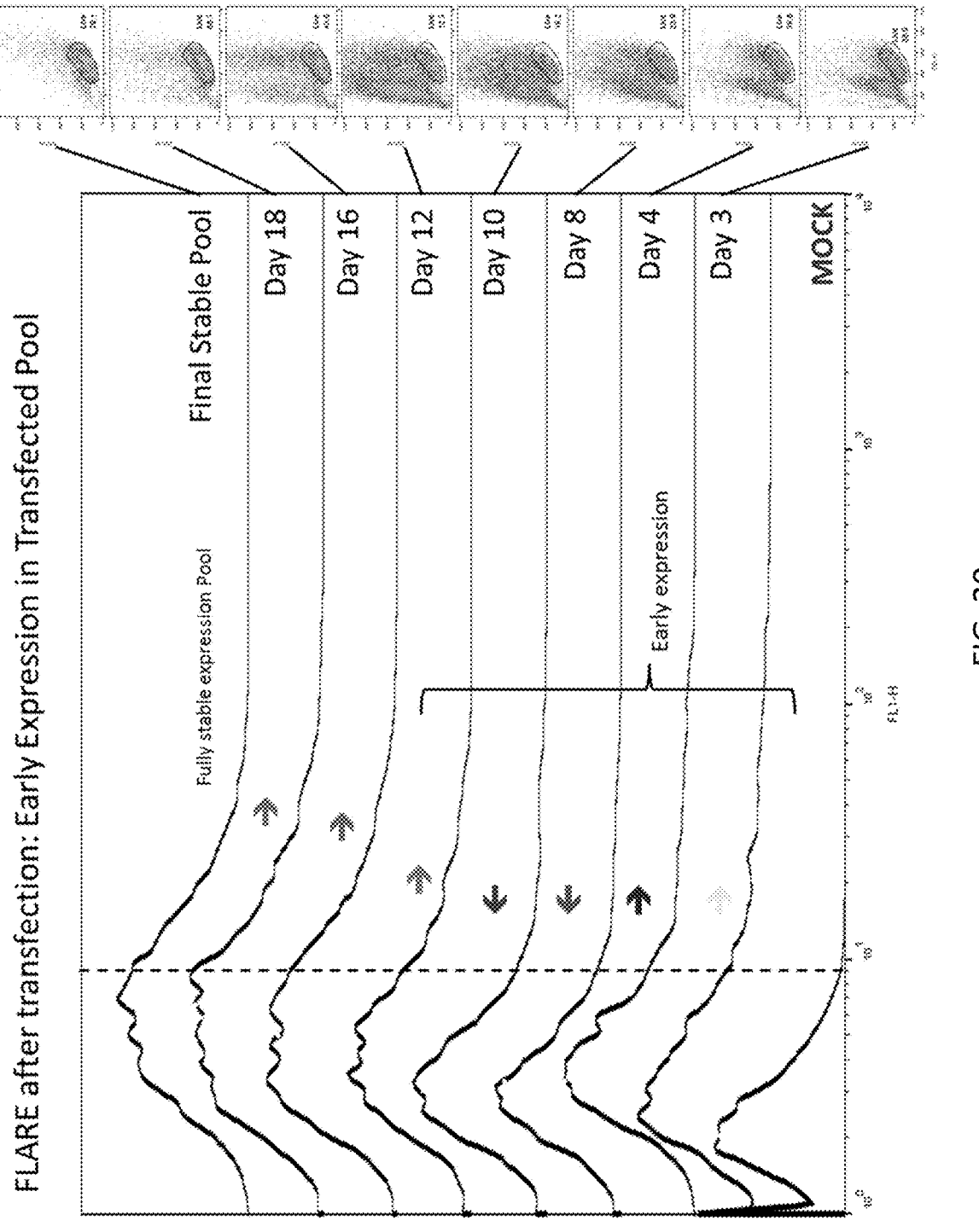
FIG. 20 is a diagram showing reporter expression of a transfected population of cells from day 3 to 21 in a nucleotide-deficient selection process (compared to mock transfected population). Transfected cells exhibited an apparent expression shortly after transfection (day 3-4) and then transitioned to stable expression upon completion of selection (day 18-21).
Figure 29:
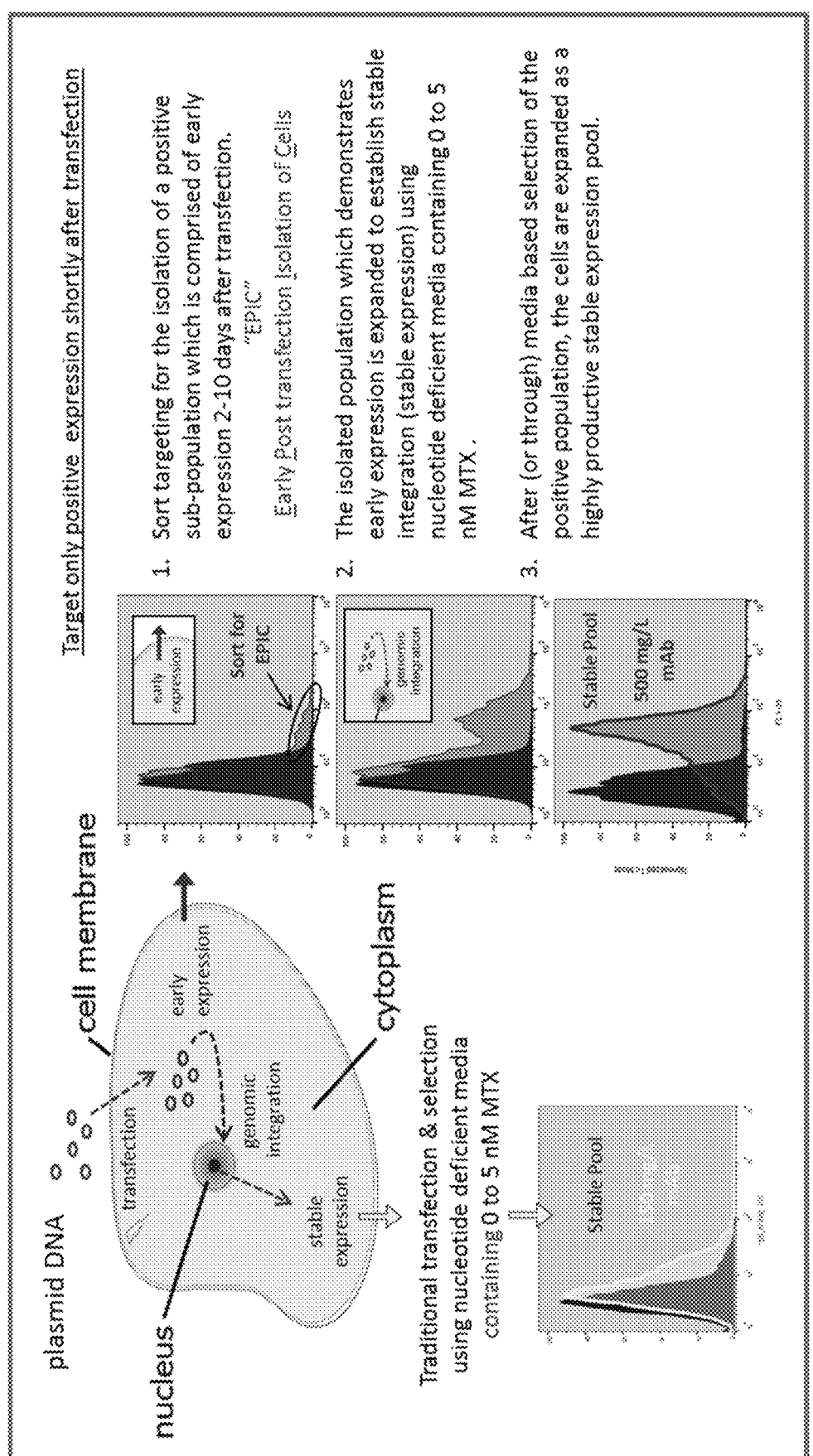
FIG. 29 is a schematic which illustrates the EPIC methodology (as used with flow cytometry sorting) compared with traditional transfection/selection methodology.

Experiments have been performed to investigate the reporter expression profile of a transfected population throughout the course of a nucleotide-deficient selection process. FIG. 29 depicts a general scheme for EPIC. FIG. 20 shows the apparent early expression of the reporter gene during the nucleotide-deficient selection process. These offset histograms demonstrate that early expression (e.g. day 3-4) is positive and sortable; making isolating a sub-population of transfected cells for an EPIC process feasible.

As shown in FIG. 29, EPIC can be executed by transfecting a population and allowing early expression to develop, which can be targeted for isolation using flow cytometry sorting. These sort-isolated early-expression populations can then be placed in a selection media to establish a stable expression pool. Isolation of these post-transfection early expression populations prior to selection yields improved productivity over standard transfection/selection methodologies alone.

Figure 23:
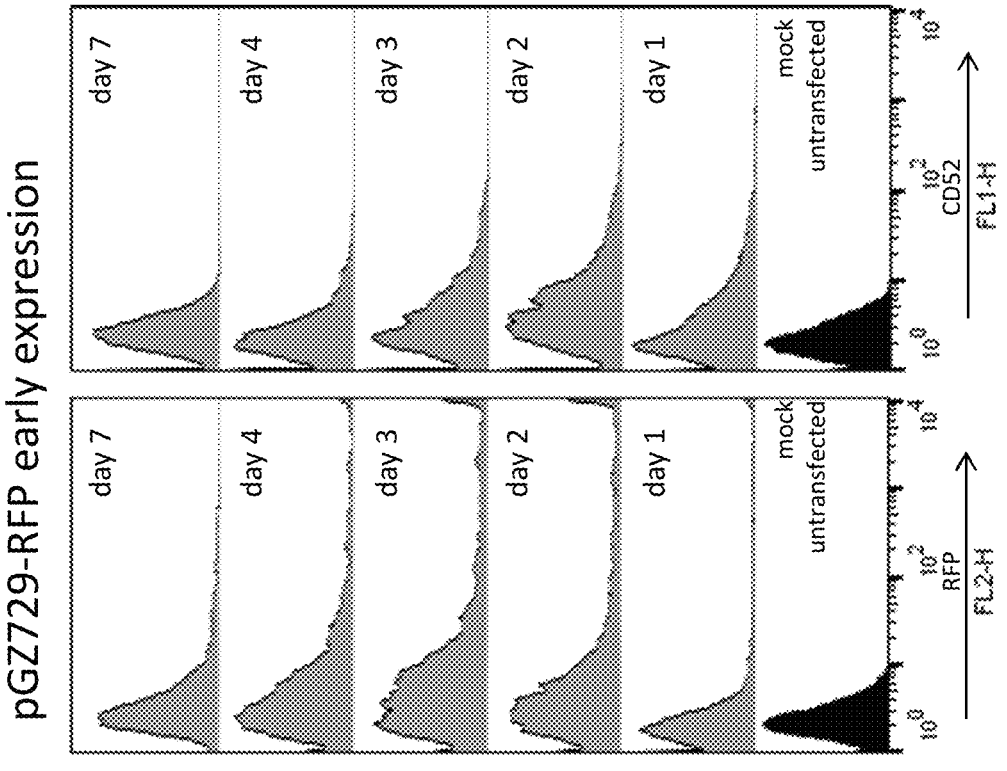
FIG. 23 is a series of FACS histogram offsets depicting the early expression of both red fluorescent protein (RFP) and cell surface reporter CD52 expression from the same vector (pGZ729-RFP). No selection pressure was applied to the transfected cells. Peak early expression for RFP and CD52 occurs between days 2 and 3.
Figure 24:
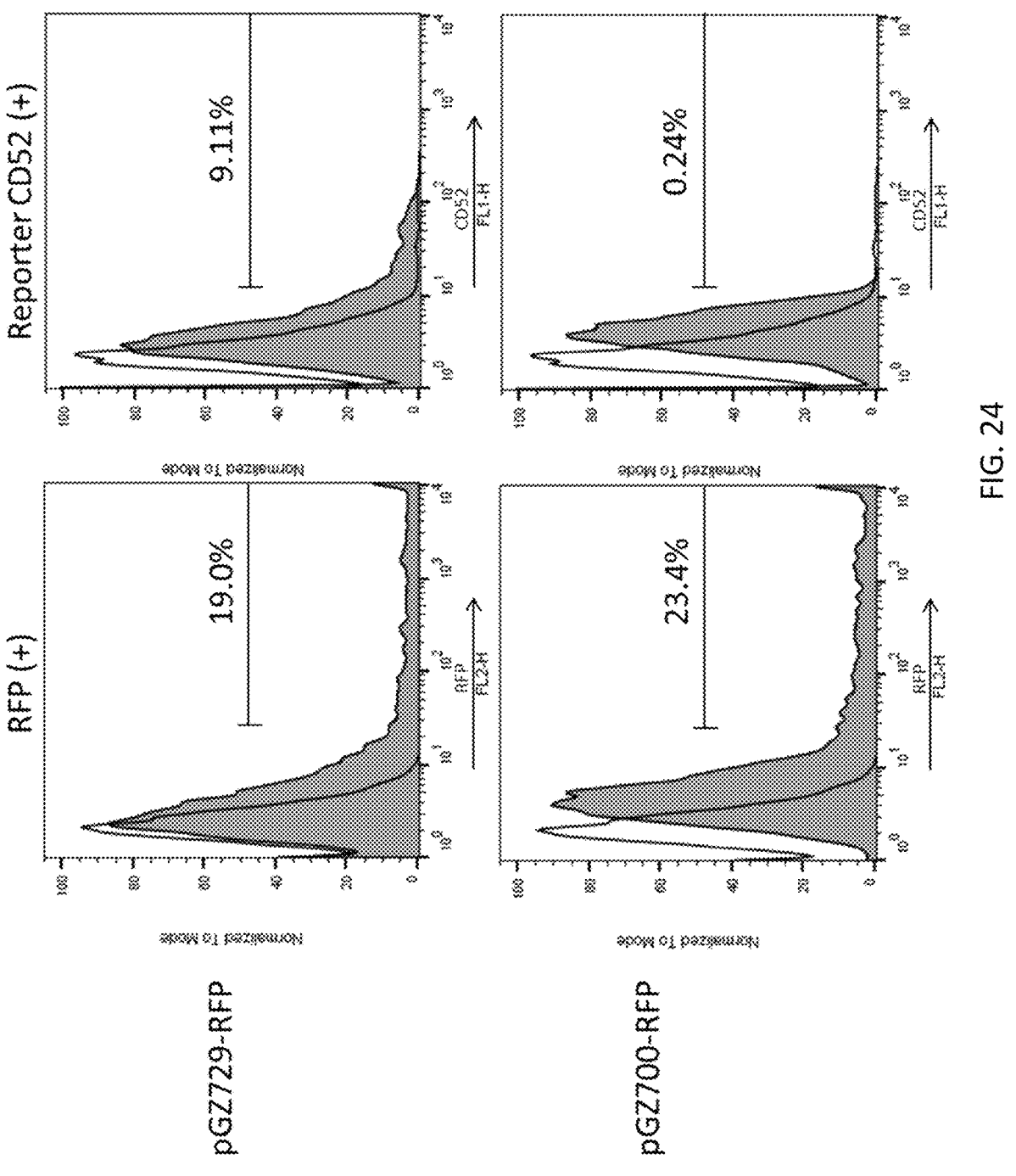
FIG. 24 is a series of FACS histogram offsets depicting the day 3 early expression of RFP and CD52 in cells transfected with pGZ729-RFP (encoding both selectable polypeptide CD52 and target polypeptide RFP) or pGZ700-RFP (encoding only target polypeptide RFP).
Figure 28:
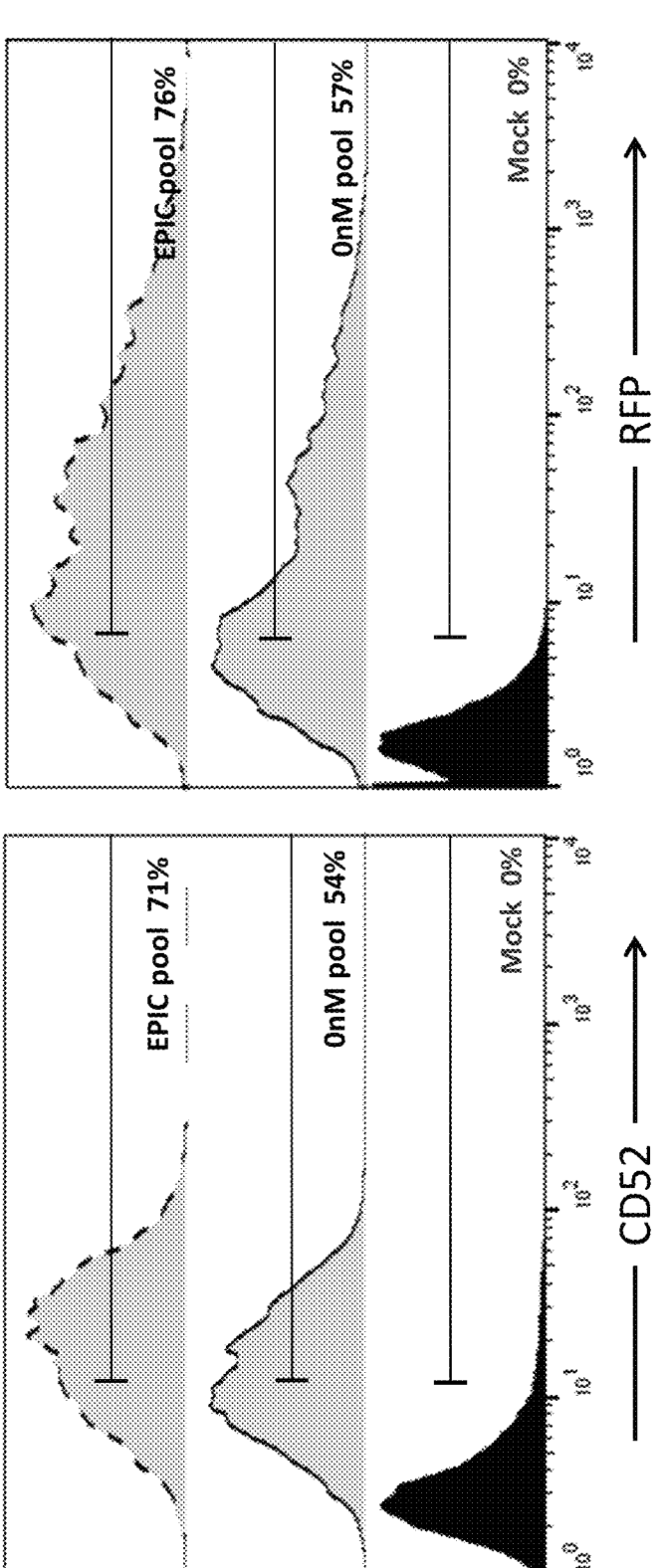
FIG. 28 is a series of histogram offsets depicting the comparative benefit of EPIC targeting to generate stable pools transfected with pGZ729-RFP. EPIC was used to target early RFP expression at day 2 which yielded a stable pool with improved RFP (and CD52 reporter expression) as compared to traditional transfection/selection methodologies (0 nM MTX).

To demonstrate proof of concept that detected CD52 signal is in fact early expression of CD52 reporter expression, vectors expressing both RFP and CD52 (pGZ729-RFP) and only RFP (pGZ700-RFP) were constructed and transfected for early expression evaluation. As shown in FIG. 23, CHO cells transfected with pGZ729-RFP produced early expression of both CD52 and RFP that peaked around days 2 and 3, with signal deteriorating out to day 7 post-transfection. Therefore, EPIC targeting on or near these days is suitable for isolation of early expression sub-populations of transfected host cells. In order to demonstrate that these llow intensity signals were in fact CD52 expression, CHO cells transfected with either pGZ729-RFP or pGZ700-RFP were analyzed for RFP and CD52 expression. As shown in FIG. 24, both CHO cells transfected with pGZ729-RFP and CHO cells transfected with pGZ700-RFP robustly expressed RFP (top left and bottom left, respectively), whereas CHO cells transfected with pGZ729-RFP had modest expression of CD52 (top right), and CHO cells transfected with pGZ700-RFP expressed essentially no detectable CD52 (bottom right). These data support the notion that these relatively low degree of fluorescence intensity signals were in fact CD52 expression from the alternate start expression cassette, and are suitable targets for sorting isolation (EPIC). As a further proof of principle, early RFP expression was targeted for EPIC from a transfected population using pGZ729-RFP to then generate a stable pool. Early RFP expression was targeted for sort isolation and collection two days after transfection (peak transience). The EPIC generated RFP positive sub-population was then used to establish a stable pool via selection in 0 nM MTX nucleotide deficient media. A standard transfection/selection pool was also generated to serve as comparative control. As shown in FIG. 28, the EPIC generated pool (which targeted early RFP expression) yielded a stable pool (EPIC pool) with greater RFP and CD52 reporter expression than traditional transfection/selection methodology alone (0 nM pool). Results demonstrate a FLARE independent proof of principle supporting the claim that EPIC generated pools are more productive than traditional transfection/selection methodologies.

Figure 25:
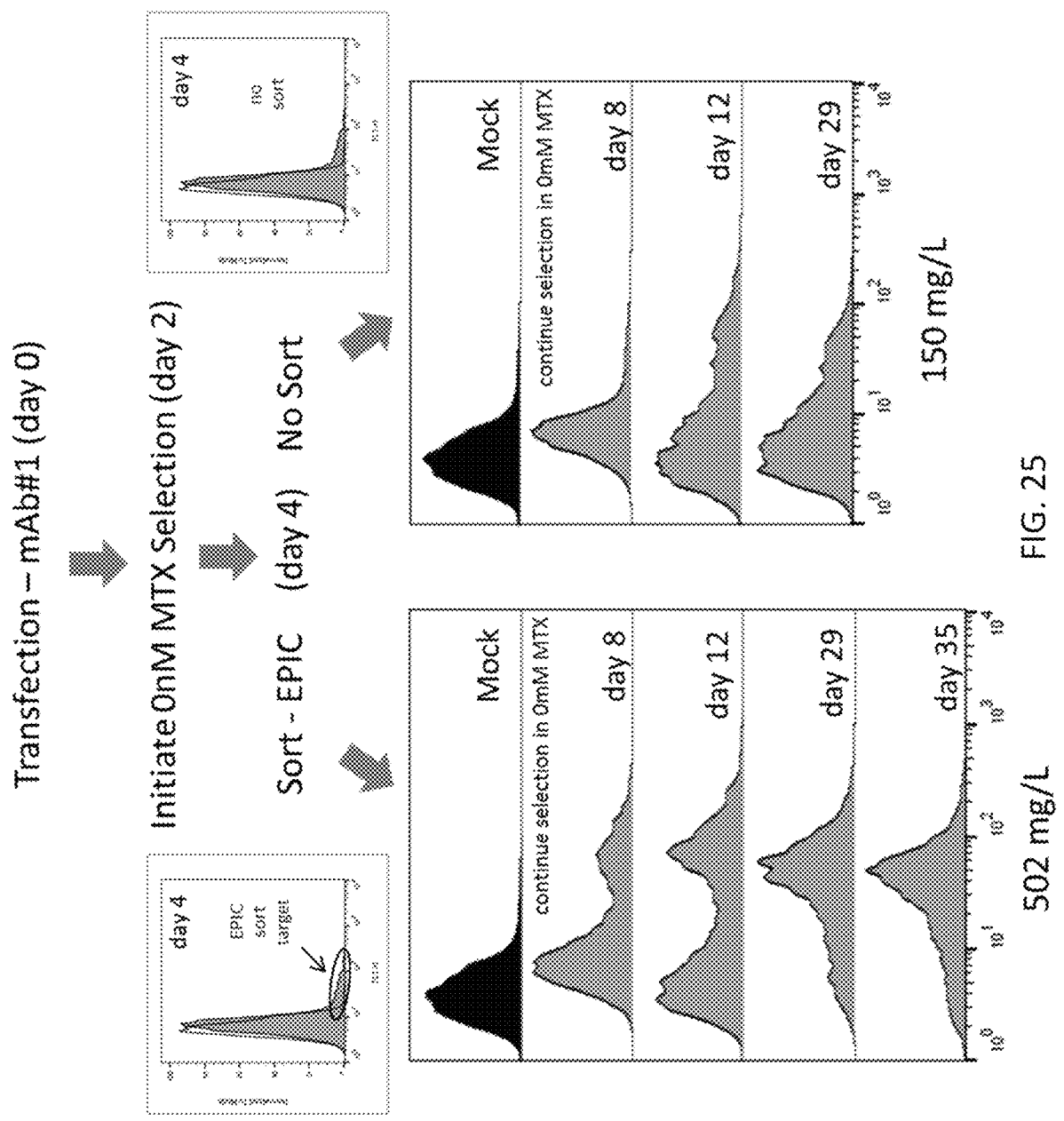
FIG. 25 is a schematic showing both the methodology of EPIC to generate a subpopulation of cells for selection shortly after transfection and the beneficial effects to both the reporter expression and monoclonal antibody (mAb) titers upon isolation/expansion of the sort-enriched population. Mock refers to mock transfection.

EPIC was initially attempted using mAb #1 in which CHO cells were transfected and given 2 days to recover after which 0 nM MTX selection was initiated to establish early expression. Four days after transfection, early expression of CD52 cell surface reporter was targeted for sort isolation (EPIC). Sorting targeted only positive expression which was collected as a bulk enriched population of about 1 million cells which was then allowed to continue selection in a nucleotide deficient media (0 nM MTX). As a control a non-sorted transfection was allowed to continue selection via standard selection procedure. As shown in FIG. 25, EPIC sorting yielded a slightly enriched population as shown by reporter expression compared to standard selection by day 8. As selection of both populations continued however, it was surprising to observe how this small EPIC sub-population became more prominent over time. In fact, the negative sub-population was all but eliminated upon selection completion. Comparatively, the standard selection method demonstrated a slight improvement in reporter expression which is historically typically. EPIC sorting, or isolating early expression, yields a subpopulation of positive expression that has a preferential survivability over the less expressive cells which in turn yields a more productive stable pool.

Figure 26:
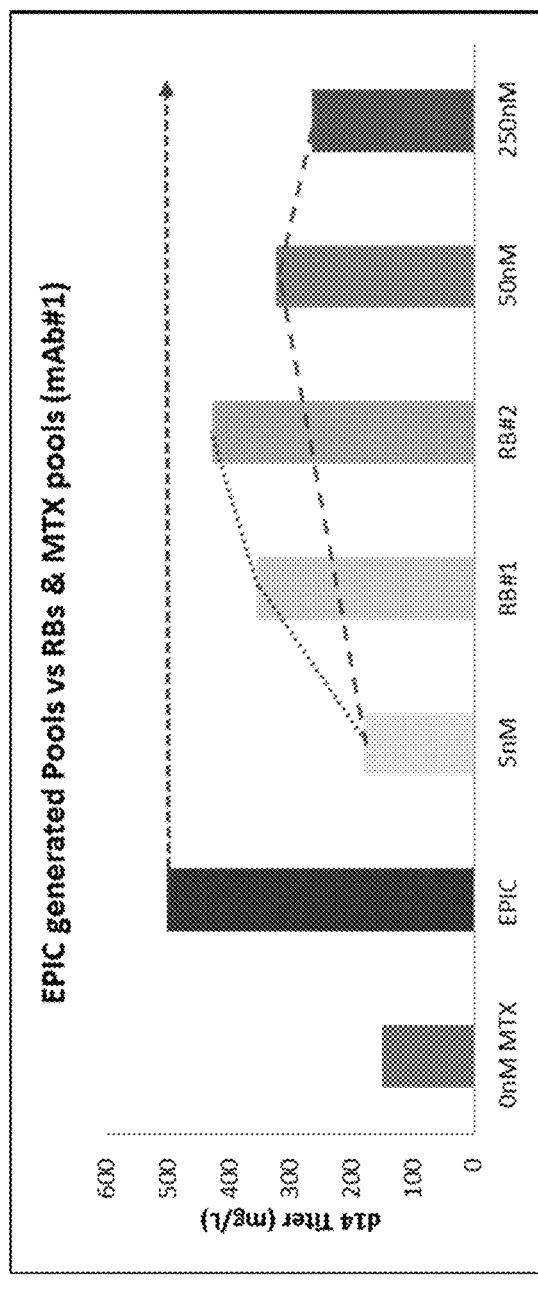
FIG. 26 is a graph depicting day 14 unfed batch titers for EPIC-generated pools as compared to traditional MTX methodologies.

The EPIC and standard selected pools were both used to establish unfed batch cultures to determine mAb #1 titers. As shown in FIGS. 25 and 26, the EPIC generated pool yielded a titer of 502 mg/L, far outpacing any pools generated by either rapid bulking or MTX amplification, again using no MTX throughout the processes. Comparatively, the pool generated by standard selection yielded a titer of 150 mg/L, which was 3-fold lower than that of the EPIC generated pool.

While, these initial EPIC sorts took 35 days, transfection/isolation/selection) to achieve completion to a stable pool, this was directly related to the small number of sorted cells collected (1 million) which then had to endure both the expansion and selection to a stable population. Such timelines could be greatly reduced by either simply collecting more cells and/or targeting a purer sort. Many of the cells sorted had high levels of impurities (cells with little to no expression) and had to be selected (killed) out, prolonging the selection/expansion times.

Figure 27:
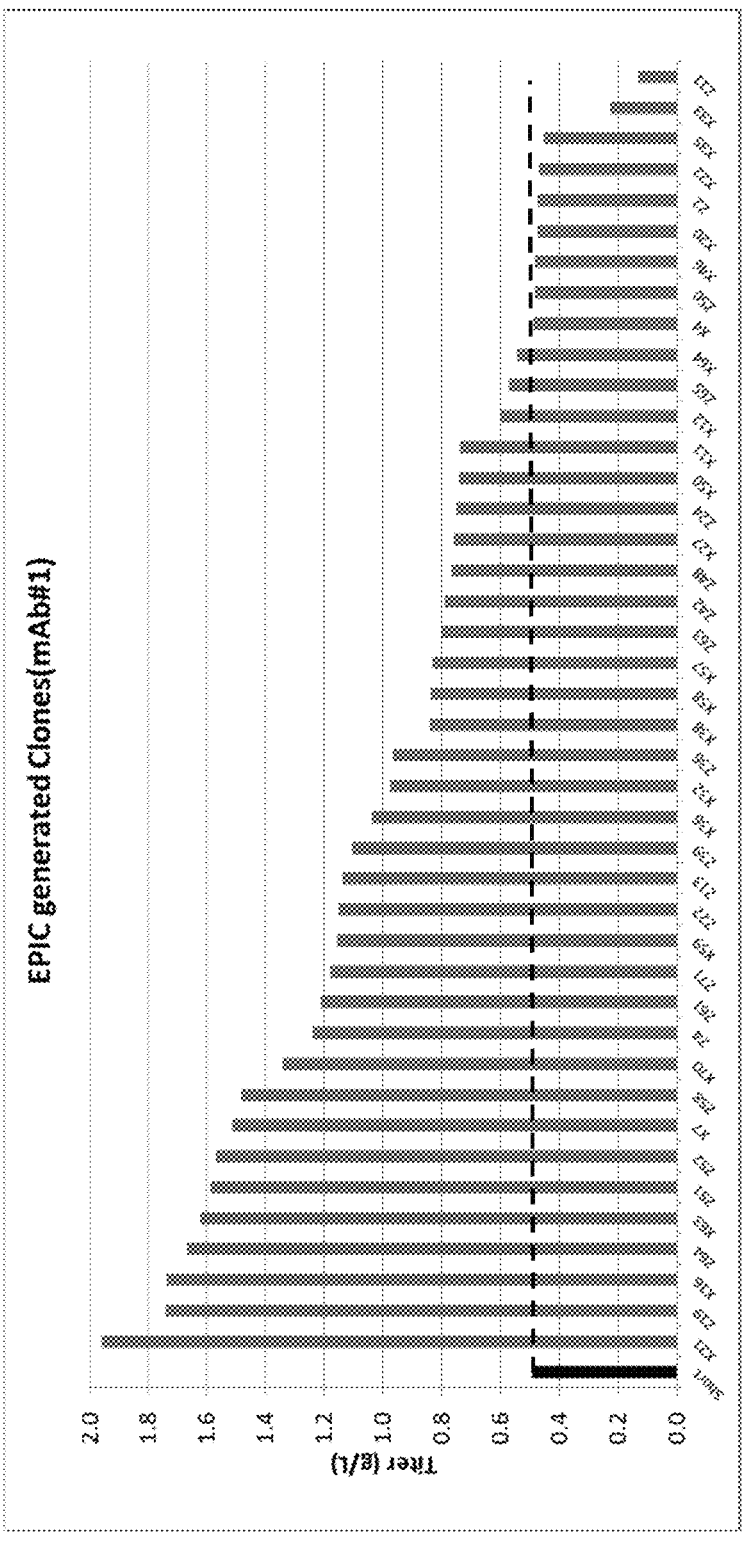
FIG. 27 is a graph depicting day 14 unfed batch titers from EPIC-generated clones which achieved top expression ranging from 1.5-2.0 g/L. Leftmost bar (0.5 g/L) represents titer for EPIC-sorted pool prior to cloning. All other vertical bars represent titers for individual clones.

This EPIC generated pool was next used to generate clones again using FLARE as previously described (see, e.g., Cairns, V. et al. (2011) Utilization of Non-AUG Initiation Codons in a Flow Cytometric Method for Efficient Selection of Recombinant Cell Lines. Biotechnol Bioeng 108(11):2611-2622). Briefly, FLARE was used to isolate and single cell plate the top 3-5% of reporter-expressing cells from each pool using FACS. Expanded clones were then screened (taking top 30% positive expressers), again using FLARE, to identify only the top tier clones to expand for target polypeptide titer evaluation. As shown in FIG. 27, top expressing EPIC generated clones achieved similar titers to those of the top expressing clones from traditional methods, e.g., using MTX-amplified (near 2.0 g/L). Results demonstrate that using EPIC to isolate early expression populations prior to selection is a viable alternative to traditional transfection and selection methodologies. EPIC offers a MTX independent methodology to achieve clone titers similar to those from traditional MTX methodologies resulting in potentially more robust and stable clones. EPIC is also amenable to MTX introduction during selection/expansion of EPIC generated populations which holds the potential to drive higher expression in these enriched populations.

Example 5: Immediate Repetitive Sorting for Viability Gain

Figure 21:
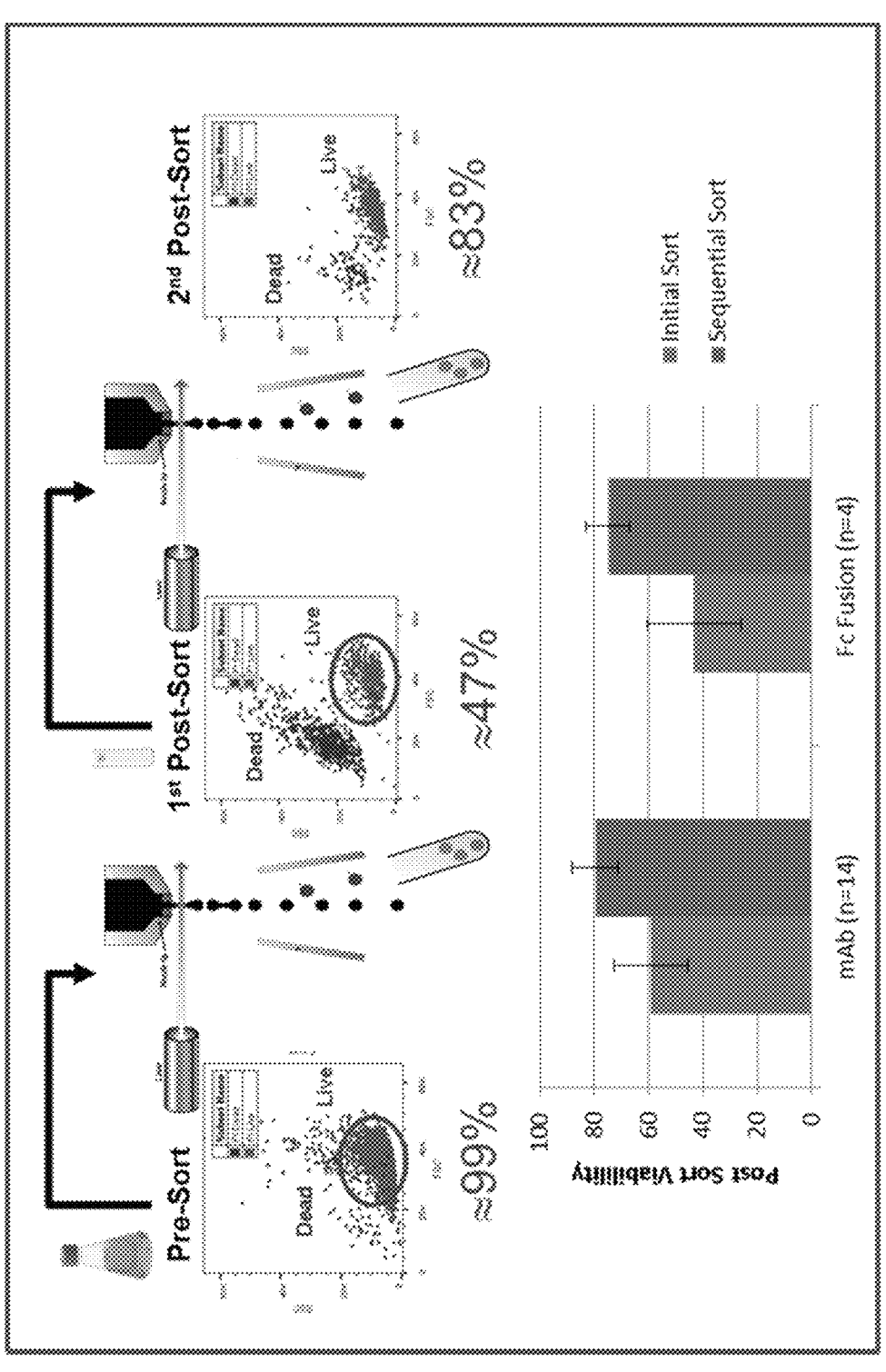
FIG. 21 is a diagram and a graph showing % viability after a first sort and subsequent gain in viability achieved with an immediate second sort.

It was often observed that CHO cells collected by sorting have poor cell viabilities as a bulk post-sort population. This viability was determined by immediate reanalysis of an aliquot of the post-sort population. Low post-sort viability was observed using two different cell sorters using two different CHO host cell lines. Optimization of different parameters and conditions in the cell sorting procedure was attempted in order to achieve higher post-sort cell viabilities on a consistent basis. During this work, it was surprisingly observed that sorted cells that were immediately re-sorted had significantly improved post-sort viabilities (about 83% viability after the re-sort compared to about 47% viability after the first sort, FIGS. 4 and 21). This phenomenon was discovered with high reporter expressing cells using FLARE with live gates but is independent of the reporter system. This independence was confirmed by showing that cells sorted based only on live gates showed improved viability via immediate repetitive sorting. This was demonstrated in two independent experiments generating mAb-producing subclones without FLARE (cells did not express reporter).

This process (immediate repeat sort) worked to improve post-sort cell viability by a significant degree. Further, as Table 2 shows, this was highly a reproducible result observed with both a newer model of sorter (BD Influx™) as well as an older model of sorter (FACS Aria). This result was shown with several protein-expressing (both mAb and Fc Fusion protein) cells, including those with and those without the FLARE system. Using this immediate repeat sorting methodology yielded improved viability in the population of cells collected by sorting, which is expected to translate into improved cloning efficiency when plating the sorted cells into well plates for clone generation.

TABLE 2

Immediate repetitive sorting viability of different protein-expressing cells

| Construct | % viability after $1^{st}$ sort | % viability after immediate $2^{nd}$ sort |
|---|---|---|
| sFcF#1 | 47 | 83 |
| | 40 | 77 |
| | 22 | 76 |
| | 64 | 71 |
| mAb #1 | 41 | 79 |
| | 65 | 89 |
| | 54 | 74 |
| | 57 | 63 |
| | 54 | 89 |
| | 66 | 80 |
| | 70 | 72 |
| mAb #3 | 76 | 82 |
| | 67 | 78 |
| | 79 | 89 |
| | 65 | 93 |
| mAb #2 | 58 | 69 |
| | 30 | 81 |
| | 47 | 77 |

What is claimed is:

1. A method of increasing viability of cells after fluorescence activated cell sorting (FACS), the method comprising:
   using a first round of FACS to select based on a viability marker a first sub-population of cells from a population of cells expressing a target polypeptide, and
   using a second round of FACS to select based on the viability marker a second sub-population of cells from the first sub-population of cells,
   wherein the first round and second round of FACS occur within 8 hours of each other, and wherein the viability marker is a forward scatter/side scatter population differentiation and/or a propidium iodide stain.

2. The method of claim 1, wherein the second sub-population has a post sort viability improvement of 1.2- to 4-fold compared to the initial sub-population post sort viability.

3. The method of claim 1, further comprising expanding the second sub-population.

4. The method of claim 1, further comprising individually culturing cells from the second sub-population in order to generate one or more clonal populations.

5. The method of claim 1, wherein the increasing viability of cells after FACS is performed after a batch selection method.

6. The method of claim 5, wherein the batch selection method comprises:
   (a) providing a heterogeneous population of producer cells, wherein the producer cells in the population express varying levels of a FACS selectable polypeptide and the target polypeptide that are encoded by the same multicistronic mRNA,
   (b) selecting from the heterogeneous population of producer cells a first heterogeneous sub-population of producer cells using FACS, wherein the producer cells in the first heterogeneous sub-population express the FACS selectable polypeptide at a level that is higher than the level of at least 80% of the producer cells in the heterogeneous population in (a), and
   (c) expanding the first heterogeneous sub-population of producer cells in drug-selection-free medium, thereby producing an expanded first heterogeneous sub-population of producer cells.

7. The method of claim 6, wherein the selection in step (b) is performed between 2 to about 15 days after transfection of the heterogeneous population of producer cells.

8. The method of claim 6, wherein the selection in step (b) is performed two days after transfection.

9. The method of claim 6, wherein the selection in step (b) is performed three days after transfection.

10. The method of claim 6, wherein the heterogeneous population of producer cells in (a) is produced by transfecting cells with a vector that encodes the multicistronic mRNA and subjecting the transfected cells to one round of medium-based selection to select cells expressing varying levels of the multicistronic mRNA.

11. The method of claim 10, wherein the vector further contains a dihydrofolate reductase (DHFR) gene.

12. The method of claim 10, wherein the medium-based selection is methotrexate-containing medium or nucleotide-deficient medium.

13. The method of claim 6, wherein the drug-selection-free medium is methotrexate-free medium or methionine sulphoximine-free medium.

14. The method of claim 6, further comprising:
   (d) selecting from the expanded first heterogeneous sub-population of producer cells in (c) a second heterogeneous sub-population of producer cells using FACS, wherein the producer cells in the second sub-population express the FACS selectable polypeptide at a level that is higher than the level of at least 80% of the producer cells in the expanded first heterogeneous sub-population of producer cells in (c), and
   (e) expanding the second heterogeneous sub-population of producer cells in a drug-selection-free medium, thereby producing an expanded second heterogeneous sub-population of producer cells.

15. The method of claim 6, wherein the multicistronic mRNA comprises a first open reading frame (ORF) that encodes the FACS selectable polypeptide and a second ORF that encodes the target polypeptide, wherein the first ORF is 5' to the second ORF.

16. The method of claim 15, wherein the first ORF has a non-AUG start codon.

17. The method of claim 15, wherein the second ORF has an AUG start codon.

18. The method of claim 15, wherein the ORF that encodes the FACS selectable polypeptide is devoid of any AUG sequences.

19. The method of claim 6, wherein the target polypeptide is selected from the group consisting of therapeutic agents, secreted proteins, antibodies, and Fc fusion proteins.

20. The method of claim 1, wherein the second round of FACS occurs as an immediate sort after the first round of FACs without any intervening cell steps between the first and second round of FACS.

21. The method of claim 1, wherein the first round and second round of FACS occur within 30 minutes to within 8 hours of each other.

22. The method of claim 1, wherein the first round and second round of FACS occur within 30 minutes of each other.

23. The method of claim 1, wherein the first round and second round of FACS occur within 60 minutes of each other.

* * * * *

SEQUENCE LISTING

```
Sequence total quantity: 8
SEQ ID NO: 1                moltype = AA   length = 61
FEATURE                     Location/Qualifiers
REGION                      1..61
                            note = Description of Artificial Sequence: Synthetic
                             polypeptide
source                      1..61
                            mol_type = protein
                            organism = synthetic construct
SEQUENCE: 1
LERFLFLLLT ISLLVLVQIQ TGLSGQNDTS QTSSPSASSN ISGGIFLFFV ANAIIHLFCF  60
S                                                                   61

SEQ ID NO: 2                moltype = AA   length = 128
FEATURE                     Location/Qualifiers
REGION                      1..128
                            note = Description of Artificial Sequence: Synthetic
                             polypeptide
source                      1..128
                            mol_type = protein
                            organism = synthetic construct
SEQUENCE: 2
LGIQGGSVLF GLLLVLVAVFC HSGHSLQCYN CPNPTADCKT AVNCSSDFDA CLITKAGLQV  60
YNNCWKFEHC NFNDVTTRLR ENELTYYCCK KDLCNFNEQL ENGGTSLSEK TVLLLVTPFL  120
AAAWSLHP                                                            128

SEQ ID NO: 3                moltype = DNA   length = 186
FEATURE                     Location/Qualifiers
misc_feature                1..186
                            note = Description of Artificial Sequence: Synthetic
                             polynucleotide
source                      1..186
                            mol_type = other DNA
                            organism = synthetic construct
SEQUENCE: 3
ttggagcgct tcctcttcct cctactcacc atcagcctcc tcgttttggt acaaatacaa  60
accggactct ccggacaaaa cgacaccagc caaaccagca gcccctcagc atccagcaac  120
ataagcggag gcattttcct tttcttcgtc gccaacgcca taatccacct cttctgcttc  180
agttga                                                              186

SEQ ID NO: 4                moltype = DNA   length = 387
FEATURE                     Location/Qualifiers
misc_feature                1..387
                            note = Description of Artificial Sequence: Synthetic
                             polynucleotide
source                      1..387
                            mol_type = other DNA
                            organism = synthetic construct
SEQUENCE: 4
ttgggaatcc aaggagggtc tgtcctgttc gggctgctgc tcgtcctcgc tgtcttctgc  60
cattccggtc atagcctgca gtgctacaac tgtcctaacc caactgctga ctgcaaaaca  120
gccgtcaatt gttcatctga ttttgacgcg tgtctcatta ccaaagctgg gttacaagtg  180
tataacaact gttggaagtt tgagcattgc aatttcaacg acgtcacaac ccgcttgagg  240
gaaaacgagc taacgtacta ctgctgcaag aaggacctgt gtaactttaa cgaacagctt  300
gaaaacggag ggacatcctt atcagagaaa acagttcttc tgctggtgac tccatttctg  360
gcagctgctt ggagccttca tccctaa                                       387

SEQ ID NO: 5                moltype = DNA   length = 8123
FEATURE                     Location/Qualifiers
misc_feature                1..8123
                            note = Description of Artificial Sequence: Synthetic
                             polynucleotide
source                      1..8123
                            mol_type = other DNA
                            organism = synthetic construct
SEQUENCE: 5
ggatccgctg tggaatgtgt gtcagttagg gtgtggaaag tccccaggct ccccagcagg  60
cagaagtatg caaagcatgc atctcaatta gtcagcaacc aggtgtggaa agtccccagg  120
ctccccagca ggcagaagta tgcaaagcat gcatctcaat tagtcagcaa ccatagtccc  180
gcccctaact ccgcccatcc cgcccctaac tccgcccagt tccgcccatt ctccgcccca  240
tggctgacta atttttttta tttatgcaga ggccgaggcc gcctcggcct ctgagctatt  300
ccagaagtag tgaggaggct ttttggaggc ctaggctttt gcaaaaagc ttggggggggg  360
ggacagctca gggctgcgat ttcgcgccaa acttgacggc aatcctagcg tgaaggctgg  420
taggatttta tccccgctgc catcatggtt cgaccattga actgcatcgt cgccgtgtcc  480
caaaatatgg ggattggcaa gaacggagac tacccctggc ctccgctcag gaacgagttc  540
aagtacttcc aaagaatgac cacaacctct tcagtggaag gtaaacagaa tctggtgatt  600
atgggtagga aacctggtt ctccattcct gagaagaatc gacctttaaa ggacagaatt  660
aatatagttc tcagtagaga actcaaagaa ccaccacgag gagctcattt tcttgccaaa  720
```

-continued

```
agtttggatg atgccttaag acttattgaa caaccggaat tggcaagtaa agtagacatg    780
gtttggatag tcggaggcag ttctgtttac caggaagcca tgaatcaacc aggccacctc    840
agactctttg tgacaaggat catgcaggaa tttgaaagtg acacgttttt cccagaaatt    900
gatttgggga aatataaact tctcccagaa tacccaggcg tcctctctga ggtccaggag    960
gaaaaaggca tcaagtataa gtttgaagtc tacgagaaga agactaaca ggaagatgct    1020
ttcaagttct ctgctcccct cctaaagcta tgcattttta taagaccatg ggacttttgc    1080
tggctttaga tctttgtgaa ggaaccttac ttctgtggtg tgacataatt ggacaaacta    1140
cctacagaga tttaaagctc taaggtaaat ataaaatttt taagtgtata atgtgttaaa    1200
ctactgattc taattgtttg tgtattttag attccaacct atggaactga tgaatgggag    1260
cagtggtgga atgcctttaa tgaggaaaac ctgtttttgct cagaagaaat gccatctagt    1320
gatgatgagg ctactgctga ctctcaacat tctactcctc caaaaaagaa gagaaaggta    1380
gaagacccca aggactttcc ttcagaattg ctaagttttt tgagtcatgc tgtgtttagt    1440
aatagaactc ttgcttgctt tgctatttac accacaaagg aaaaagctgc actgctatac    1500
aagaaaatta tggaaaaata ttctgtaacc tttataagta ggcataacag ttataatcat    1560
aacatactgt tttttcttac tccacacagg catagagtgt ctgctattaa taactatgct    1620
caaaaattgt gtaccctttag cttttttaatt tgtaaagggg ttaataagga atatttgatg    1680
tatagtgcct tgactagaga tcataatcag ccataccaca tttgtagagg ttttacttgc    1740
tttaaaaaac ctcccacacc tcccccctgaa cctgaaacat aaaatgaatg caattgttgt    1800
tgttaacttg tttattgcag cttataatgg ttacaaataa agcaatagca tcacaaattt    1860
cacaaataaa gcattttttt cactgcattc tagttgtggt ttgtccaaac tcatcaatgt    1920
atcttatcat gtctggatcc tctacgccgg acgcatcgtg gccggcatca ccggcgccac    1980
aggtgcggtt gctggcgcct atatcgccga catcaccgat ggggaagatc gggctcgcca    2040
cttcgggctc atgagcgctt gtttcggcgt gggtatggtg gcaggccgtg gccggggggac    2100
tgttgggcgc catctccttg catgcaccat tccttgcggc ggcggtgctc aacggcctca    2160
acctactact gggctgcttc ctaatgcagg agtcgcataa gggagagcgt cgaccgatgc    2220
ccttgagagc cttcaaccca gtcagctcct tccggtgggc gcggggcatg actatcgtcg    2280
ccgcacttat gactgtcttc tttatcatgc aactcgtagg acaggtgccg gcagcgctct    2340
gggtcatttt cggcgaggac cgctttcgct ggagcgcgac gatgatcggc ctgtcgcttg    2400
cggtattcgg aatcttgcac gccctcgctc aagccttcgt cactggtccc gccaccaaac    2460
gtttcggcga gaagcaggcc attatcgccg gcatggcgga cggtacgtct    2520
tgctggcgtt cgcgacgcga ggctggatgg ccttccccat tatgattctt ctcgcttccg    2580
gcggcatcgg gatgcccgcg ttgcaggcca tgctgtccag gcaggtagat gacgaccatc    2640
agggacagct tcaaggccag caaaaggcca ggaaccgtaa aaaggccgcg ttgctggcgt    2700
ttttccatag gctccgcccc cctgacgagc atcacaaaaa tcgacgctca agtcagaggt    2760
ggcgaaaccc gacaggacta taaagatacc aggcgtttcc ccctggaagc tccctcgtgc    2820
gctctcctgt tccgaccctg ccgcttaccg gatacctgtc cgcctttctc ccttcgggaa    2880
gcgtggcgct ttctcatagc tcacgctgta ggtatctcag ttcggtgtag tcgttcgct    2940
ccaagctggg ctgtgtgcac gaaccccccg ttcagcccga ccgctgcgcc ttatccggta    3000
actatcgtct tgagtccaac ccggtaagac acgacttatc gccactggca gcagccactg    3060
gtaacaggat tagcagagcg aggtatgtag gcggtgctac agagttcttg aagtggtggc    3120
ctaactacgg ctacactaga aggacagtat ttggtatctg cgctctgctg aagccagtta    3180
ccttcggaaa aagagttggt agctcttgat ccggcaaaca aaccaccgct ggtagcggtg    3240
gtttttttgt ttgcaagcag cagattacgc gcagaaaaaa aggatctcaa gaagatcctt    3300
tgatctttc tacggggtct gacgctcagt ggaacgaaaa ctcacgttaa gggattttgg    3360
tcatgagatt atcaaaaagg atcttcacct agatccttt aaattaaaaa tgaagtttta    3420
aatcaatcta aagtatatat gagtaaactt ggtctgacag ttaccaatgc ttaatcagtg    3480
aggcacctat ctcagcgatc tgtctatttc gttcatccat agttgcctga ctccccgtcg    3540
tgtagataac tacgatacgg gagggcttac catctggccc cagtgctgca atgataccgc    3600
gagacccacg ctcaccggct ccagatttat cagcaataaa ccagccagcc ggaagggccg    3660
agcgcagaag tggtcctgca actttatccg cctccatcca gtctattaat tgttgccggg    3720
aagctagagt aagtagttcg ccagttaata gtttgcgcaa cgttgttgcc attgctgcag    3780
gcatcgtggt gtcacgctcg tcgtttggta tggcttcatt cagctccggt tcccaacgat    3840
caaggcgagt tacatgatcc cccatgttgt gcaaaaaagc ggttagctcc ttcggtcctc    3900
cgatcgttgt cagaagtaag ttggccgcag tgttatcact catggttatg gcagcactgc    3960
ataattctct tactgtcatg ccatccgtaa gatgcttttc tgtgactggt gagtactcaa    4020
ccaagtcatt ctgagaatag tgtatgcggc gaccgagttg ctcttgcccg gcgtcaacac    4080
gggataatac cgcgccacat agcagaactt taaaagtgct catcattgga aaacgttctt    4140
cggggcgaaa actctcaagg atcttaccgc tgttgagatc cagttcgatg taacccactc    4200
gtgcacccaa ctgatcttca gcatctttta ctttcaccag cgtttctggg tgagcaaaaa    4260
caggaaggca aaatgccgca aaaaagggga taagggcgac acggaaatgt tgaatactca    4320
tactcttcct tttcaatat tattgaagca tttatcaggg ttattgtctc atgagcggat    4380
acatatttga atgtatttag aaaaataaac aaataggggt tccgcgcaca tttccccgaa    4440
aagtgccacc tgacgtctaa gaaaccatta ttatcatgac attaacctat aaaaatagc    4500
gtatcacgag gccctttcgt cttcaagaat tggggaccaa gacagaacca taagctcagtg    4560
ggatagatca gaaatgttcc agaggtggga tgggggccaga gtgcctgccc cttgaaccgt    4620
cccaggggacc agaggtgaca aagtggcaac acaggtcctg cctgggaatc tggtctgctc    4680
ctacttagta aagctgcctg gtgtcacaca agaggccccc acttattcct gcaccoctgg    4740
tggtaggtgg cgtcttctcc cctgcagcca ccaggctccc ctgagaacac tgccggcagt    4800
cctcattgac aggcagtatt cgctctgccc caccccccacc tgtgaattgc agggctggca    4860
ggtcctcagg cagctggcaa accgcctgaa caactgagag atacagggcc agggccaggg    4920
cagtcccgtc ccccggaggc agggagggga cgtgctggga aagttctctc tctcaggccc    4980
aggttggtga ctgcagaagg cttctgtcaa atctcttttg tgggaaccac agagtagccc    5040
tgaacgtggg ggtgtgcttc cagtatactc tggggtcacc ctttccatac tggaggcctc    5100
tgcaacttca aaatgctctg ctaccaacct agcacaagga agttggtcca gcctccccac    5160
gcagggccac tgctgcagtc catatatgga ctaagccttc cttggtttca acacctacac    5220
tcactgagcc cctactatgt gtatgcagag ccgagcaggg ccctgagcat ctcatctgaa    5280
gcaccacttct tgcctaaatt cagttttctg tcactttctc ccaggaggtg tgtgtccctc    5340
taagctaagc caggggtccc tcacccctgc cccactccca tccctagtgt aggtatcagc    5400
tgaagagctt cctgagcaga acactcttgg gtgctgacat tttgataaat aggcccatgt    5460
```

```
ttaggagagc aggggtccgg gggcgggaga tcttctctgg tggattgagg gctccaagaa   5520
ctactctttg agcacgctgc ccctcccaga gtccccacag cctccagatg gactagaaca   5580
cagttcggct gtggctgcac ataactaaca gaggatagat ggtgggtccc agcccaacag   5640
tgcctggcaa tcacccagag ccaccagcta acggccttgg cttagttttt tgcctgggtg   5700
tgatcaggca gccctccaaa actgcccgga ctccatgaca agttttgctt gttctataga   5760
gcacagttcc tttctaggtc tggggcaagg gacatcggga gacatcttcc tgcaacagct   5820
ccagtcactg gaccaccagg ctcgccctgt ctttggtgtg tggccctgag tctcctaagt   5880
ggcccaaacc tgtgaagacc cctccaacca cagttttgct tctaaattgt accccaacac   5940
acctagcaaa ttgaaacccc accagaagtc ccccagatct ggctttccgg ctattgctgg   6000
caagggggag tgactcccgg cccattcaat ccaggccccg cgtgttcctc aaacaagaag   6060
ccacgtaaac ataaaccgag cctccatgct gacccttgcc catcgaggta ctcaatgttc   6120
acgtgatatc cacacccaga gggtcctggg gtgggtgcat gagccccaga atgcaggctt   6180
gataaccgag accctgaatc gggcagtgtc cacaagggcg gaggccagtc atgcatgttc   6240
gggcctatgg ggccagcacc caacgccaaa actctccatc ctcttcctca atctcgcttt   6300
ctctctctct ctcttttttt ttttttattt ttttttttttg caaaaggagg ggagaggggg   6360
taaaaaaatg ctgcactgtg cggctaggcc ggtgagtgag cggcgcggag ccaatcagcg   6420
ctcgccgttc cgaaagttgc cttttatggc tcgagtggcc gctgtggcgt cctataaaac   6480
ccggcggcgc aacgcgcagc cactgtcgag tccgcgtcca cccgcgagca caggcctttc   6540
gcagctcttt cttcgccgct ccacacccgc caccaggtaa gcaggacaa caggcccagc   6600
cggccacagc cctcccgtgg gcagtgaccg cgctgcaggg tcgcgggga cactcggcgc   6660
ggacaccggg gaaggctgga gggtggtgcc gggccgcgga gcggacactt tcagatccaa   6720
ctttcagtcc agggtgtaga cccttttacag ccgcattgcc acggtgtaga caccggtgga   6780
cccgctctgg ctcagagcac gcggcttggg ggaacccatt agggtcgcag tgtgggcgct   6840
atgagagccg atgcagcttt cgggtgttga accgtatctg cccaccttgg ggggaggaca   6900
caaggtcggg agccaaacgc cacgatcatg ccttggtggc ccatgggtct ttgtctaaac   6960
cggtttgccc atttggcttg ccgggcgggc ggcgcgggcg ggccggctc ggccgggtgg   7020
gggctggggtt gccactgcgc ttgcgcgctc tatggctggg tattggggcg cgtgcacgct   7080
ggggagggag cccttcctct tcccccttctc ccaagttaaa cttgcgcgtg cgtattgaga   7140
cttggagcgc ggccaccggg gttgggcgag ggcgggggccg ttgtccggaa ggggcggggt   7200
cgcagcggct tcggggcgcc tgctcgcgct tcctgctgga tgtggtcgcc tcccgcgcgc   7260
gcactagccg cccgccggcg gggcgaaggc ggggcttgcg cccgtttggg gaggggcgg   7320
aggcctggct tcctgccgtg gggccgcctc cggaccagcg tttgcctctt atggtaataa   7380
cgcggccggc ctgggcttcc tttgtcccct gagtttgggc gcgcgccccc tggcggcccg   7440
aggccgcggc ttgccggaag tgggcagggc ggcagcggct gcgcctagtg gcccgctagt   7500
gaccgcgacc ctcttttgtg ccctgatata gttcgccgga tcctaccgcg gtagcggccg   7560
cgccaccttg gagcgcttcc tcttcctcct actcaccatc agcctcctcg ttttggtaca   7620
aatacaaacc ggactctccg gacaaaacga caccagccaa accagcagcc cctcagcatc   7680
cagcaacata agcggaggca ttttcctttt cttcgtcgcc aacgccataa tccacctctt   7740
ctgcttcagt tgaaggccgg ccaatacgta ggcgcgccat tgagtgagtg atttggcgcg   7800
ccaagatatc acacccggga ttaattaaag gtacctacgc gtagaattcc acgtagtggt   7860
ttaaactcta gatactcgag ggatctggat cataatcagc cataccacat ttgtagaggt   7920
tttacttgct ttaaaaaacc tcccacacct cccctgaac ctgaaacata aaatgaatgc   7980
aattgttgtt gttaacttgt ttattgcagc ttataatggt tacaaataaa gcaatagcat   8040
cacaaatttc acaaataaag cattttttc actgcattct agttgtggtt tgtccaaact   8100
catcaatgta tcttatcatg tct                                          8123
```

```
SEQ ID NO: 6          moltype = AA   length = 74
FEATURE               Location/Qualifiers
REGION                1..74
                      note = Description of Artificial Sequence: Synthetic
                       polypeptide
source                1..74
                      mol_type = protein
                      organism = synthetic construct
SEQUENCE: 6
LKSFLLFLTI ILLVVIQIQT GSLGQATTAA SGTNKNSTST KKTPLKSGAS SIIDAGACSF   60
LFFANTLICL FYLS                                                      74

SEQ ID NO: 7          moltype = DNA   length = 10
FEATURE               Location/Qualifiers
misc_feature          1..10
                      note = Description of Unknown: Kozak sequence
source                1..10
                      mol_type = other DNA
                      organism = unidentified
SEQUENCE: 7
gccrccatgg                                                           10

SEQ ID NO: 8          moltype = DNA   length = 233
FEATURE               Location/Qualifiers
misc_feature          1..233
                      note = Description of Artificial Sequence: Synthetic
                       polynucleotide
source                1..233
                      mol_type = other DNA
                      organism = synthetic construct
SEQUENCE: 8
ttgaagagct tcctcctctt cctcactatc attcttctcg tagtcattca gatacaaaca   60
ggatccttag gacaagccac tacggccgct tcaggtacta caaaaaacag cacctccacc   120
```

-continued

```
aaaaaaaccc ccttaaagag cggggcctca tccatcatcg acgcgggcgc ttgcagtttc   180
ctcttcttcg ccaataccct tatttgcctc ttctacctca gctaactgag taa           233
```